US008580980B2

(12) United States Patent
Osaka et al.

(10) Patent No.: US 8,580,980 B2
(45) Date of Patent: Nov. 12, 2013

(54) ORGANIC COMPOUND, LIGHT-EMITTING ELEMENT, LIGHT-EMITTING DEVICE, ELECTRONIC DEVICE, AND LIGHTING DEVICE

(75) Inventors: Harue Osaka, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 46 days.

(21) Appl. No.: 13/328,541

(22) Filed: Dec. 16, 2011

(65) Prior Publication Data

US 2012/0157694 A1   Jun. 21, 2012

(30) Foreign Application Priority Data

Dec. 17, 2010  (JP) ................................ 2010-281941

(51) Int. Cl.
  *C07D 307/91* (2006.01)
  *H01J 1/62* (2006.01)

(52) U.S. Cl.
  USPC ........... 549/460; 549/429; 549/456; 428/690; 428/917; 313/504; 313/506

(58) Field of Classification Search
  USPC .............. 549/29, 43, 429, 456, 460; 428/690, 428/917; 313/504, 506
  See application file for complete search history.

(56) References Cited

U.S. PATENT DOCUMENTS

| 6,905,788 | B2 | 6/2005 | Tyan et al. |
| 7,700,201 | B2 | 4/2010 | Seo et al. |
| 2004/0110958 | A1 | 6/2004 | Nishiyama et al. |
| 2005/0221124 | A1 | 10/2005 | Hwang et al. |
| 2006/0180812 | A1 | 8/2006 | Sakata et al. |
| 2007/0009758 | A1 | 1/2007 | Funahashi |
| 2007/0215867 | A1 | 9/2007 | Kawakami et al. |
| 2007/0215889 | A1 | 9/2007 | Kawakami et al. |
| 2007/0252511 | A1 | 11/2007 | Funahashi |
| 2008/0015399 | A1 | 1/2008 | Funahashi |
| 2008/0122345 | A1 | 5/2008 | Sakata et al. |
| 2008/0124572 | A1 | 5/2008 | Mizuki et al. |
| 2008/0206598 | A1 | 8/2008 | Ohsawa et al. |
| 2009/0159877 | A1 | 6/2009 | Meng |
| 2010/0155714 | A1 | 6/2010 | Seo et al. |
| 2010/0314615 | A1 | 12/2010 | Mizuki et al. |
| 2011/0095270 | A1 | 4/2011 | Meng |
| 2011/0095678 | A1 | 4/2011 | Ogita et al. |
| 2011/0156016 | A1 | 6/2011 | Kawamura et al. |
| 2011/0248246 | A1 | 10/2011 | Ogita et al. |
| 2012/0112169 | A1 | 5/2012 | Mizuki et al. |

FOREIGN PATENT DOCUMENTS

| JP | 2004-204238 | 7/2004 |
| JP | 3926791 B2 | 6/2007 |
| JP | 4188401 B2 | 11/2008 |
| WO | WO 2005/108348 A1 | 11/2005 |
| WO | WO 2005/113531 A1 | 12/2005 |
| WO | WO 2005/108348 A1 | 3/2008 |
| WO | WO 2009/084512 A1 | 7/2009 |
| WO | WO 2010/013675 A1 | 2/2010 |
| WO | WO 2010/013676 A1 | 2/2010 |
| WO | WO 2010/122810 A1 | 10/2010 |

OTHER PUBLICATIONS

Goldsmith, C.R. et al., "C-H Bond Activation by a Ferric Methoxide Complex: Modeling the Rate-Determining Step in the Mechanism of Lipoxygenase," J. Am. Chem. Soc., vol. 124, No. 1, 2002, pp. 83-96.
Onishi, T. et al, "A Method of Measuring an Energy Level," *High Molecular EL Materials Development of Light Emitting High Molecular Compounds*, Kyoritsu Shuppan, Dec. 25, 2004, p. 64-67 (with English translation, pp. 1-3).

*Primary Examiner* — Golam M M Shameem
(74) *Attorney, Agent, or Firm* — Husch Blackwell LLP

(57) ABSTRACT

Provided is a novel anthracene compound represented by a general formula (G1). In the formula, $Q^1$ represents an oxygen atom or a sulfur atom, $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. In addition, $\alpha^1$ to $\alpha^3$ separately represent a substituted or unsubstituted phenylene group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1.

11 Claims, 34 Drawing Sheets

(G1)

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a novel material that can be applied to a light-emitting element. In addition, the present invention relates to a light-emitting element, a light-emitting device, an electronic device, and a lighting device each including the material.

2. Description of the Related Art

In recent years, research and development have been extensively conducted on light-emitting elements using electroluminescence (EL). In a basic structure of such a light-emitting element, a layer containing a light-emitting substance is interposed between a pair of electrodes. By voltage application to this element, light emission can be obtained from the substance having a light-emitting property.

Such light-emitting elements are classified into a self-luminous type, and thus have advantages over liquid crystal displays, such as high pixel visibility and the eliminated need for a backlight. Accordingly, such light-emitting elements are thought to be suitable as flat panel display elements. The light-emitting elements have another great advantage that they can be manufactured to be thin and light. Further, very high speed response is one of the features of such elements.

Further, since such a light-emitting element can be formed in a film shape, plane light emission can be easily obtained. Therefore, a large-area element capable of the plane light emission can be fainted. This is a feature which is difficult to obtain from point light sources typified by an incandescent lamp and an LED or linear light sources typified by a fluorescent lamp. Accordingly, the light-emitting elements using EL have a great deal of potential for use as planar light sources which can be applied to illumination and the like.

Light-emitting elements using EL can be roughly classified in accordance with whether the light-emitting substance is an organic compound or an inorganic compound. In an organic EL element including a layer containing the light-emitting organic compound between a pair of electrodes, voltage application to the light-emitting element causes electrons and holes to be injected from a cathode and an anode, respectively, into the layer containing the light-emitting organic compound, and current flows. As a result of the injection of both electrons and holes, the light-emitting organic compound is excited, and when the light-emitting organic compound returns to a ground state from an excited state, the light-emitting organic compound emits light.

Having such a mechanism, the above-described light-emitting element is called a current-excitation light-emitting element. Note that the excited states formed by an organic compound include a singlet excited state and a triplet excited state, and luminescence from the singlet excited state is referred to as fluorescence, whereas luminescence from the triplet excited state is referred to as phosphorescence.

There are many problems which depend on substances in improving element characteristics of such a light-emitting element. Therefore, improvement of an element structure, development of a substance, and the like have been carried out in order to solve the problems. For example, Patent Document 1 discloses a light-emitting element in which a compound having an anthracene skeleton is used as a light-emitting material. However, it cannot be said that the light-emitting element has sufficiently high reliability.

In addition to light emission by recombination of carriers excited with a current, there is also a method of light emission in which excitation energy is transferred from an organic compound excited with a current to another organic compound and accordingly the latter organic compound is excited to emit light. This method is effective in the case where the emission efficiency is reduced (concentration quenching) due to stacking interaction caused by a high concentration of organic molecules that are desired to produce luminescence. In organic EL elements, the method is generally applied to the element structure used in which a light-emitting material is dispersed in a light-emitting layer (a light-emitting layer is doped with a light-emitting material). Doping a host material with organic molecules that are desired to emit light suppresses the stacking interaction, whereby efficiency of a light-emitting element can be increased. In such a light-emitting element, excitation energy is transferred from a host material excited by current excitation to a dopant material, making the dopant material emit light. Note that when Substance A is dispersed in a matrix formed of Substance B, Substance B forming the matrix is called a host material while Substance A dispersed in the matrix is called a dopant material.

Among these dopant materials, types of material that emits blue light are fewer than those of material that emits light of a color having a long wavelength (e.g., red, orange, yellow, or green). Among them, favorable materials are few. It is because blue light emission needs a material with small conjugation, and thus, there is limitation on a skeleton to be selected. In addition, it is also because blue light emission needs a higher energy than light emission of a color having a long wavelength, and the high energy easily degrades a dopant material.

From the above, a material for a blue light-emitting element is desired in order to provide a highly reliable organic EL element that emits favorable blue light.

REFERENCE

Patent Document

[Patent Document 1] PCT International Publication No. 2005/113531

SUMMARY OF THE INVENTION

In view of the above-described problems, an object of one embodiment of the present invention is to provide a novel element material. Another object of one embodiment of the present invention is to provide a novel substance that emits blue light.

A further object is to provide a light-emitting element, a light-emitting device, a lighting device, and an electronic device including the novel substance.

One embodiment of the present invention is an anthracene compound represented by a general formula (G1) below.

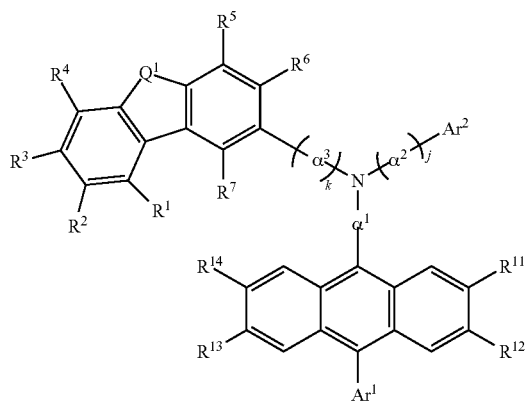

(G1)

In the general formula (G1), $Q^1$ represents an oxygen atom or a sulfur atom, and $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. In addition, $\alpha^1$ to $\alpha^3$ separately represent a substituted or unsubstituted phenylene group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1.

Alternatively, $\alpha^1$ to $\alpha^3$ in the general formula (G1) may be separately any one of structures represented by structural formulas ($\alpha$-1) to ($\alpha$-3) below.

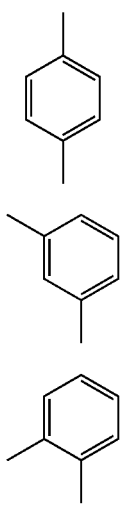

($\alpha$-1)

($\alpha$-2)

($\alpha$-3)

Another embodiment of the present invention is an anthracene compound represented by a general formula (G2) below.

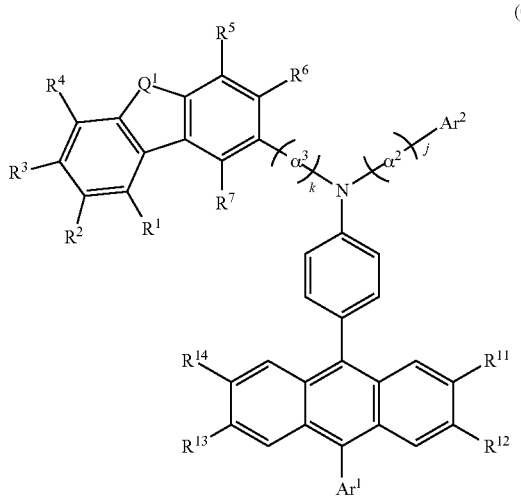

(G2)

In the general formula (G2), $Q^1$ represents an oxygen atom or a sulfur atom, $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. In addition, $\alpha^2$ and $\alpha^3$ separately represent a substituted or unsubstituted phenylene group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1.

Another embodiment of the present invention is an anthracene compound represented by a general formula (G3) below.

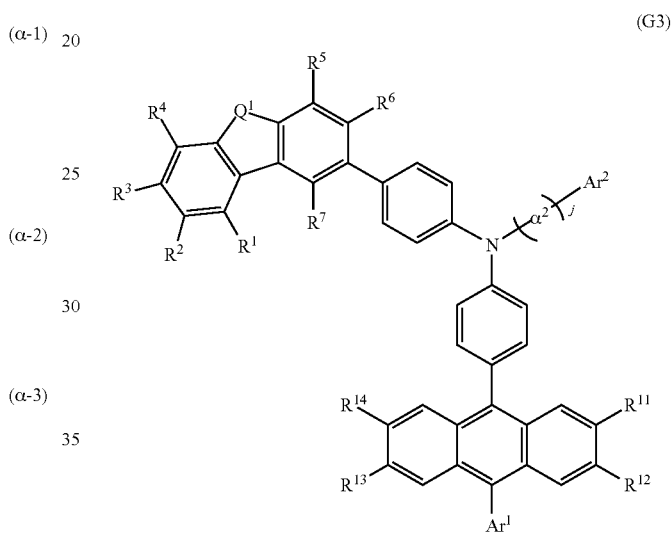

(G3)

In the general formula (G3), $Q^1$ represents an oxygen atom or a sulfur atom, $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. In addition, $\alpha^2$ represents a substituted or unsubstituted phenylene group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j is 0 or 1.

$Ar^1$ in the general formulas (G1) to (G3) may be any one of structures represented by structural formulas (Ar1-1) to (Ar1-4) below.

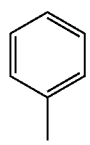

(Ar1-1)

-continued (Ar1-2)

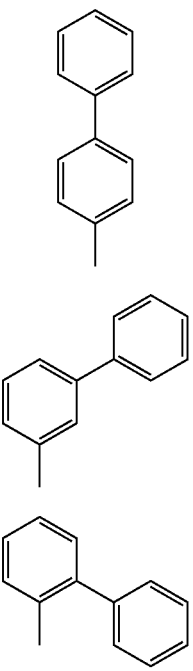

(Ar1-3)

(Ar1-4)

Ar² in the general formulas (G1) to (G3) may be a structure represented by a structural formula (Ar2-1) or a general formula (Ar2-2) below.

(Ar2-1)

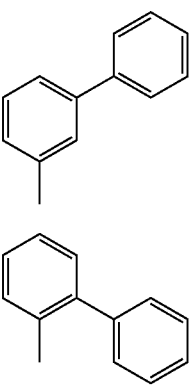

(Ar2-2)

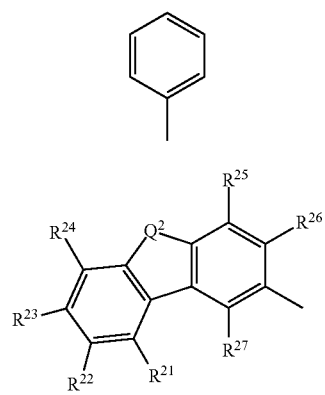

In the general formula (Ar2-2), $Q^2$ represents an oxygen atom or a sulfur atom, $R^{21}$ to $R^{27}$ separately represent any one of a hydrogen atom, an alkyl group having 1 to 6 carbon atoms, a substituted or unsubstituted phenyl group, and a substituted or unsubstituted biphenyl group.

$R^1$ to $R^7$ and $R^{11}$ to $R^{14}$ in the general formulas (G1) to (G3) may be separately any one of structures represented by structural formulas (R-1) to (R-9) below.

(R-1)

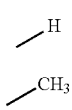

(R-2)

-continued

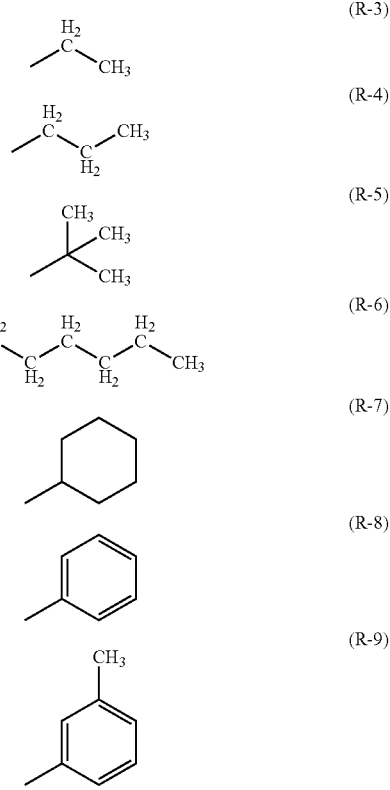

Another embodiment of the present invention is a light-emitting element including any of the above anthracene compounds.

Another embodiment of the present invention is a light-emitting device including the above light-emitting element.

Another embodiment of the present invention is a lighting device including the above light-emitting device.

Another embodiment of the present invention is an electronic device including the above light-emitting device.

Note that the light-emitting device in this specification includes an image display device, a light source, and an electronic device in its category. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

An anthracene compound according to one embodiment of the present invention can emit visible light having a short wavelength, and can emit blue light with favorable color purity.

In addition, by using the anthracene compound according to one embodiment of the present invention, a light-emitting element having high emission efficiency and high reliability can be obtained.

Further, by using this light-emitting element, a light-emitting device, an electronic device, and a lighting device each having high reliability can be obtained.

DETAILED DESCRIPTION OF THE INVENTION

Figure 1A:
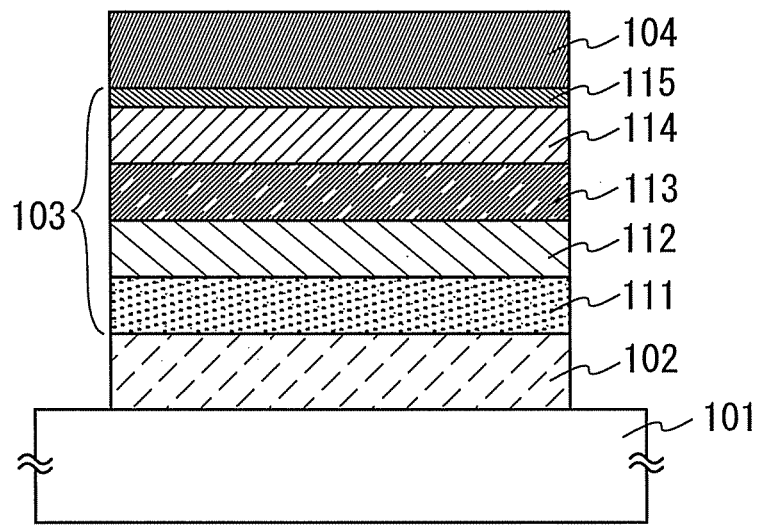
FIGS. 1A and 1B illustrate light-emitting elements according to embodiments of the present invention.

Hereinafter, embodiments of the present invention will be described in detail with reference to the accompanying drawings. However, the invention is not limited to the description below, and those skilled in the art will appreciate that a variety of modifications can be made to the modes and details without departing from the spirit and scope of the invention. Therefore, the invention should not be construed as being limited to the description in the following embodiments.

Embodiment 1

This embodiment shows an anthracene compound which is one embodiment of the present invention.

The anthracene compound in this embodiment is represented by a general formula (G1) below.

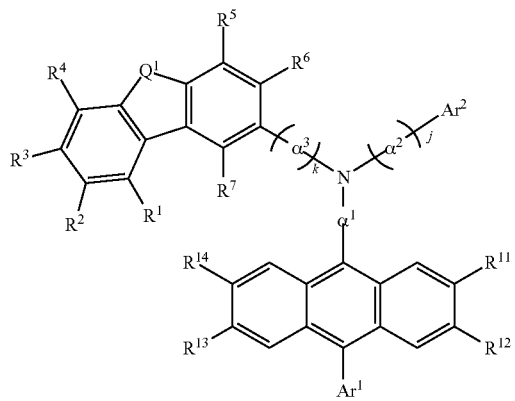

(G1)

In the general formula (G1), $Q^1$ represents an oxygen atom or a sulfur atom, $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. In addition, $\alpha^1$ to $\alpha^3$ separately represent a substituted or unsubstituted phenylene group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1.

For easier synthesis, k is preferably 0.

Note that any of $R^1$ to $R^7$ and $R^{11}$ to $R^{14}$ in the general formula (G1) preferably has an alkyl group as a substituent, or $Ar^1$ or $Ar^2$ in the general formula (G1) preferably has an alkyl group as a substituent, because in which case the solubility to an organic solvent is increased, thereby purification becomes easier. With the increase in solubility, a more uniform film can be formed in wet process manufacture of an organic EL element.

For easier synthesis, any of $R^1$ to $R^7$ and $R^{11}$ to $R^{14}$ in the general formula (G1) is preferably hydrogen, or $Ar^1$ or $Ar^2$ in the general formula (G1) is preferably unsubstituted.

Since the anthracene compound represented by the general formula (G1) includes a sterically bulky structure, such as a dibenzofuranyl group or a dibenzothiophenyl group, in a molecule, interaction between molecules is suppressed and the morphology (the form of molecules) is improved. Accordingly, a film formed using the anthracene compound represented by the general formula (G1) has a higher quality; thus, in the case where such a film is used for a light-emitting layer, concentration quenching and excimer formation can be suppressed more easily.

Conjugation of a dibenzofuranyl group and that of a dibenzothiophenyl group are not large because their skeletons have low molecular weight. Therefore, even when either skeleton is included in a molecule, the conjugation is barely likely to extend, so that emission color having a short wavelength can be obtained.

Any of $R^1$ to $R^7$ and $R^{11}$ to $R^{14}$ in the general formula (G1) preferably has an aryl group such as a phenyl group or a biphenyl group, or an alkyl group, as a substituent, because in which case a more sterical structure is obtained and interaction between molecules is more suppressed. Therefore, the morphology (the form of molecules) can be improved. In a similar manner, $Ar^1$ or $Ar^2$ in the general formula (G1) preferably has an aryl group such as a phenyl group or a biphenyl group, or an alkyl group, as a substituent, because in which case an even more sterical structure is obtained and interaction between molecules is even more suppressed.

Further, a dibenzofuranyl group or a dibenzothiophenyl group which is bonded to a nitrogen atom of an amine at the 2-position of the dibenzofuranyl group or the dibenzothiophenyl group is stable to holes and is a skeleton having a high hole-injection and hole-transport properties. In addition, an anthracene skeleton is stable to carriers and has a high carrier-transport property. Therefore, an anthracene compound which includes a dibenzofuranyl group or a dibenzothiophenyl group in a molecule, such as the anthracene compound represented by the general formula (G1), achieves high efficiency and long lifetime when used for a light-emitting element, and is suitable as a material for a light-emitting element.

Since an anthracene skeleton having high fluorescent quantum yield is used, the emission efficiency can be high.

An anthracene skeleton has high reactivity at the 9-position and the 10-position; therefore, for chemical stability (stability to carriers and excitation), a skeleton including $\alpha^1$ is preferably bonded at both the 9-position and $Ar^1$ is preferably bonded at the 10-position.

Specific examples of a substituent represented by any of $\alpha^1$ to $\alpha^3$ in the general formula (G1) include structural formulas (α-1) to (α-3) below.

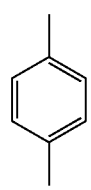

(α-1)

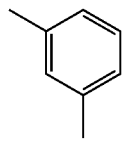

(α-2)

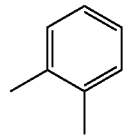

(α-3)

It is preferable that an anthracene compound have a substituent represented by the structural formula (α-1) as $\alpha^1$ in the general formula (G1), as represented by a general formula (G2) below.

In this manner, the use of a phenylene group between an anthracene skeleton and a nitrogen atom of an amine prevents conjugation of the anthracene from extending; and thus, light emission having a short wavelength (blue) can be obtained.

In this case, a paraphenylene group, i.e., the structural formula (α-1), is preferably included as $\alpha^1$ for higher stability of the excited state.

Alternatively, it is more preferable that a metaphenylene group, i.e., the structural formula (α-2), be included as $\alpha^1$, or an orthophenylene group, i.e., the structural formula (α-3), be included as $\alpha^1$, because in which case conjugation of the aryl group bonded to the phenylene group is barely likely to extend to the amine bonded to the phenylene group at the other site, so that a material can emit light having a shorter wavelength.

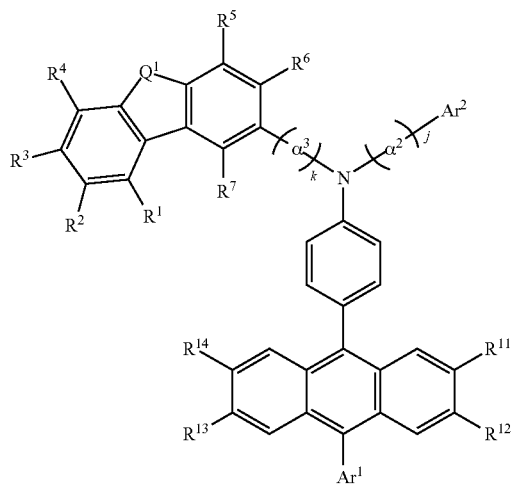

(G2)

In the general formula (G2), $Q^1$ represents an oxygen atom or a sulfur atom, $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. In addition, $\alpha^2$ and $\alpha^3$ separately represent a substituted or unsubstituted phenylene group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1.

Specific examples of a substituent represented by any of $\alpha^2$ and $\alpha^3$ in the general formula (G2) include the structural formulas (α-1) to (α-3) above.

Alternatively, it is more preferable that an anthracene compound have a substituent represented by the structural formula (α-1) as α³ in the general formula (G2), as represented by a general formula (G3) below.

(G3)

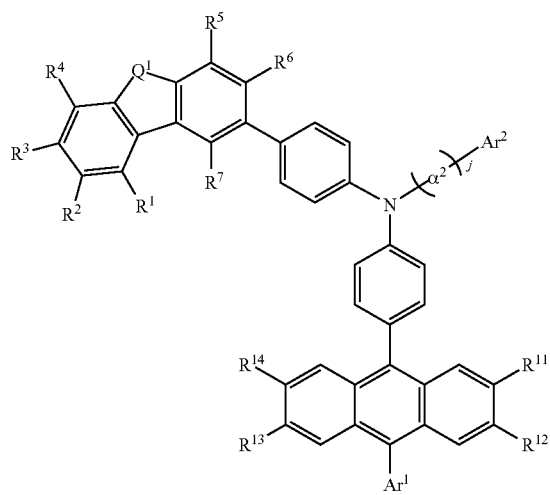

In the general formula (G3), $Q^1$ represents an oxygen atom or a sulfur atom, and $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. In addition, $α^2$ represents a substituted or unsubstituted phenylene group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j is 0 or 1.

Specific examples of a substituent represented by $α^2$ in the general formula (G3) include the structural formulas (α-1) to (α-3) above.

Specific examples of a substituent represented by $Ar^1$ in the general formulas (G1) to (G3) include structural formulas (Ar1-1) to (Ar1-4) below, and the like.

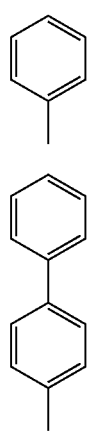

(Ar1-1)

(Ar1-2)

(Ar1-3)

(Ar1-4)

Specific examples of a substituent represented by $Ar^2$ in the general formulas (G1) to (G3) include structural formulas (Ar2-1) and (Ar2-2) below, and the like.

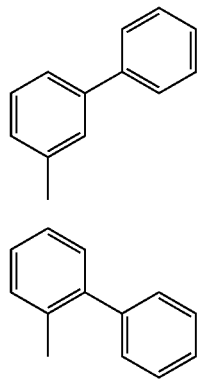

(Ar2-1)

(Ar2-2)

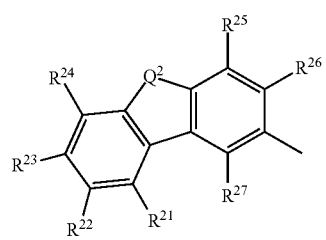

In the general formula (Ar2-2), $Q^2$ represents an oxygen atom or a sulfur atom, $R^{21}$ to $R^{27}$ separately represent any one of a hydrogen atom, an alkyl group having 1 to 6 carbon atoms, a substituted or unsubstituted phenyl group, and a substituted or unsubstituted biphenyl group.

When a substituent represented by $Ar^2$ is the general formula (Ar2-2) above, it is more preferable that j be 1 and $α^2$ be a paraphenylene group, i.e., the structural formula (α-1). In addition, it is preferable that $Q^1$ in the general formulas (G1) to (G3) and $Q^2$ in the general formula (Ar2-2) be the same elements. When these heterocycles have substituents, it is more preferable that the heterocycle including $Q^1$ and the heterocycle including $Q^2$ have the same substituents at the same position (e.g., $R^5$ and $R^{25}$, or $R^6$ and $R^{26}$).

For easier synthesis, it is even more preferable that the heterocycle including $Q^1$ and the heterocycle including $Q^2$ be unsubstituted.

Specific examples of a substituent represented by any of $R^1$ to $R^7$ and $R^{11}$ to $R^{14}$ in the general formulas (G1) to (G3) and $R^{21}$ to $R^{27}$ in the general formula (Ar2-2) include structural formulas (R-1) to (R-9) below, and the like.

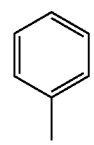

(R-1)

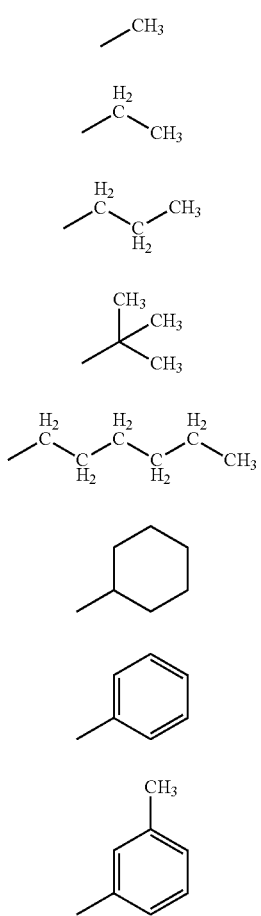
(R-2)
(R-3)
(R-4)
(R-5)
(R-6)
(R-7)
(R-8)
(R-9)
Specific examples of an anthracene compound represented by any of the general formulas (G1) to (G3) include anthracene compounds represented by structural formulas (100) to (115). However, the present invention is not limited thereto.
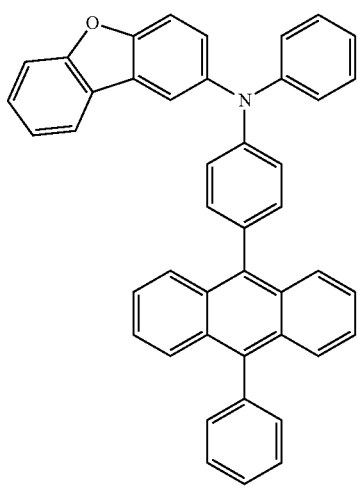
(100)
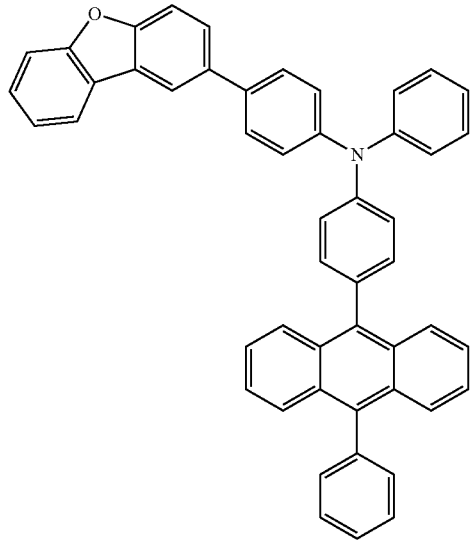
(101)
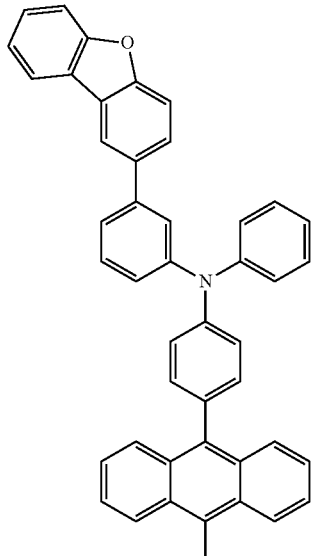
(102)
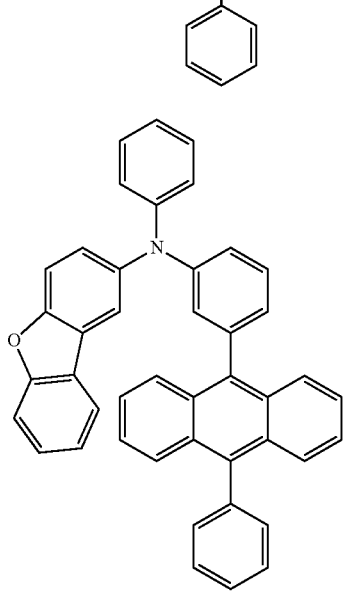
(103)

-continued
(104)
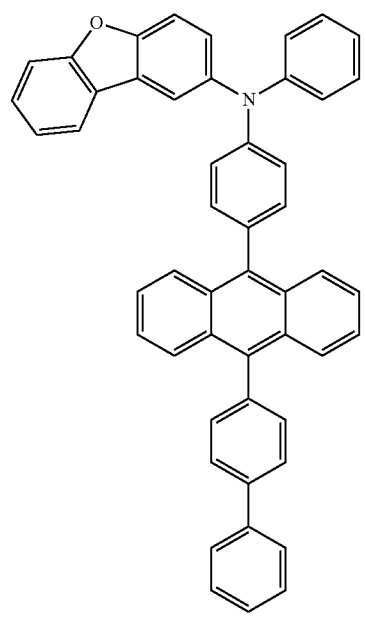
(105)
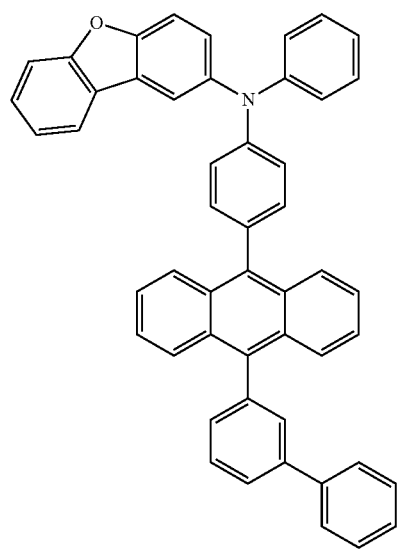
(106)
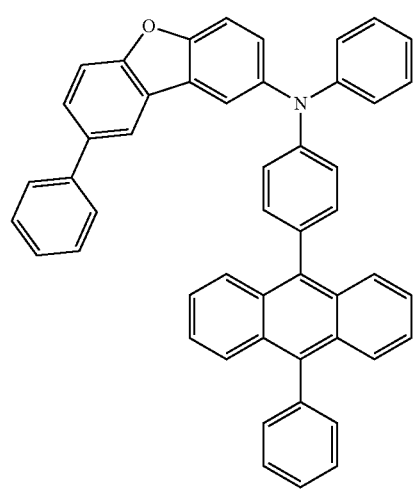
-continued
(107)
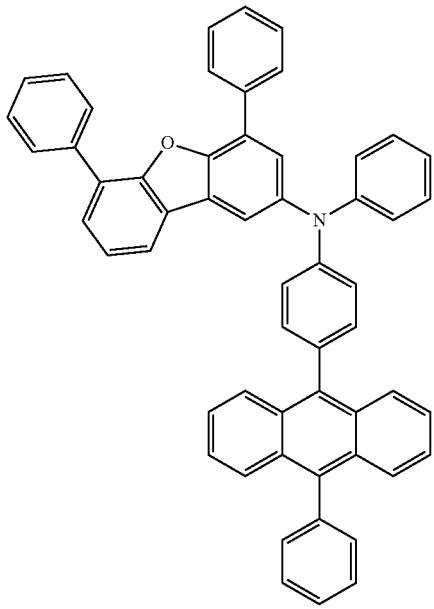
(108)
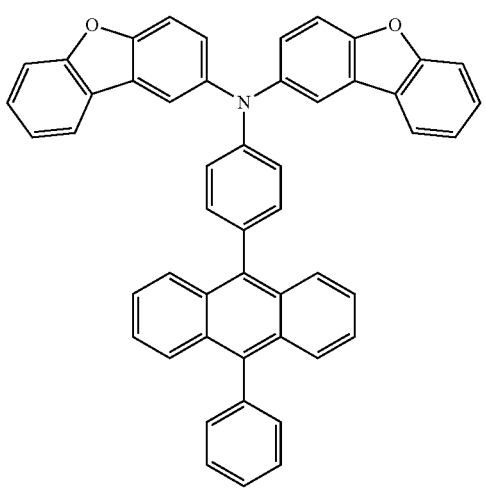
(109)
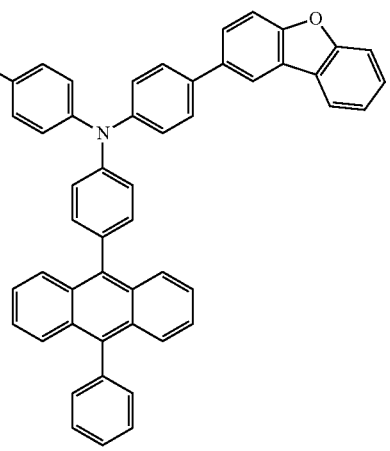

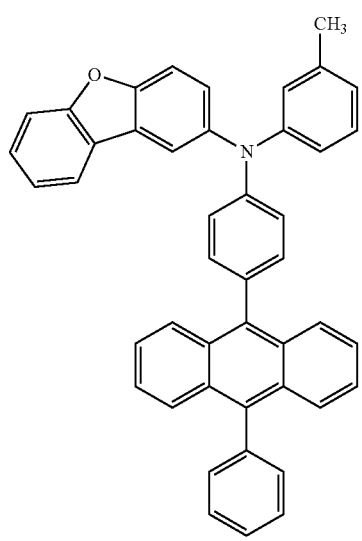
(110)
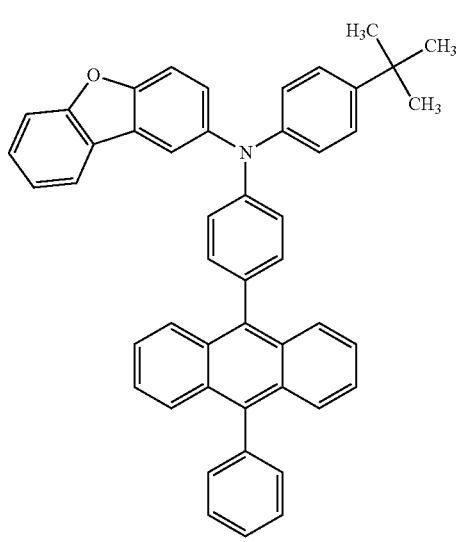
(111)
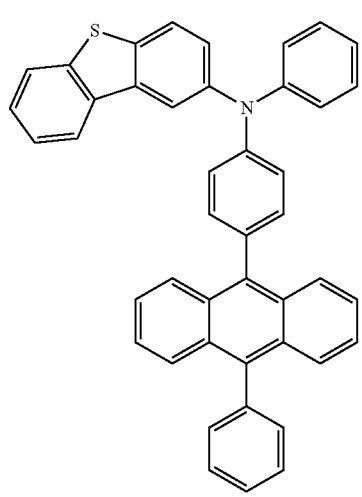
(112)
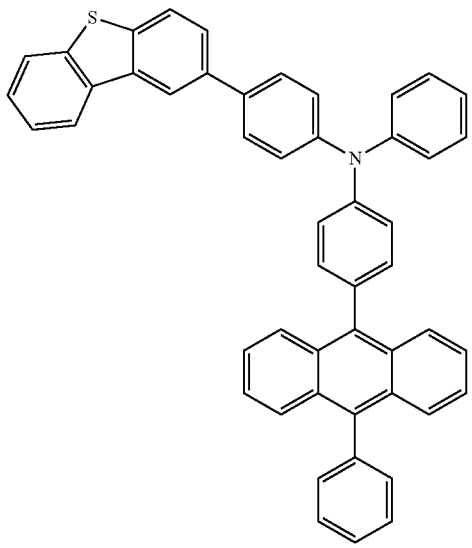
(113)
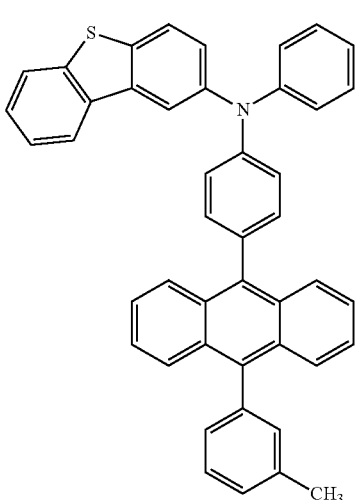
(114)
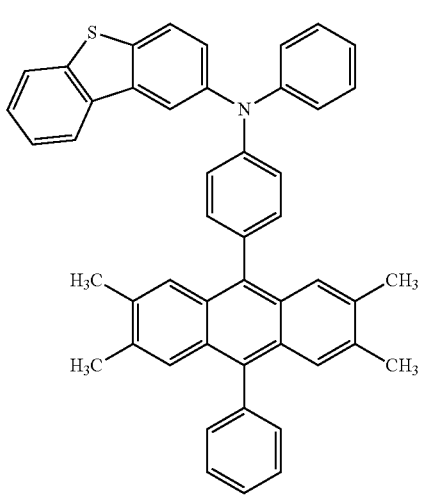
(115)
In addition, an organic compound used for the synthesis of the anthracene compound described in this embodiment is also a novel material; therefore, the organic compound is also included in one embodiment of the present invention.

Thus, another embodiment of the present invention is an organic compound represented by a structural formula (B-1-1).

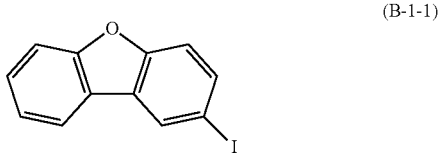 [SMILES: Ic1ccc2oc3ccccc3c2c1]

(B-1-1)

Another embodiment of the present invention is an organic compound represented by a structural formula (B-2-1).

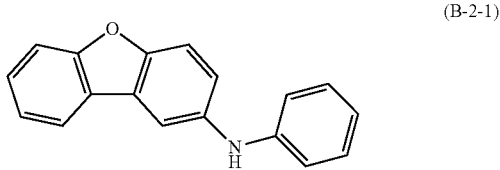

(B-2-1)

Another embodiment of the present invention is an organic compound represented by a structural formula (C-1-1).

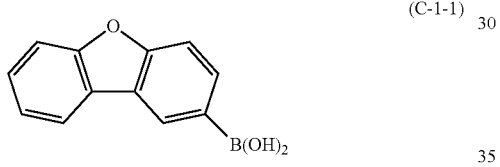

(C-1-1)

Another embodiment of the present invention is an organic compound represented by a structural formula (C-2-1).

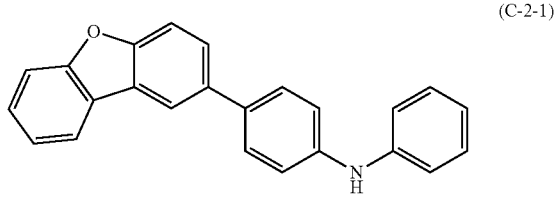 [SMILES: c1ccc(Nc2ccc(-c3ccc4oc5ccccc5c4c3)cc2)cc1]

(C-2-1)

Another embodiment of the present invention is an organic compound represented by a structural formula (D-2-1).

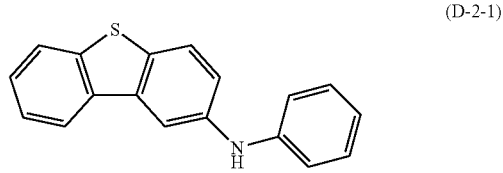 [SMILES: c1ccc(Nc2ccc3sc4ccccc4c3c2)cc1]

(D-2-1)

A variety of reactions can be applied to a method for synthesizing the anthracene compound of this embodiment. For example, the anthracene compound represented by the general formula (G1), which is one embodiment of the present invention, can be synthesized by performing synthesis reaction described below. Note that the methods of synthesizing the anthracene compound which is one embodiment of the present invention are not limited to the synthesis methods below.

[Method 1 of Synthesizing Anthracene Compound Represented by General Formula (G1)]

First, as shown in a synthesis scheme (A-1), a dibenzofuran compound or a dibenzothiophene compound (a1) is halogenated, so that a halogenated dibenzofuran compound or a halogenated dibenzothiophene compound (a2) is obtained.

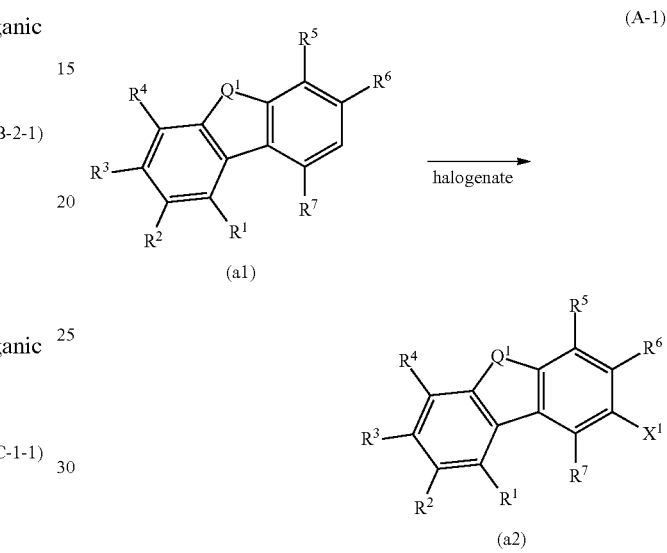

Note that in synthesis scheme (A-1), $Q^1$ represents an oxygen atom or a sulfur atom, and $R^1$ to $R^7$ separately represent any one of a hydrogen atom, an alkyl group having 1 to 6 carbon atoms, a substituted or unsubstituted phenyl group, and a substituted or unsubstituted biphenyl group.

In the scheme, $X^1$ represents a halogen, and as a halogen, chlorine, bromine, or iodine is preferably used. For synthesis at lower cost, bromine is preferably used, and chlorine is more preferably used. In addition, for higher activation of a halogen group of the halogenated dibenzofuran compound or the halogenated dibenzothiophene compound (a2) which is generated, bromine is preferably used, and iodine is more preferably used. The activity of the halogen group of the halogenated dibenzofuran compound or the halogenated dibenzothiophene compound (a2) is preferably increased, because in which case the reactivity in the subsequent reactions is increased.

Note that examples of a halogenating agent that can be used include a mixture of iodine and orthoperiodic acid, and bromine. When a mixture of iodine and orthoperiodic acid is used, sulfuric acid can be used as a reaction accelerator, and glacial acetic acid can be used as a solvent. When bromine is used, chloroform, dichloromethane, carbon tetrachloride, or the like can be used as a solvent.

Next, as shown in a synthesis scheme (A-2), the halogenated dibenzofuran compound or the halogenated dibenzothiophene compound (a2) is lithiated or made as a Grignard reagent, and then reacted with a borate ester, so that a 2-boron compound of dibenzofuran or a 2-boron compound of dibenzothiophene (a3) can be obtained.

(A-2)

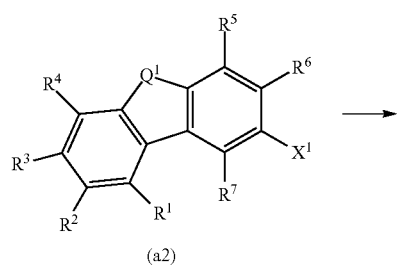

(a2)

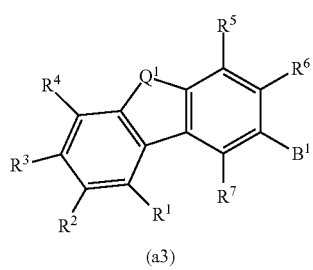

(a3)

Note that in the synthesis scheme (A-2), Q¹ represents an oxygen atom or a sulfur atom, $R^1$ to $R^7$ separately represent any one of a hydrogen atom, an alkyl group having 1 to 6 carbon atoms, a substituted or unsubstituted phenyl group, and a substituted or unsubstituted biphenyl group. In addition, $X^1$ represents a halogen, and as a halogen, chlorine, bromine, or iodine is preferably used. Further, $B^1$ represents boronic acid or dialkoxyboron.

Examples of a reagent that can be used as a lithiating agent include alkyllithium reagents such as n-butyllithium, tert-butyllithium, and methyllithium. Examples of a Grignard reagent include magnesium that is activated by ethylene bromide or the like. Examples of a solvent include a dehydrating solvent, like an ether such as diethyl ether or tetrahydrofuran (THF).

Next, as shown in a synthesis scheme (A-3), the 2-boron compound of dibenzofuran or the 2-boron compound of dibenzothiophene (a3) and a dihalogenated arene (a4) are subjected to a coupling reaction using a metal catalyst in the presence of a base, so that a halogenated dibenzofuran boron compound or a halogenated dibenzothiophene boron compound (a5) is obtained.

(A-3)

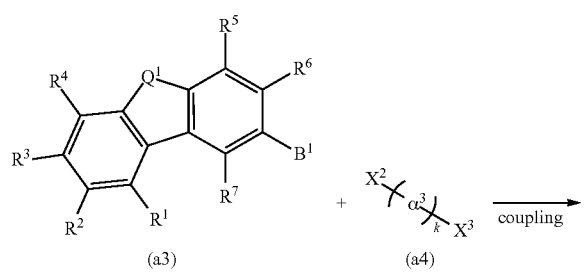

-continued

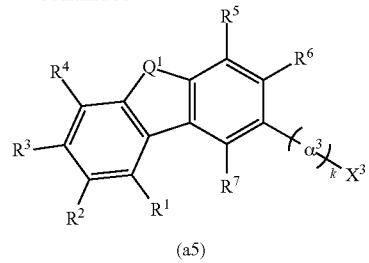

(a5)

Note that in the synthesis scheme (A-3), $Q^1$ represents an oxygen atom or a sulfur atom, $R^1$ to $R^7$ separately represent any one of a hydrogen atom, an alkyl group having 1 to 6 carbon atoms, a substituted or unsubstituted phenyl group, and a substituted or unsubstituted biphenyl group. In addition, $\alpha^3$ represents a substituted or unsubstituted phenylene group.

In the synthesis scheme (A-3), $X^2$ and $X^3$ of the dihalogenated arene (a4) each represent a halogen, and as a halogen, chlorine, bromine, or iodine is preferably used. For higher reactivity, bromine is preferably used, and iodine is more preferably used.

In order to cause reaction of $B^1$ of the 2-boron compound of dibenzofuran or of the 2-boron compound of dibenzothiophene (a3) and $X^2$ of the dihalogenated arene (a4) more selectively, $X^2$ is preferably a halogen with higher reactivity than $X^3$. For example, when $X^3$ is a chlorine atom, $X^2$ is preferably a bromine atom or an iodine atom, and when $X^3$ is a bromine atom, $X^2$ is preferably an iodine atom. As a result, the generation of a by-product due to reaction of $B^1$ of the 2-boron compound of dibenzofuran or of the 2-boron compound of dibenzothiophene (a3) with both $X^2$ and $X^3$ can be reduced.

When the Suzuki-Miyaura reaction in the synthesis scheme (A-3) is carried out, examples of a palladium catalyst that can be used include palladium(II) acetate, tetrakis(triphenylphosphine)palladium(0), bis(triphenylphosphine)palladium(II) dichloride, and the like. In addition, examples of a ligand of the palladium catalyst that can be used include tri(ortho-tolyl)phosphine, triphenylphosphine, tricyclohexylphosphine, and the like. In addition, examples of a base that can be used include organic bases such as sodium tert-butoxide (abbreviation: tert-BuONa), inorganic bases such as a potassium carbonate and a sodium carbonate, and the like. Examples of a solvent that can be used include, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. Further, a mixed solvent of toluene and water; a mixed solvent of toluene, ethanol, and water; or a mixed solvent of ether such as ethylene glycol dimethyl ether and water is more preferable.

In the reaction shown in the synthesis scheme (A-3), cross coupling reactions may be used which employ organoaluminum, organozirconium, organozinc, organotin compounds, or the like, besides the boron compound. Furthermore, in this coupling, a triflate group or the like may be used besides a halogen.

A by-product generated by reaction of two 2-boron compounds of dibenzofuran or two 2-boron compounds of dibenzothiophene (a3) with one dihalogenated arene (a4) has a higher molecular weight than the objective halogenated dibenzofuran boron compound or halogenated dibenzothiophene boron compound (a5), and thus can be separated easily by column purification. In addition, this by-product has no active site, and thus will not react with other compounds in the subsequent reactions to produce any further by-products. Therefore, it is also possible to remove this by-product from compounds in which this by-product is mixed, after the subsequent reactions.

Next, as shown in a synthesis scheme (A-4), the halogenated dibenzofuran boron compound or the halogenated dibenzothiophene boron compound (a5) and an arylamine compound (a6) are subjected to a coupling reaction, so that a diarylamine compound (a7) is obtained.

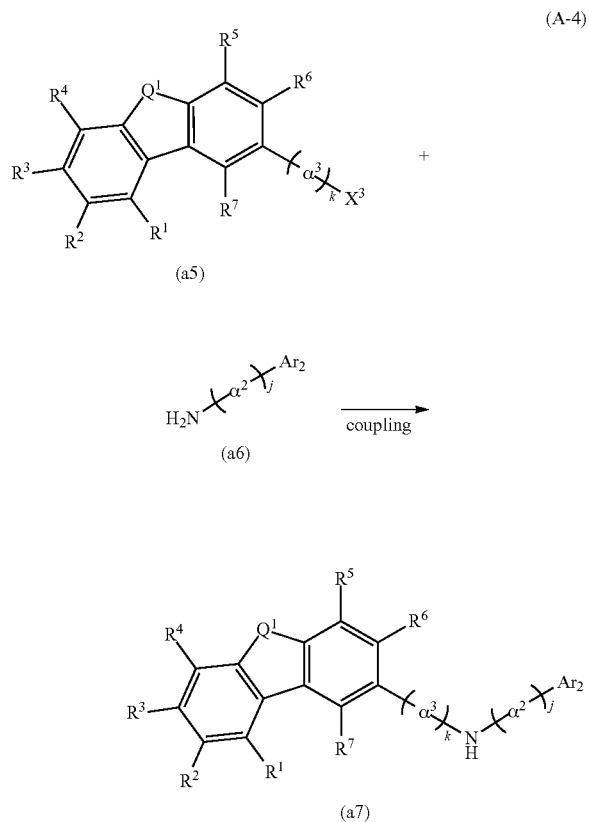

In the synthesis scheme (A-4), $Q^1$ represents an oxygen atom or a sulfur atom, $R^1$ to $R^7$ separately represent any one of a hydrogen atom, an alkyl group having 1 to 6 carbon atoms, a substituted or unsubstituted phenyl group, and a substituted or unsubstituted biphenyl group. In addition, $\alpha^2$ and $\alpha^3$ separately represent a substituted or unsubstituted phenylene group. $Ar_2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1. In addition, $X^3$ represents a halogen, and as a halogen, chlorine, bromine, or iodine is preferably used. Note that for higher reactivity, bromine is preferably used, and iodine is more preferably used.

When a substituent represented by $Ar^2$ is the general formula (Ar2-2) above, it is more preferable that j be 1 and $\alpha^2$ be a paraphenylene group, i.e., the structural formula ($\alpha$-1). In addition, it is preferable that $Q^1$ in the general formula (G1) and $Q^2$ in the general formula (Ar2-2) be the same elements, and when these heterocycles have substituents, it is more preferable that the heterocycle including $Q^1$ and the heterocycle including $Q^2$ have the same substituents at the same position (e.g., $R^5$ and $R^{25}$, or $R^6$ and $R^{26}$). The above manner is even more preferable, because in which case coupling reactions of a heterocycle including $Q^1$ (a dibenzofuranyl group or a dibenzothiophenyl group) and a diphenylamine compound, and of a heterocycle including $Q^2$ and the diphenylamine compound can be concurrently performed; thus, the synthesis becomes easier.

For easier synthesis, it is even more preferable that the heterocycle including $Q^1$ and the heterocycle including $Q^2$ be unsubstituted.

In the synthesis scheme (A-4), a variety of reaction conditions can be employed in the coupling reaction of an aryl compound having a halogen group and an aryl compound having amine (a primary arylamine compound); for example, a synthesis method using a metal catalyst in the presence of a base can be employed.

The case where a Hartwig-Buchwald reaction is performed in the synthesis scheme (A-4) is shown. A palladium catalyst can be used as the metal catalyst, and a mixture of a palladium complex and a ligand thereof can be used as the palladium catalyst. Examples of the palladium catalyst include bis(dibenzylideneacetone)palladium(0), palladium(II) acetate, and the like. Examples of the ligand include tri(tert-butyl)phosphine, tri(n-hexyl)phosphine, tricyclohexylphosphine, 1,1-bis(diphenylphosphino)ferrocene (abbreviation: DPPF), and the like. Examples of a substance which can be used as the base include an organic base such as sodium-tert-butoxide (abbreviation: tert-BuONa), an inorganic base such as potassium carbonate, and the like. The reaction is preferably performed in a solution, and toluene, xylene, benzene, and the like are given as a solvent that can be used in the reaction. However, the catalyst, ligand, base, and solvent which can be used are not limited thereto. In addition, the reaction is more preferably performed under an inert atmosphere of nitrogen, argon, or the like.

The case where an Ullmann reaction is performed in the synthesis scheme (A-4) is also shown. A copper catalyst can be used as the metal catalyst, such as copper(I) iodide or copper(II) acetate. Examples of a substance that can be used as the base include an inorganic base such as potassium carbonate. The reaction is preferably performed in a solution, and 1,3-dimethyl-3,4,5,6-tetrahydro-2(1H)-pyrimidinone (abbreviation: DMPU), toluene, xylene, benzene, and the like can be given as a solvent that can be used. However, the catalyst, base, and solvent which can be used are not limited thereto. In addition, the reaction is more preferably performed under an inert atmosphere of nitrogen, argon, or the like.

Note that a solvent having a high boiling point such as DMPU or xylene is preferably used because, by an Ullmann reaction, an objective substance can be obtained in a shorter time and in a higher yield when the reaction temperature is higher than or equal to 100° C. DMPU is more preferably used because the reaction temperature is more preferably higher than or equal to 150° C.

Next, as shown in a synthesis scheme (A-5), the diarylamine compound (a7) and a halogenated anthracene compound (a8) are subjected to a coupling reaction, so that the anthracene compound represented by the general formula (G1) is obtained.

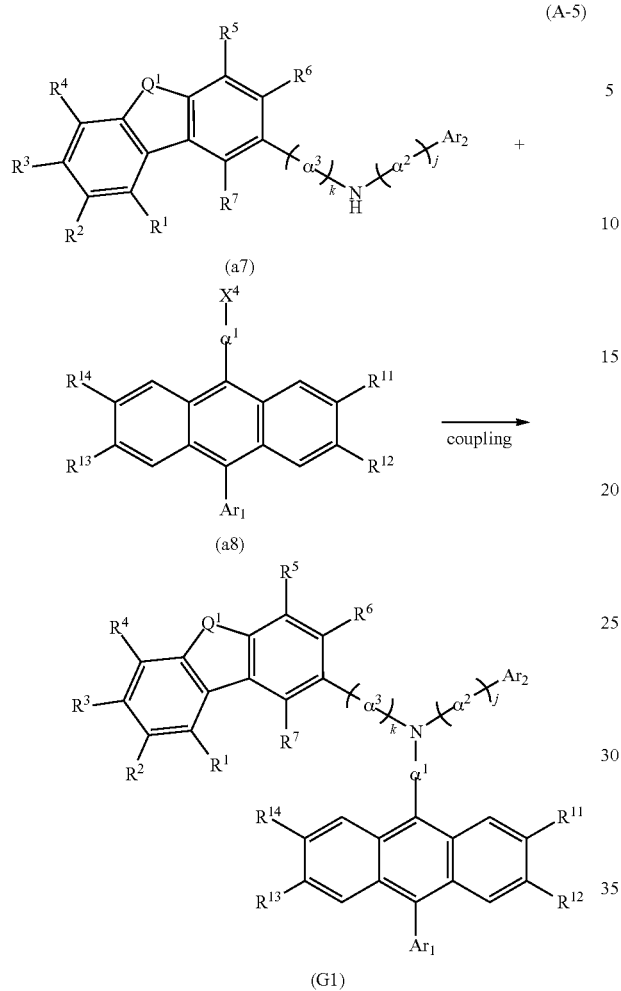

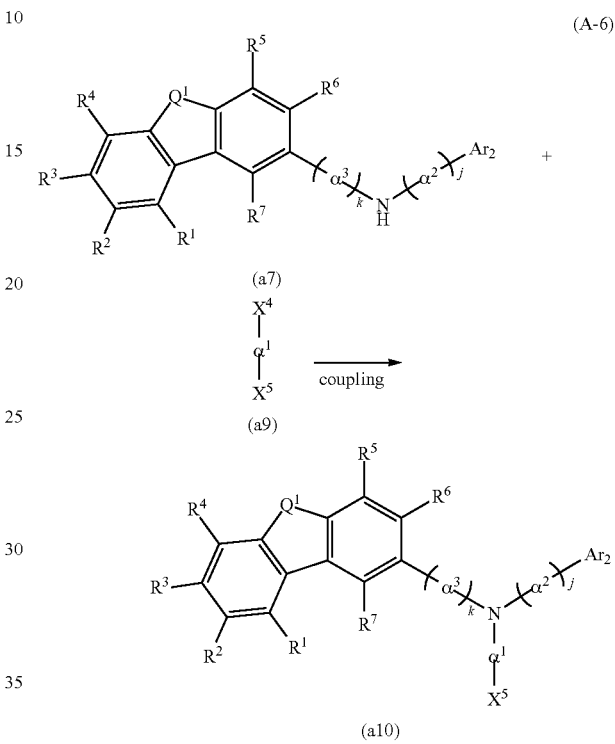

and the halogenated anthracene compound (a8), but this embodiment is not limited to this method.

[Method 2 of Synthesizing Anthracene Compound Represented by General Formula (G1)]

The coupling of the diarylamine compound (a7) and a dihalogenated aryl (a9) can produce a halogenated triarylamine compound (a10).

In the synthesis scheme (A-5), $Q^1$ represents an oxygen atom or a sulfur atom, $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1. In addition, $X^3$ and $X^4$ each represent a halogen, and as a halogen, chlorine, bromine, or iodine is preferably used. For higher reactivity, bromine is preferably used as $X^4$, and iodine is more preferably used as $X^4$.

In the synthesis scheme (A-5), a variety of reaction conditions can be employed in the coupling reaction of an aryl compound having a halogen group and an aryl compound having amine (a secondary arylamine compound); for example, a synthesis method using a metal catalyst in the presence of a base can be employed. The conditions can be similar to those in the synthesis scheme (A-4), and therefore the synthesis scheme (A-4) is referred to for the details.

In the synthesis scheme (A-5) is shown the synthesis of the objective anthracene compound represented by the general formula (G1), by coupling the diarylamine compound (a7)

In a synthesis scheme (A-6), $Q^1$ represents an oxygen atom or a sulfur atom, and $R^1$ to $R^7$ separately represent any one of a hydrogen atom, an alkyl group having 1 to 6 carbon atoms, a substituted or unsubstituted phenyl group, and a substituted or unsubstituted biphenyl group. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1.

In this case, $X^4$ and $X^5$ of the dihalogenated aryl (a9) each represent a halogen, and as a halogen, chlorine, bromine, or iodine is preferably used. For higher reactivity, bromine is preferably used, and iodine is more preferably used. In addition, in order to cause reaction of the diarylamine compound (a7) and $X^4$ of the dihalogenated aryl (a9) more selectively, bromine is preferably used as $X^4$, and iodine is more preferably used as $X^4$, in terms of high reactivity.

In the synthesis scheme (A-6), a variety of reaction conditions can be employed in the coupling reaction of an aryl compound having a halogen group and an aryl compound having amine (a secondary arylamine compound); for example, a synthesis method using a metal catalyst in the presence of a base can be employed. The conditions can be similar to those in the synthesis scheme (A-4), and therefore the synthesis scheme (A-4) is referred to for the details.

Next, as shown in a synthesis scheme (A-7), a halogenated triarylamine compound (a11) and an anthracene boron compound (a12) are subjected to a coupling reaction, so that the anthracene compound represented by the general formula (G1) is obtained.

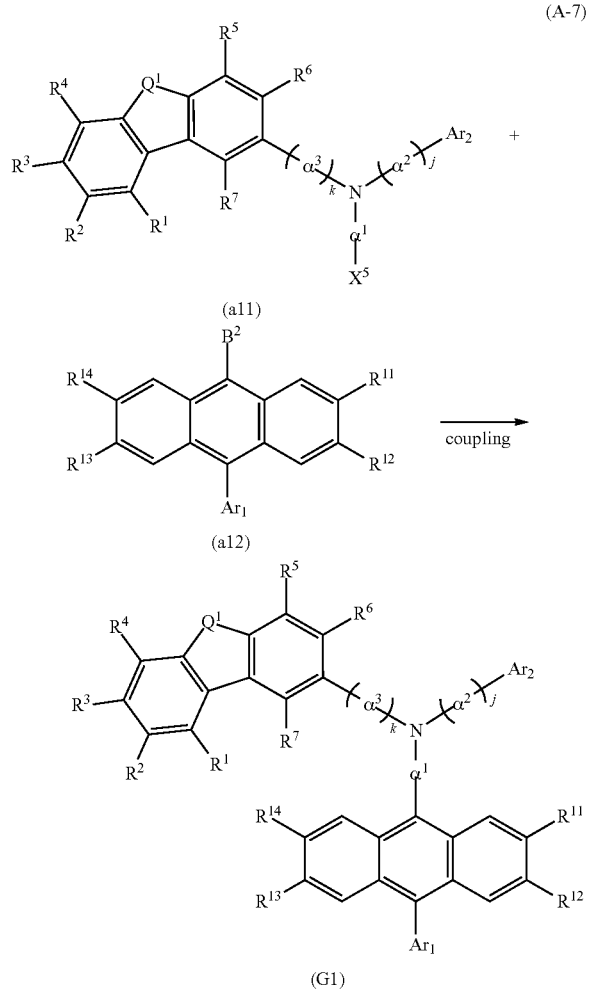

In the synthesis scheme (A-7), $Q^1$ represents an oxygen atom or a sulfur atom. $B^2$ represents boronic acid or dialkoxyboron. $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group. $Ar^1$ represents a substituted or unsubstituted condensed aromatic hydrocarbon having 6 to 12 carbon atoms forming a ring. $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1.

In the coupling reaction in the synthesis scheme (A-7), a variety of reaction conditions can be employed; for example, a synthesis method using a metal catalyst in the presence of a base can be employed.

In the synthesis scheme (A-7), a variety of reaction conditions can be employed in the coupling reaction of an aryl compound having a halogen group and an aryl boron compound; for example, a synthesis method using a metal catalyst in the presence of a base can be employed. The conditions can be similar to those in the synthesis scheme (A-3), and therefore the synthesis scheme (A-3) is referred to for the details.

Note that in the synthesis scheme (A-7), the halogen group $X^5$ of the halogenated triarylamine compound (a11) is reacted with the boron compound group $B^2$ of the anthracene boron compound (a12); however, by coupling the halogenated triarylamine compound (a11) as a boron compound and the anthracene boron compound (a12) as a halide (the halogen group $X^5$ and $B^2$ are interchanged), the anthracene compound represented by the general formula (G1) can also be obtained.

The anthracene compound of this embodiment exhibits fluorescence and can emit light having a short wavelength. Thus, with the use of the anthracene compound of this embodiment as a light-emitting material, blue light can be emitted.

The anthracene compound of this embodiment is also suitable as a host material in a light-emitting layer of a light-emitting element. In other words, when a light-emitting substance (hereinafter, also referred to as a dopant material) having a narrower band gap than the anthracene compound of this embodiment is added to a layer containing the anthracene compound, light can be emitted from the dopant material. Since the anthracene compound of this embodiment has a wide band gap, it can be used at least as a host material of a fluorescent compound that emits visible light having a wavelength longer than that of green light.

The anthracene compound of this embodiment has a hole-transport property and thus can be suitably used as a material of a hole-injection layer or a hole-transport layer of a light-emitting element. Further, a composite material in which the anthracene compound of this embodiment (an electron donor) and an electron acceptor are mixed can be used for a hole-injection layer of a light-emitting element. The electron acceptor or the electron donor at least receives or releases electrons by the aid of an electric field.

Note that this embodiment can be implemented in free combination with any of the other embodiments.

Embodiment 2

Embodiment 2 shows a light-emitting element formed using an anthracene compound described in Embodiment 1.

The light-emitting element in Embodiment 2 includes a first electrode which functions as an anode, a second electrode which functions as a cathode, and an EL layer interposed between the first electrode and the second electrode. Note that the light-emitting element in Embodiment 2 can emit light when a voltage is applied to each electrode so that the potential of the first electrode is higher than that of the second electrode.

Figure 1B:
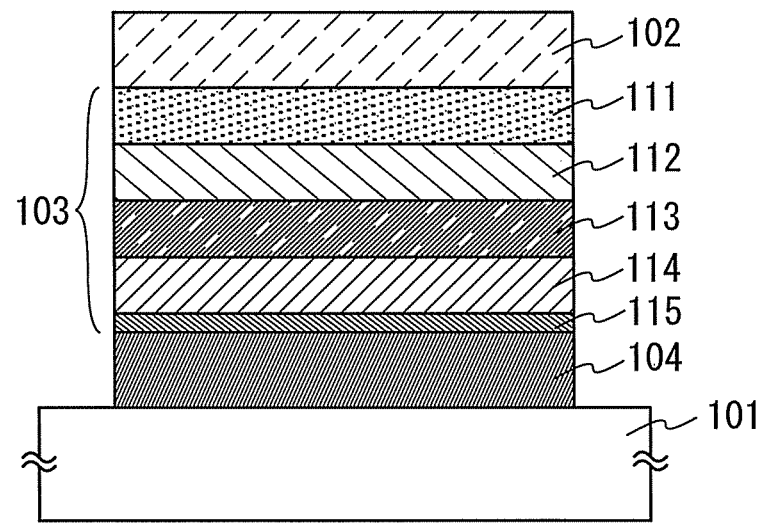

A structure of the light-emitting element in Embodiment 2 is described using FIGS. 1A and 1B. A substrate 101 is used as a support of the light-emitting element. For the substrate 101, glass, quartz, plastics, or the like can be used, for example. Further, a flexible substrate may be used. The flexible substrate is a substrate that can be bent, such as a plastic substrate made of polycarbonate, polyarylate, or polyether sulfone, for example. Alternatively, a film made of polypropylene, polyester, polyvinyl fluoride, polyvinyl chloride, or the like, an inorganic film formed by evaporation, or the like can also be used.

The substrate 101 may remain in a light-emitting device which is a product utilizing the light-emitting element of this embodiment. Alternatively, the substrate 101 may only function as the support of the light-emitting element in its manufacturing process without remaining in an end product.

For a first electrode 102 formed over the substrate 101, a metal, an alloy, an electrically conductive compound, a mixture thereof, or the like which has a high work function (specifically, a work function of 4.0 eV or higher) is preferably used. Specific examples include indium oxide-tin oxide (ITO: indium tin oxide), indium oxide-tin oxide containing silicon or silicon oxide, indium oxide-zinc oxide, indium oxide containing tungsten oxide and zinc oxide, graphene, and the like. Examples further include gold (Au), platinum (Pt), nickel (Ni), tungsten (W), chromium (Cr), molybdenum (Mo), iron (Fe), cobalt (Co), copper (Cu), palladium (Pd), titanium (Ti), nitride of metal materials (for example, titanium nitride), and the like.

These materials are usually deposited by a sputtering method. For example, indium oxide-zinc oxide can be deposited by a sputtering method using a target in which 1 wt % to 10 wt % zinc oxide is added to indium oxide, and indium oxide containing tungsten oxide and Zinc oxide can be deposited by a sputtering method using a target in which 0.5 wt % to 5 wt % tungsten oxide and 0.1 wt % to 1 wt % zinc oxide are added to indium oxide. Alternatively, a vacuum evaporation method, a coating method, an inkjet method, a spin coating method, or the like may be used.

An EL layer 103 is formed over the first electrode 102, and in the EL layer 103, a first layer (hole-injection layer) 111 which is formed in contact with the first electrode 102 is formed using a composite material with which holes are easily injected regardless of the work function of the first electrode 102. Therefore, any of a variety of known materials can be used as long as it can serve as an electrode material (e.g., a metal, an alloy, an electrically conductive compound, a mixture thereof, or an element belonging to Group 1 or 2 of the periodic table).

When a layer containing a composite material described below is used, the first electrode 102 can be formed using any of a variety of metals, alloys, electrically conductive compounds, or a mixture thereof regardless of the work function. For example, aluminum (Al), silver (Ag), an alloy containing aluminum (e.g., AlSi), or the like can be used.

Alternatively, it is possible to use any of elements belonging to Group 1 or Group 2 of the periodic table, that is, alkali metals such as lithium (Li) and cesium (Cs), alkaline earth metals such as magnesium (Mg), calcium (Ca), and strontium (Sr), alloys thereof (e.g., MgAg and AlLi), rare earth metals such as europium (Eu) and ytterbium (Yb), alloys thereof, and the like which have a low work function.

When the first electrode 102 is formed using an alkali metal, an alkaline earth metal, or an alloy thereof, a vacuum evaporation method or a sputtering method can be used. Further alternatively, when a silver paste or the like is used, a coating method, an inkjet method, or the like can be used.

The EL layer 103 formed over the first electrode 102 contains at least the anthracene compound described in Embodiment 1, and the EL layer 103 can be formed using any of other known materials. As the known material, any of low molecular compounds and high molecular compounds can be used. Note that the substance contained in the EL layer 103 is not limited to an organic compound and may partially include an inorganic compound.

The EL layer 103 is formed by stacking an appropriate combination of a hole-injection layer that contains a substance having a high hole-injection property, a hole-transport layer that contains a substance having a high hole-transport property, a light-emitting layer that contains a light-emitting substance, an electron-transport layer that contains a substance having a high electron-transport property, an electron-injection layer that contains a substance having a high electron-injection property, and the like. Note that the EL layer 103 at least includes a light-emitting layer.

Note that the EL layer 103 illustrated in FIG. 1A includes the first layer (hole-injection layer) 111, a second layer (hole-transport layer) 112, a third layer (light-emitting layer) 113, a fourth layer (electron-transport layer) 114, and a fifth layer (electron-injection layer) 115 which are stacked in that order over the first electrode 102.

The first layer (hole-injection layer) 111 is a layer containing a substance having a high hole-injection property. Examples of the substance having a high hole-injection property include molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, and the like. A low molecular organic compound can also be used, like a phthalocyanine-based compound such as phthalocyanine (abbreviation: $H_2Pc$), or copper(II) phthalocyanine (abbreviation: CuPc).

Further, examples of the low molecular organic compound include aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like. In addition, the anthracene compound described in Embodiment 1 can also be used.

Alternatively, any of high molecular compounds (e.g., oligomers, dendrimers, or polymers) can be used. Examples of the high molecular compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine (abbreviation: Poly-TPD). Alternatively, a high molecular compound to which acid is added, such as poly(3,4-ethylene dioxythiophene)/poly(styrene sulfonic acid) (PEDOT/PSS), or polyaniline/poly(styrenesulfonic acid) (PAni/PSS), can be used.

Further alternatively, a composite material formed by mixing an acceptor substance into a substance having a high hole-transport property can also be used for the first layer (hole-injecting layer) 111. Note that, the use of such a material formed by mixing an acceptor substance into a substance having a high hole-transport property enables a material used to form an electrode to be selected regardless of its work function. In other words, besides a material having a high work function, a material having a low work function can also be used for the first electrode 102. Such a composite material can be formed by co-evaporation of a substance having a high hole-transport property and a substance having an acceptor property. Note that, in this specification, the word "composite" means not only a state in which two materials are simply mixed but also a state in which a plurality of materials are mixed and charges are transferred between the materials.

As the organic compound for the composite material, various compounds can be used, such as an aromatic amine compound, carbazole derivatives, aromatic hydrocarbon, or a high molecular compound (such as oligomer, dendrimer, or polymer). The organic compound used for the composite material is preferably an organic compound having a high hole-transport property. Specifically, a substance having a hole mobility of $10^{-6}$ cm$^2$/V·s or higher is preferably used. However, another substance may also be used as long as the hole-transport property is higher than the electron-transport property. The organic compounds which can be used for the composite material are specifically shown below.

Examples of the organic compound that can be used for the composite material include aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Further, examples of the aromatic hydrocarbon compound include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Furthermore, examples of the aromatic hydrocarbon compound include 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, or coronene; and an aromatic hydrocarbon compound having a vinyl group can also be used such as 4,4'-bis(2,2-diphenylvinyl)biphenyl (abbreviation: DPVBi) or 9,10-bis[4-(2,2-diphenylvinyl)phenyl]anthracene (abbreviation: DPVPA). In addition, the anthracene compound described in Embodiment 1 can also be used.

As the acceptor substance that can be used for the composite material, organic compounds such as 7,7,8,8-tetracyano-2,3,5,6-tetrafluoroquinodimethane (abbreviation: F$_4$-TCNQ) and chloranil, and a transition metal oxide can be given. Oxides of metals belonging to Group 4 to Group 8 in the periodic table can also be used. Specifically, vanadium oxide, niobium oxide, tantalum oxide, chromium oxide, molybdenum oxide, tungsten oxide, manganese oxide, and rhenium oxide are preferable due to their high electron-accepting property. Among these, molybdenum oxide is especially preferable since it is stable in the air and its hygroscopic property is low and is easily treated.

Alternatively, for forming the first layer (hole-injection layer) 111, the above-described high molecular compounds, such as PVK, PVTPA, PTPDMA, or Poly-TPD, may be combined with the above-described acceptor substance to form a composite material.

The second layer (hole-transport layer) 112 is a layer containing a substance having a high hole-transport property. Examples of the substance having a high hole-transport property include aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ cm$^2$/V·s or higher. However, another substance may also be used as long as the hole-transport property is higher than the electron-transport property. The anthracene compound described in Embodiment 1 can also be used. The layer containing a substance having a high hole-transport property is not limited to a single layer, and two or more layers containing the aforementioned substances may be stacked.

The second layer (hole-transport layer) 112 may be formed using a carbazole derivative such as CBP, CzPA, or PCzPA or an anthracene derivative such as t-BuDNA, DNA, or DPAnth.

Note that the second layer (hole-transport layer) 112 can also be formed using a high molecular compound such as poly(N-vinylcarbazole) (abbreviation: PVK) or poly(4-vinyltriphenylamine) (abbreviation: PVTPA).

The third layer (light-emitting layer) 113 is a layer containing a substance having a high light-emitting property. In this embodiment, the third layer (light-emitting layer) 113 contains the anthracene compound described in Embodiment 1 as a light-emitting substance.

The third layer (light-emitting layer) 113 may have a structure in which the anthracene compound described in Embodiment 1 is contained as a main component, or dispersed as a dopant material in another substance (host material). Note that in the case of the dispersing, the concentration of the anthracene compound described in Embodiment 1 is preferably 10% or less of the total in mass ratio. A known substance can be used as the host material; it is preferable to use a substance whose lowest unoccupied molecular orbital level (LUMO level) is shallower (the absolute value is smaller) and highest occupied molecular orbital level (HOMO level) is deeper (the absolute value is larger) than those of the anthracene compound described in Embodiment 1. In addition, the host material preferably has a higher S1 level than the anthracene compound described in Embodiment 1.

Alternatively, a heterocyclic compound can be used, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(biphenyl-4-yl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), or bathocuproine (abbreviation: BCP).

Further alternatively, a condensed aromatic compound can be used, such as 9-[4-(N-carbazolyl)phenyl]-10-phenylanthracene (abbreviation: CzPA), 9-[4-(3,6-diphenyl-N-carbazolyl)phenyl]-10-phenylanthracene (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), or 3,3',3''-(benzene-1,3,5-triyl)tripyrene (abbreviation: TPB3).

As a substance in which the light-emitting substance is dispersed, plural kinds of substances can be used. For example, in order to suppress crystallization, a substance such as rubrene which suppresses crystallization, may be further added. In addition, a substance having a high hole-transport property, a substance having a high electron-transport property, or the like can be further added in order to efficiently transfer energy to the light-emitting substance. With a structure in which a light-emitting substance is thus dispersed in another substance, crystallization of the third layer (light-emitting layer) 113 can be suppressed. Further, concentration quenching which results from the high concentration of the light-emitting compound can also be suppressed.

It is especially preferable that, among the above-described substances, a substance having an electron-transport property be used so that the anthracene compound described in Embodiment 1 is dispersed therein to form the third layer (light-emitting layer) 113. Specifically, it is possible to use CzPA, DNA, or t-BuDNA among the above-described metal complexes, heterocyclic compounds, and condensed aromatic compounds, and furthermore, high molecular compounds to be given later as a substance which can be used for the fourth layer (electron-transport layer) 114.

This embodiment shows an example of using the anthracene compound described in Embodiment 1 as a light-emitting substance; however, embodiments of the present invention are not limited thereto. Since the anthracene compound described in Embodiment 1 has a wide band gap, it can be used at least as a host material of a fluorescent compound that emits visible light having a wavelength longer than that of green light.

Specific examples of a material that emits green light include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Examples of a material that emits yellow light include rubrene, 5,12-bis(1,1'-biphenyl-4-yl)-6,11-diphenyltetracene (abbreviation: BPT), and the like. Furthermore, examples of a material that emits red light include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

Note that the third layer (light-emitting layer) 113 can be formed using two or more layers. For example, in the case where the third layer (light-emitting layer) 113 is formed by stacking a first light-emitting layer and a second light-emitting layer in that order from the hole-transport layer side, the first light-emitting layer can be formed using a substance having a hole-transport property as a host material and the second light-emitting layer can be formed using a substance having an electron-transport property as a host material. It is more preferable that the first light-emitting layer be formed using a material in which the hole-transport property is higher than the electron-transport property as a host material and the second light-emitting layer be formed using a material in which the electron-transport property is higher than the hole-transport property as a host material. With the above structure, a light emission region is formed between the first light-emitting layer and the second light-emitting layer, whereby an element having higher efficiency can be obtained.

When the light-emitting layer having the structure described above is formed using a plurality of materials, the light-emitting layer can be formed using co-evaporation by a vacuum evaporation method; or an inkjet method, a spin coating method, a dip coating method, or the like using a solution of the materials.

The fourth layer (electron-transport layer) 114 is a layer containing a substance having a high electron-transport property. The fourth layer (electron-transport layer) 114 can be formed using, for example, a metal complex such as Alq, Almq$_3$, BeBq$_2$, BAlq, Znq, ZnPBO, or ZnBTZ, or the like as a low molecular organic compound. Alternatively, instead of the metal complex, a heterocyclic compound such as PBD, OXD-7, TAZ, TPBI, BPhen, or BCP can be used. The substances mentioned here are mainly ones that have an electron mobility of $10^{-6}$ cm$^2$/V·s or higher. Further, another substance may also be used for the electron-transport layer as long as the electron-transport property is higher than the hole-transport property. Furthermore, the electron-transport layer is not limited to a single layer, and two or more layers formed using the above-described substances may be stacked.

Alternatively, the fourth layer (electron-transport layer) 114 can be formed using a high molecular compound. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), or the like can be used.

The fifth layer (electron-injection layer) 115 is a layer containing a substance having a high electron-injection property. The fifth layer (electron-injection layer) 115 can be foamed using an alkali metal, an alkaline earth metal, or a compound thereof, such as lithium fluoride (LiF), cesium fluoride (CsF), or calcium fluoride (CaF$_2$). Alternatively, a layer containing an electron-transport substance and an alkali metal, an alkaline earth metal, or a compound thereof, specifically, a layer containing Alq and magnesium (Mg), or the like may be used. Note that in this case, electrons can be more efficiently injected from a second electrode 104.

The second electrode 104 is preferably formed using a metal, an alloy, an electrically conductive compound, or a mixture thereof, having a low work function (specifically, a work function of 3.8 eV or lower). Specific examples of such a cathode material include an element belonging to Group 1 or 2 of the periodic table, i.e., an alkali metal such as lithium (Li) or cesium (Cs), an alkaline earth metal such as magnesium (Mg), calcium (Ca), or strontium (Sr), an alloy containing any of these metals (such as an MgAg alloy or an AlLi alloy), a rare-earth metal such as europium (Eu) or ytterbium (Yb), an alloy containing such rare-earth metals, and the like.

Note that in the case where the second electrode 104 is formed using an alkali metal, an alkaline-earth metal, or an alloy thereof, a vacuum evaporation method or a sputtering method can be used. Alternatively, in the case of using a silver paste or the like, a coating method, an inkjet method, or the like can be used Note that with the fifth layer (electron-injection layer) 115 provided, the second electrode 104 can be formed using any of a variety of electrically conductive materials such as Al, Ag, ITO, graphene, and indium oxide-tin oxide containing silicon or silicon oxide regardless of their work functions.

Such an electrically conductive material can be deposited by a sputtering method, an inkjet method, a spin coating method, or the like.

Further, as a formation method of the EL layer 103 in which the first layer (hole-injection layer) 111, the second layer (hole-transport layer) 112, the third layer (light-emitting layer) 113, the fourth layer (electron-transport layer) 114, and the fifth layer (electron-injection layer) 115 are stacked in that order, any of a variety of methods can be employed regardless of whether the method is a dry process or a wet process. For example, a vacuum evaporation method, an inkjet method, a spin coating method, or the like can be used. Note that a different formation method may be employed for each layer.

The second electrode 104 can also be formed by a wet process using a paste of a metal material instead of a dry process such as a sputtering method or a vacuum evaporation method.

Since holes mainly flow between the first electrode 102 and the first layer (hole-injection layer) 111, between the first layer (hole-injection layer) 111 and the second layer (hole-transport layer) 112, and between the second layer (hole-transport layer) 112 and the third layer (light-emitting layer) 113, the HOMO levels (work function in a case of metal) thereof are preferably the same or almost the same to reduce the carrier injection barrier between the adjacent layers. Similarly, since electrons mainly flow between the third layer (light-emitting layer) 113 and the fourth layer (electron-transport layer) 114, between the fourth layer (electron-transport layer) 114 and the fifth layer (electron-injection layer) 115, and between the fifth layer (electron-injection layer) 115 and the second electrode 104, the LUMO levels (work function in a case of metal) thereof are preferably the same or almost the same to reduce the carrier injection barrier between the adjacent layers. The difference is preferably less than or equal to 0.2 eV, more preferably less than or equal to 0.1 eV.

Further, it is preferable to confine carriers in the light-emitting layer by increasing a difference in HOMO level between the second layer (hole-transport layer) 112 and the third layer (light-emitting layer) 113 or a difference in LUMO level between the third layer (light-emitting layer) 113 and the fourth layer (electron-transport layer) 114 so that a light-emitting element with higher efficiency can be obtained. Note that in this case, if the barrier is too high, the driving voltage increases to be a burden on the element. Therefore, each of the differences is preferably less than or equal to 0.4 eV, more preferably less than or equal to 0.2 eV.

In the light-emitting element of this embodiment, current flows due to potential difference between the first electrode 102 and the second electrode 104, holes and electrons recombine in the EL layer 103, an organic compound having a light-emitting property is brought into an excited state, and when the excited state relaxes to a ground state, the light-emitting organic compound releases the relaxation energy as light emission. Then, this emitted light is extracted out through one or both of the first electrode 102 and the second electrode 104. Accordingly, one or both of the first electrode 102 and the second electrode 104 has/have a light-transmitting property.

Figure 2A:
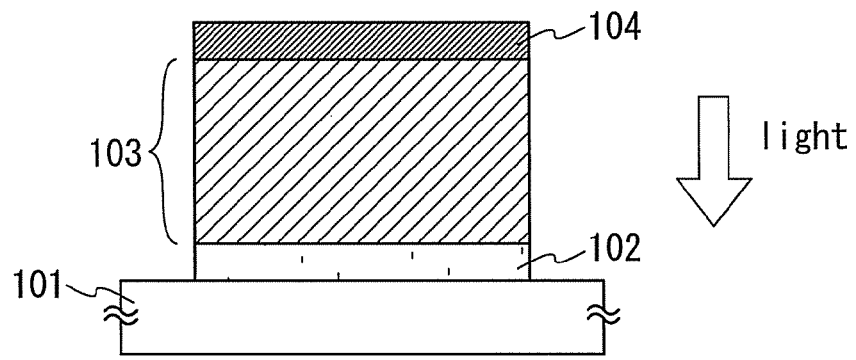
FIGS. 2A to 2C illustrate light-emitting elements according to embodiments of the present invention.
Figure 2B:
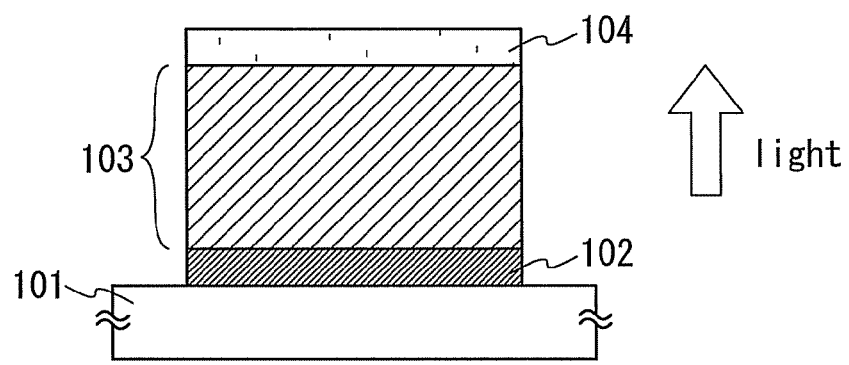
Figure 2C:
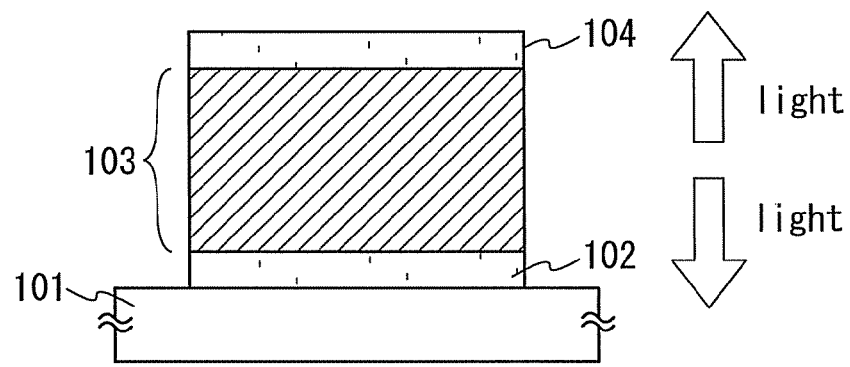

When only the first electrode 102 has a light-transmitting property, as illustrated in FIG. 2A, the emitted light from the EL layer 103 is extracted from the substrate 101 side through the first electrode 102. Alternatively, when only the second electrode 104 has a light-transmitting property, as illustrated in FIG. 2B, the emitted light from the EL layer 103 is extracted from the side opposite to the substrate 101 through the second electrode 104. Further, when each of the first electrode 102 and the second electrode 104 has a light-transmitting property, as illustrated in FIG. 2C, the emitted light from the EL layer 103 is extracted from both the substrate 101 side and the side opposite to the substrate 101 side through the first electrode 102 and the second electrode 104.

The structure of the layers provided between the first electrode 102 and the second electrode 104 is not limited to the above-described one. Structures other than the above may be employed as long as at least the second layer (hole-transport layer) 112 which is a hole-transport layer and the third layer (light-emitting layer) 113 which is a light-emitting layer are included.

Alternatively, as illustrated in FIG. 1B, a structure may be employed in which the second electrode 104 functioning as a cathode, the EL layer 103, and the first electrode 102 functioning as an anode are stacked in that order over the substrate 101. In this case, the EL layer 103 has a structure in which the fifth layer (electron-injection layer) 115, the fourth layer (electron-transport layer) 114, the third layer (light-emitting layer) 113, the second layer (hole-transport layer) 112, the first layer (hole-injection layer) 111, and the first electrode 102 are stacked in that order over the second electrode 104.

Note that by use of the light-emitting element of this embodiment, a passive matrix light-emitting device or an active matrix light-emitting device in which drive of the light-emitting element is controlled by a thin film transistor (TFT) can be fabricated.

Note that there is no particular limitation on the structure of the TFT in the case of fabricating an active matrix light-emitting device. For example, a staggered TFT or an inverted staggered TFT can be used as appropriate. Further, a driver circuit formed over a TFT substrate may be formed using both of an n-channel TFT and a p-channel TFT or only either an n-channel TFT or a p-channel TFT. Furthermore, there is no particular limitation on the crystallinity of a semiconductor film used for the TFT. An amorphous semiconductor film may be used, or a crystalline semiconductor film may be used.

In the above-described manner, the light-emitting element described in this embodiment contains the anthracene compound of Embodiment 1; therefore, element efficiency can be improved and a long lifetime can be achieved.

Embodiment 3

Embodiment 3 shows a mode of a light-emitting element having a structure in which a plurality of light-emitting units (also referred to as EL layers) are stacked (hereinafter, referred to as a stacked-type element) with reference to FIGS. 3A and 3B. The light-emitting element is a stacked-type light-emitting element including a plurality of light-emitting units between a first electrode and a second electrode. Each light-emitting unit can have a structure similar to the structure of the EL layer described in Embodiment 2. In other words, the light-emitting element described in Embodiment 2 is a light-emitting element having one light-emitting unit. Embodiment 3 shows a light-emitting element having a plurality of light-emitting units.

Figure 3A:
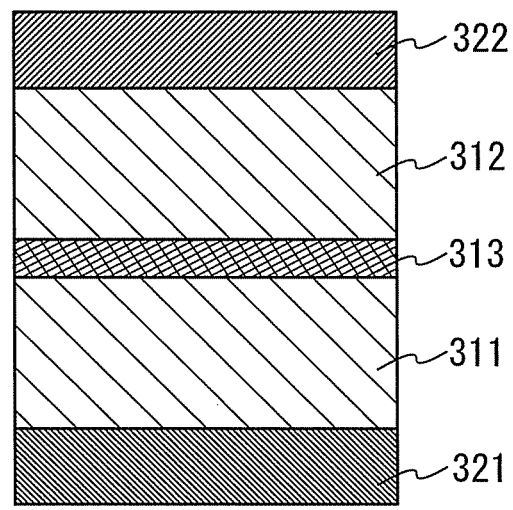
FIGS. 3A and 3B illustrate light-emitting elements according to embodiments of the present invention.

In FIG. 3A, a first light-emitting unit 311 and a second light-emitting unit 312 are stacked between a first electrode 321 and a second electrode 322. The first electrode 321 and the second electrode 322 can be similar to the electrodes shown in Embodiment 2. The first light-emitting unit 311 and the second light-emitting unit 312 may have the same structure or different structures, which can be similar to that described in Embodiment 2.

A charge generation layer 313 functions such that electrons are injected into one light-emitting unit and holes are injected into the other light-emitting unit by application of a voltage between the first electrode 321 and the second electrode 322. That is, the charge generation layer 313 may have either a structure containing an organic compound having a high hole-transport property and an electron acceptor (an acceptor) or a structure containing an organic compound having a high electron-transport property and an electron donor (a donor). The charge generation layer 313 may have a single layer structure or a stack structure of a plurality of layers. As the stack structure of a plurality of layers, a structure in which a hole-injection layer and an electron-injection layer are stacked is preferable.

As the hole-injection layer, a semiconductor or an insulator, such as molybdenum oxide, vanadium oxide, rhenium oxide, or ruthenium oxide, can be used. Alternatively, the hole-injection layer may have a structure in which an acceptor substance is added to a substance having a high hole-transport property. A layer containing a substance having a high hole-transport property and an acceptor substance contains, as an acceptor substance, 7,7,8,8-tetracyano-2,3,5,6-tetrafluoro-quinodimethane (abbreviation: $F_4$-TCNQ) or metal oxide such as vanadium oxide, molybdenum oxide, or tungsten oxide. As the substance having a high hole-transport property, any of a variety of compounds can be used such as an aromatic amine compound, a carbazole derivative, aromatic hydrocarbon, a high molecular compound, oligomer, dendrimer, polymer, and the like. The anthracene compound described in Embodiment 1 of the present invention can also be used similarly. Note that a substance having a hole mobility of $10^{-6}$ $cm^2/V \cdot s$ or higher is preferably employed as the substance having a high hole-transport property. Further, another material may also be used as long as the hole-transport property is higher than the electron-transport property. The composite material containing the substance having a high hole-transport property and the acceptor substance is excellent in a carrier-injection property and a carrier-transport property. Therefore, low-voltage driving and low-current driving can be achieved.

The electron-injection layer can be formed using an insulator such as lithium oxide, lithium fluoride, or cesium carbonate, or a semiconductor. Alternatively, the electron-injection layer may have a structure in which a donor substance is added to a substance having a high electron-transport property. As the donor substance, it is possible to use an alkali metal, an alkaline-earth metal, a rare-earth metal, a metal that belongs to Group 13 of the periodic table, or an oxide or carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the donor substance. Note that a substance having an electron mobility of $10^{-6}$ $cm^2/V \cdot s$ or higher is preferably used as the substance having a high electron-transport property. Further, another material may also be used as long as the electron-transport property is higher than the hole-transport property. Since the composite material of the substance having a high electron-transport property and the donor substance has an excellent carrier-injection property and an excellent carrier-transport property, low-voltage driving and low-current driving can be achieved.

Alternatively, the charge generation layer 313 can be formed using the electrode materials described in Embodiment 2. For example, the charge generation layer 313 may be formed by combining a layer containing a substance having a high hole-transport property and metal oxide with a transparent electrically conductive film. It is preferable that the charge generation layer be a highly light-transmitting layer in view of light extraction efficiency.

In any case, the charge generation layer 313 interposed between the first light-emitting unit 311 and the second light-emitting unit 312 may have any structure as long as electrons are injected into one of the light-emitting units and holes are injected into the other of the light-emitting units by application of a voltage between the first electrode 321 and the second electrode 322. For example, the charge generation layer 313 may have any structure as long as electrons are injected into the first light-emitting unit 311 and holes are injected into the second light-emitting unit 312 by application of a voltage such that the potential of the first electrode is higher than that of the second electrode.

Figure 3B:
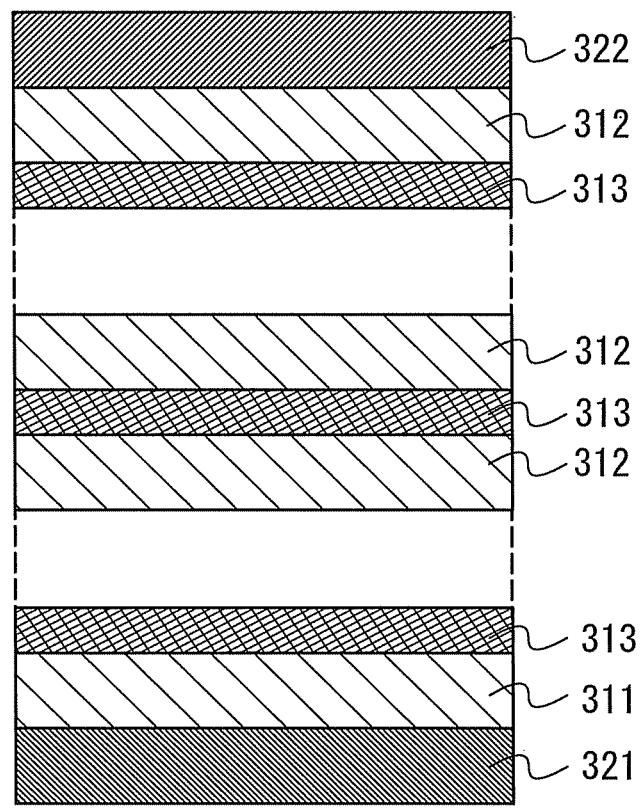

This embodiment shows the light-emitting element having two light-emitting units; however, an embodiment of the present invention can be similarly applied to a light-emitting element in which three or more light-emitting units are stacked as illustrated in FIG. 3B. A plurality of light-emitting units which are partitioned by the charge generation layer are arranged between a pair of electrodes, as in the light-emitting element of this embodiment, whereby the element can emit light in a high luminance region while current density is kept low. Since current density can be kept low, the element can have a long lifetime. When the light-emitting element is applied for illumination, voltage drop due to resistance of an electrode material can be reduced, thereby achieving homogeneous light emission in a large area. Moreover, a light-emitting device of low power consumption, which can be driven at a low voltage, can be achieved.

The light-emitting units emit light having different colors from each other, thereby obtaining light emission of a desired color as the whole light-emitting element. For example, in a light-emitting element having two light-emitting units, the emission colors of the first light-emitting unit and the second light-emitting unit are made complementary, so that the light-emitting element which emits white light as the whole element can be obtained. Note that the word "complementary" means color relationship in which an achromatic color is obtained when colors are mixed. That is, white light emission can be obtained by mixture of light from substances whose emission colors are complementary colors. Similarly in a light-emitting element having three light-emitting units, for example, white light can be obtained as the whole light-emitting element when emission colors of the first, second, and third light-emitting units are red, green, and blue, respectively.

Note that this embodiment can be combined with any of the other embodiments as appropriate.

Embodiment 4

Figure 4A:
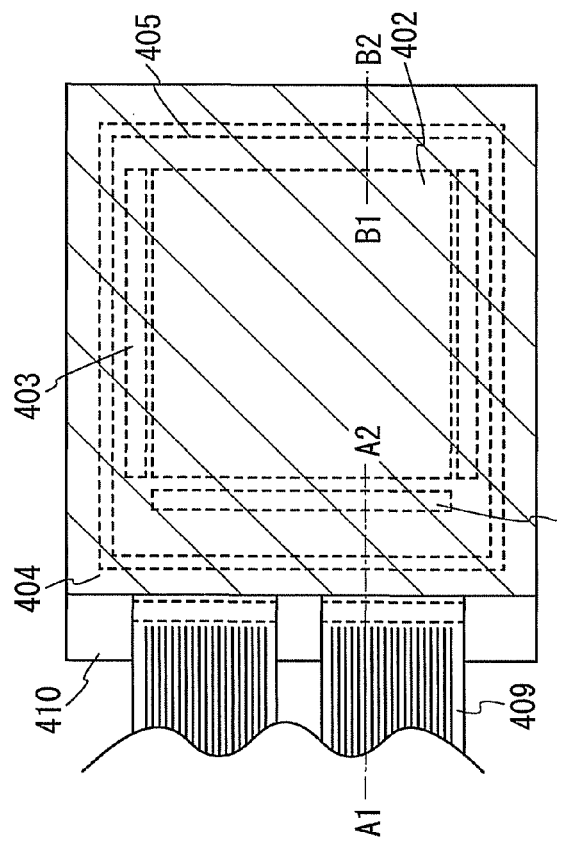
FIGS. 4A and 4B illustrate a light-emitting device according to one embodiment of the present invention.
Figure 4B:
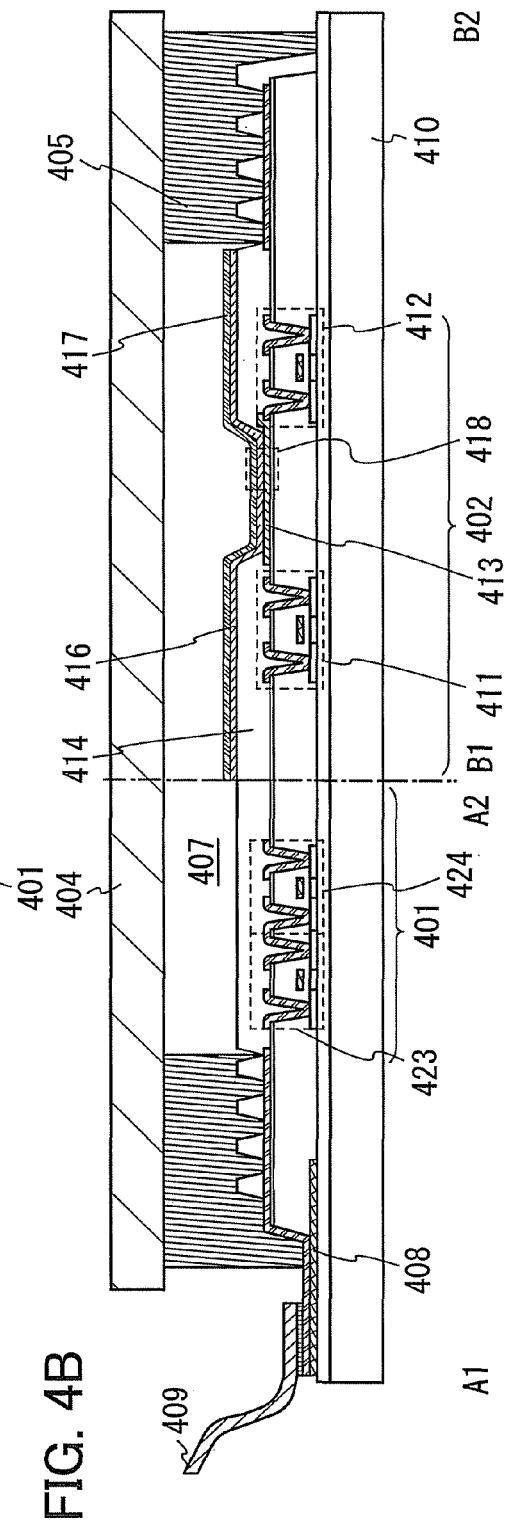

This embodiment shows a light-emitting device having a light-emitting element of Embodiment 2 or Embodiment 3 in a pixel portion with reference to FIGS. 4A and 4B. FIG. 4A is a top view illustrating a light-emitting device while FIG. 4B is a cross-sectional view along lines A1-A2 and B1-B2 of FIG. 4A.

The light-emitting device illustrated in FIG. 4A includes a driver circuit portion (a source side driver circuit 401), a pixel portion 402, a driver circuit portion (a gate side driver circuit 403), a sealing substrate 404, and a sealant 405; and a portion surrounded by the sealant 405 is a space 407.

A lead wiring 408 is a wiring to transmit a signal that is to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure is described with reference to FIG. 4B. The driver circuit portion and the pixel portion are formed over an element substrate 410. In this case, one pixel in the pixel portion 402 and the source side driver circuit 401 which is the driver circuit portion are illustrated. Note that as the source side driver circuit 401, a CMOS circuit which is obtained by combining an n-channel TFT 423 and a p-channel TFT 424 is formed. Such a driver circuit may be formed by using various circuits such as a CMOS circuit, a PMOS circuit, or an NMOS circuit. Although a driver-integrated type in which a driver circuit is formed over the substrate is described in Embodiment 4, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413.

In order to improve the coverage, the insulator 414 is preferably provided such that either an upper end portion or a lower end portion of the insulator 414 has a curved surface with a curvature. For example, when positive photosensitive acrylic is used as a material for the insulator 414, only an upper end portion of the insulator 414 can have a curved surface with a radius of curvature (0.2 μm to 3 μm). Alternatively, the insulator 414 can be formed using either a negative type photosensitive material that becomes insoluble in an etchant by light irradiation or a positive type photosensitive material that becomes soluble in an etchant by light irradiation.

Over the first electrode 413, an EL layer 416 and a second electrode 417 are formed. In this case, the first electrode 413 can be formed using any of a variety of materials such as metals, alloys, and electrically conductive compounds or a mixture thereof. Note that as specific materials, it is possible to use the materials described in Embodiment 2 as a material that can be used for the first electrode.

The EL layer 416 is formed by any of a variety of methods such as an evaporation method using an evaporation mask, an inkjet method, and a spin coating method. The EL layer 416 has the structure described in Embodiment 2 or Embodiment 3. Further, as another material included in the EL layer 416, any of low molecular compounds and high molecular compounds (including oligomers and dendrimers) may be used. The material used for the EL layer may be an organic compound or an inorganic compound.

The second electrode 417 can be formed using any of a variety of metals, alloys, and electrically conductive compounds, or a mixture thereof. Among such materials, a metal, an alloy, an electrically conductive compound, a mixture thereof, or the like having a low work function (a work function of 3.8 eV or lower) is preferably used when the second electrode 417 is used as a cathode. Examples include elements belonging to Group 1 or Group 2 in the periodic table, i.e., alkali metals such as lithium (Li) and cesium (Cs), alkaline earth metals such as magnesium (Mg), calcium (Ca), and strontium (Sr), alloys thereof (e.g., MgAg and AlLi), and the like.

Note that in the case where light generated in the EL layer 416 is transmitted through the second electrode 417, the second electrode 417 can be formed using a stack of a metal thin film with a reduced thickness and a transparent electrically conductive film (indium oxide-tin oxide (ITO), indium oxide-tin oxide containing silicon or silicon oxide, indium oxide-zinc oxide, or indium oxide containing tungsten oxide and zinc oxide, graphene, or the like).

By joining the sealing substrate 404 and the element substrate 410 with the sealant 405, a structure is formed in which the light-emitting element 418 is provided in the space 407 surrounded by the element substrate 410, the sealing substrate 404, and the sealant 405. Note that the space 407 is filled with a filler such as an inert gas (e.g., nitrogen or argon) or the sealant 405.

Note that as the sealant 405, an epoxy-based resin is preferably used. A material thereof is desirably a material which does not transmit moisture or oxygen as much as possible. The sealing substrate 404 can be formed of a glass substrate; a quartz substrate; or a plastic substrate including fiberglass-reinforced plastics (FRP), polyvinyl fluoride (PVF), polyester, acrylic, or the like.

In the above manner, the active matrix light-emitting device having the light-emitting element described in Embodiment 2 or Embodiment 3 can be provided.

Figure 5A:
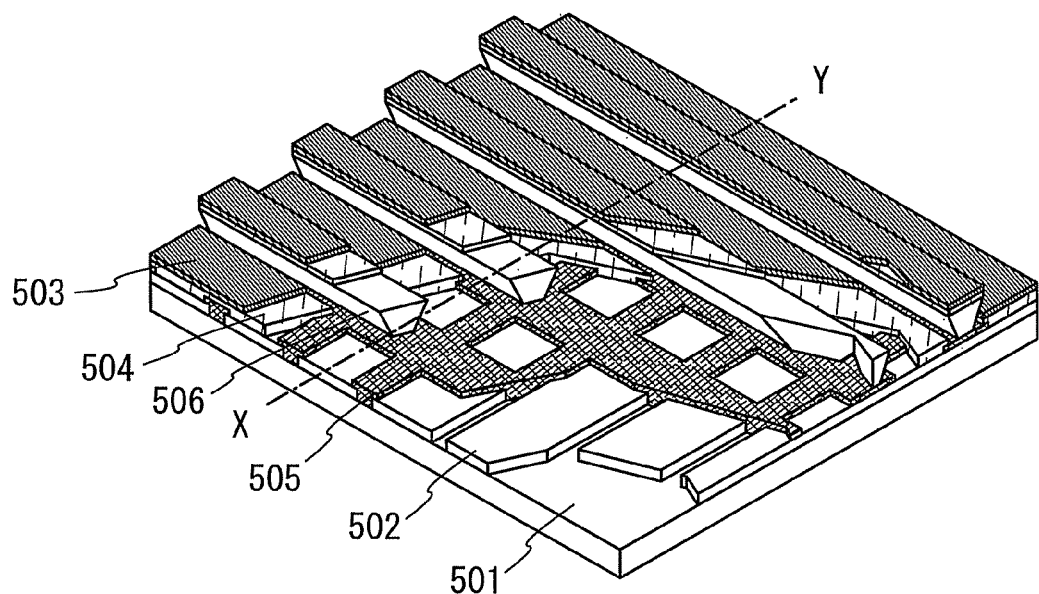
FIGS. 5A and 5B illustrate a light-emitting device according to one embodiment of the present invention.
Figure 5B:
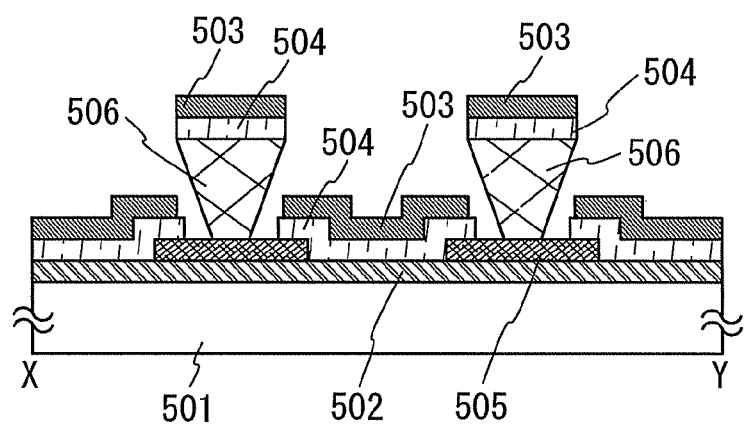

Further, the light-emitting element of Embodiment 2 or Embodiment 3 can be used for a passive matrix light-emitting device instead of the above active matrix light-emitting device. FIGS. 5A and 5B illustrate a perspective view and a cross-sectional view of a passive matrix light-emitting device using the light-emitting element described in the above embodiment. FIG. 5A is a perspective view of the light-emitting device, and FIG. 5B is a cross-sectional view taken along a line X-Y of FIG. 5A.

In FIGS. 5A and 5B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The side surfaces of the partition layer 506 slope so that the distance between one side surface and the other side surface gradually decreases toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). By providing the partition layer 506 in such a manner, a defect of the light-emitting element due to static electricity or the like can be prevented.

Accordingly, the passive matrix light-emitting device having the light-emitting element of Embodiment 2 or Embodiment 3 can be provided.

Note that any of the light-emitting devices described in this embodiment (the active matrix light-emitting device and the passive matrix light-emitting device) are fowled using the light-emitting element described in the above embodiment, which has high emission efficiency and a long lifetime, and accordingly a light-emitting device with low power consumption and high reliability can be provided.

Note that this embodiment can be implemented in appropriate combination with the structure described in any of the other embodiments.

Embodiment 5

Embodiment 5 shows electronic devices which include the light-emitting device described in Embodiment 4 as a part.

Since the light-emitting device described in Embodiment 4 includes the light-emitting element containing the anthracene compound described in Embodiment 1, the power consumption of the light-emitting device is reduced; as a result, electronic devices described in this embodiment can be electronic devices having a display portion with low power consumption. In addition, electronic devices driven with a low driving voltage can be provided. Further, electronic devices having high reliability can be provided.

Examples of the electronic devices to which the light-emitting device is applied include television sets (also referred to as televisions or television receivers), monitors of computers or the like, cameras such as digital cameras or digital video cameras, digital photo frames, cellular phones (also referred to as mobile phones or cellular phone sets), portable game consoles, portable information terminals, audio reproducing devices, large game machines such as pachinko machines, and the like. Specific examples of these electronic devices are described below.

Figure 6A:
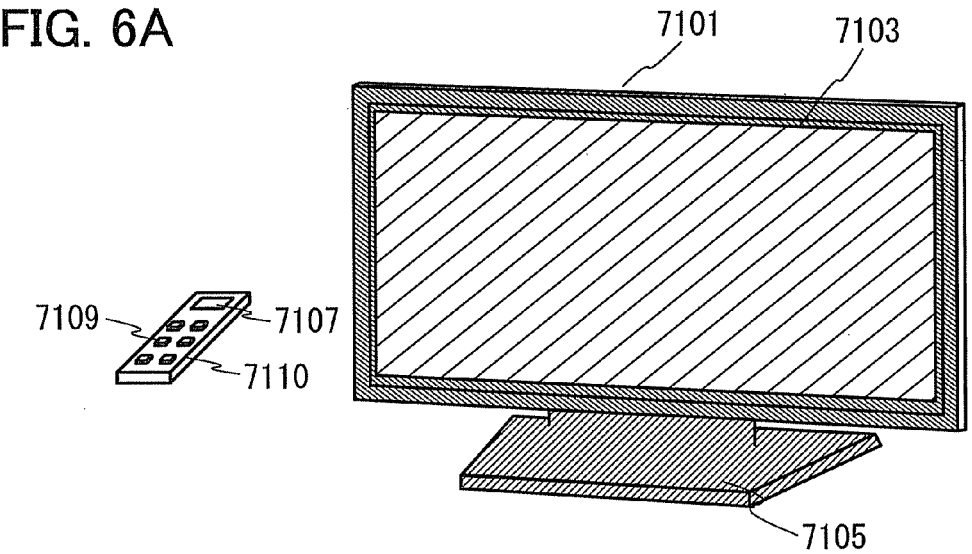
FIGS. 6A to 6D illustrate electronic devices according to embodiments of the present invention.

FIG. 6A illustrates an example of a television device. In the television device, a display portion 7103 is incorporated in a housing 7101. In addition, here, the housing 7101 is supported by a stand 7105. Images can be displayed on the display portion 7103, and the display portion 7103 is formed using light-emitting elements arranged in matrix, each of which is similar to that described in Embodiment 2 or 3. The light-emitting elements can have high emission efficiency because they contain the anthracene compound described in Embodiment 1. In addition, a light-emitting element driven with a low driving voltage can be provided. Further, a light-emitting element having high reliability can be provided. Therefore, this television device having the display portion 7103 which is formed using the light-emitting elements consumes less power. In addition, a television device driven with a low driving voltage can be provided. Further, a television device having high reliability can be provided.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the display device is connected to a communication network with or without wires via the modem, one-way (from a sender to a receiver) or two-way (between a sender and a receiver or between receivers) information communication can be performed.

Figure 6B:
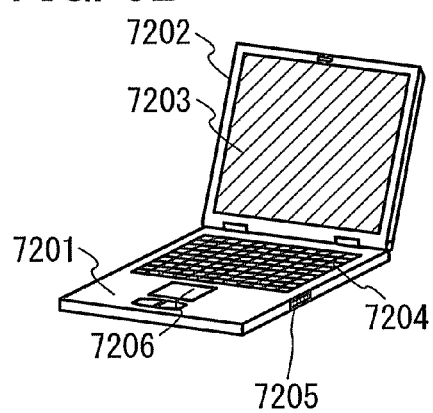

FIG. 6B illustrates a computer, which includes a main body 7201, a housing 7202, a display portion 7203, a keyboard 7204, an external connection port 7205, a pointing device 7206, and the like. Note that this computer is formed using light-emitting elements arranged in Matrix, each of which is similar to that described in Embodiment 2 or 3, for the display portion 7203. The light-emitting elements can have high emission efficiency because they contain the anthracene compound described in Embodiment 1. In addition, a light-emitting element driven with a low driving voltage can be provided. Further, a light-emitting element having high reliability can be provided. Therefore, this computer having the display portion 7203 which is formed using the light-emitting elements consumes less power. In addition, a computer driven with a low driving voltage can be provided. Further, a computer having high reliability can be provided.

Figure 6C:
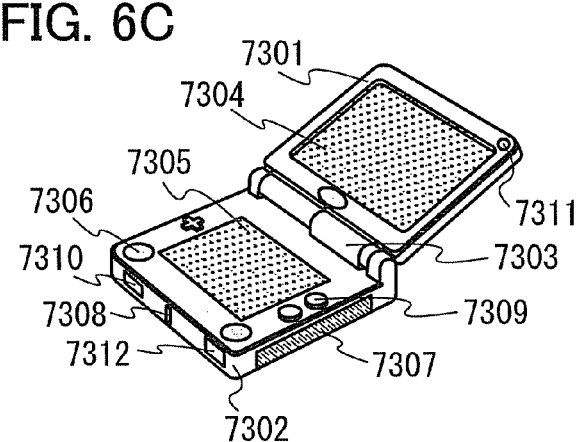

FIG. 6C illustrates a portable game machine having two housings, a housing 7301 and a housing 7302, which are connected with a joint portion 7303 so that the portable game machine can be opened or folded. A display portion 7304 formed using light-emitting elements arranged in matrix, each of which is similar to that described in Embodiment 2 or 3 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, tilt angle, vibration, smell, or infrared rays), or a microphone 7312), and the like. Needless to say, the structure of the portable game machine is not limited thereto, and at least one or both of the display portions 7304 and 7305 is/are formed using the light-emitting elements arranged in matrix, each of which is similar to that described in Embodiment 2 or 3, and another accessory may be provided as appropriate. The portable game machine illustrated in FIG. 6C has a function of reading a program or data stored in a recording medium to display it on the display portion, and a function of sharing information with another portable game machine by wireless communication. Note that the functions of the portable game machine illustrated in FIG. 6C are not limited to these functions, and the portable game machine can have various functions. The portable game machine including the above-described display portion 7304 can be a portable game machine with reduced power consumption because the light-emitting elements used in the display portion 7304 have high emission efficiency by containing the anthracene compound described in Embodiment 1. In addition, a portable game machine driven with a low driving voltage can be provided because the light-emitting elements used in the display portion 7304 can be driven with a low driving voltage by containing the anthracene compound described in Embodiment 1. Further, a portable game machine having high reliability can be provided because the light-emitting elements used in the display portion 7304 have high reliability by containing the anthracene compound described in Embodiment 1.

Figure 6D:
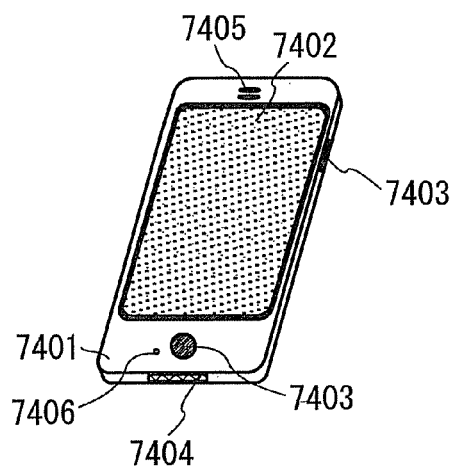

FIG. 6D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone includes the display portion 7402 formed using light-emitting elements arranged in matrix, each of which is similar to that described in Embodiment 2 or 3. The light-emitting elements can have high emission efficiency because they contain the anthracene compound described in Embodiment 1. In addition, a light-emitting element driven with a low driving voltage can be provided. Further, a light-emitting element having high reliability can be provided. Therefore, this mobile phone having the display portion 7402 which is formed using the light-emitting elements consumes less power. In addition, a mobile phone driven with a low driving voltage can be provided. Further, a mobile phone having high reliability can be provided.

When the display portion 7402 of the mobile phone illustrated in FIG. 6D is touched with a finger or the like, data can be input into the mobile phone. In this case, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating an e-mail, a text input mode mainly for inputting text is selected for the display portion 7402 so that text displayed on a screen can be inputted. In that case, it is preferable to display a keyboard or number buttons on almost all the area of the screen of the display portion 7402.

When a detection device which includes a sensor for detecting inclination, such as a gyroscope or an acceleration sensor, is provided inside the mobile phone, the direction of the mobile phone (whether the mobile phone is placed horizontally or vertically for a landscape mode or a portrait mode) is determined so that display on the screen of the display portion 7402 can be automatically switched.

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may also function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

As described above, there is an extremely wide application range of the light-emitting device, such as the light-emitting device described in Embodiment 4, including the light-emitting elements containing the anthracene compound described in Embodiment 1; therefore, the light-emitting device can be applied to electronic devices of a variety of fields. By using the anthracene compound described in Embodiment 1, an electronic device with reduced power consumption can be provided. In addition, an electronic device driven with a low driving voltage can be provided. Further, an electronic device having high reliability can be provided.

The light-emitting device described in Embodiment 4 can also be used as a lighting device. One embodiment in which the light-emitting device described in Embodiment 4 is used as a lighting device is described with reference to FIG. 7.

Figure 7:
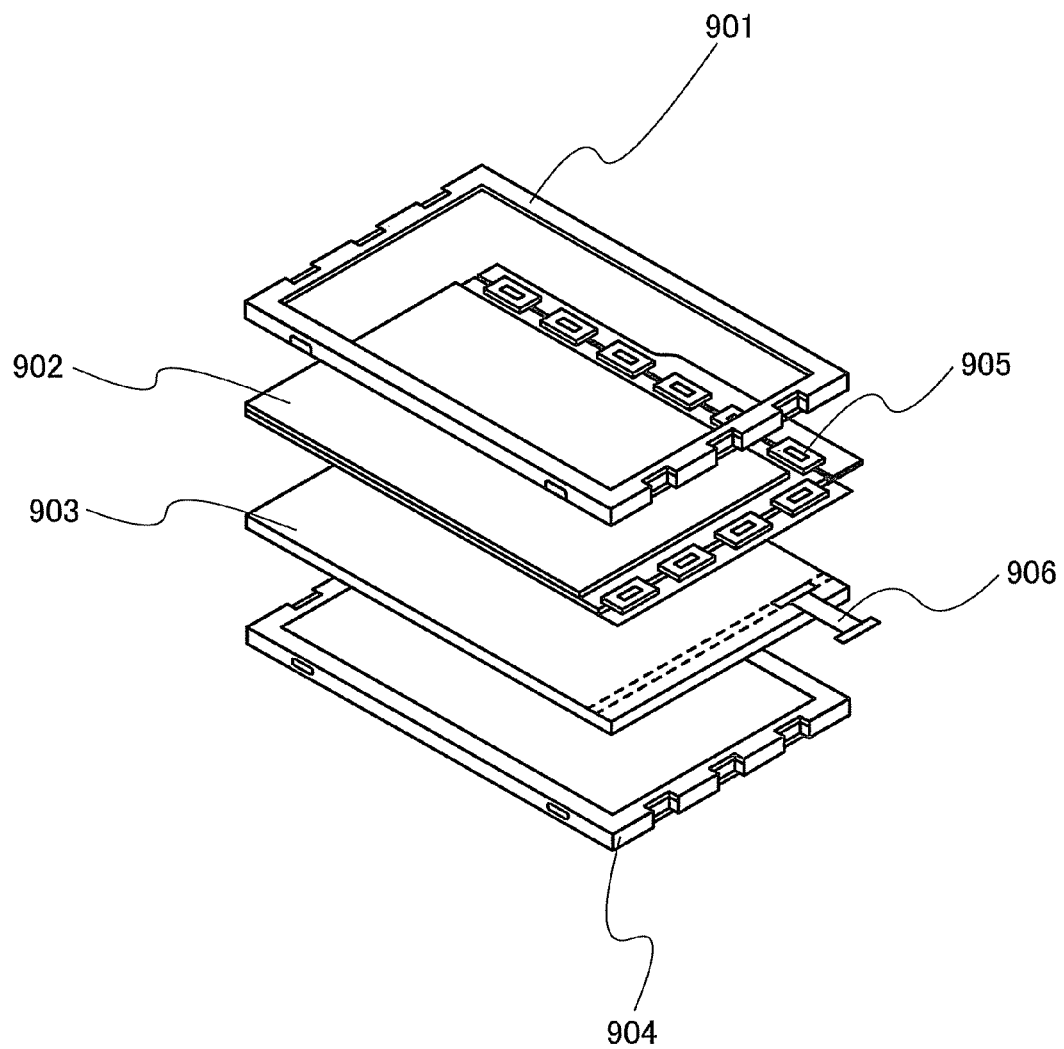
FIG. 7 illustrates an electronic device according to one embodiment of the present invention.

FIG. 7 illustrates an example of a liquid crystal display device using the light-emitting device described in Embodiment 4 as a backlight. The liquid crystal display device illustrated in FIG. 7 includes a housing 901, a liquid crystal layer 902, a backlight 903, and a housing 904, in which the liquid crystal layer 902 is connected to a driver IC 905. The light-emitting device described in Embodiment 4 is used as the backlight 903, to which current is supplied through a terminal 906.

With the use of the light-emitting device described in Embodiment 4 as the backlight of the liquid crystal display device, the backlight consumes less power. Further, the light-emitting device described in Embodiment 4 is a lighting device with plane light emission and can have a large area. Therefore, the backlight can have a large area, and a liquid crystal display device having a large area can be obtained. Furthermore, since the light-emitting device described in Embodiment 4 is thin, it becomes possible to reduce the thickness of a display device.

Figure 8:
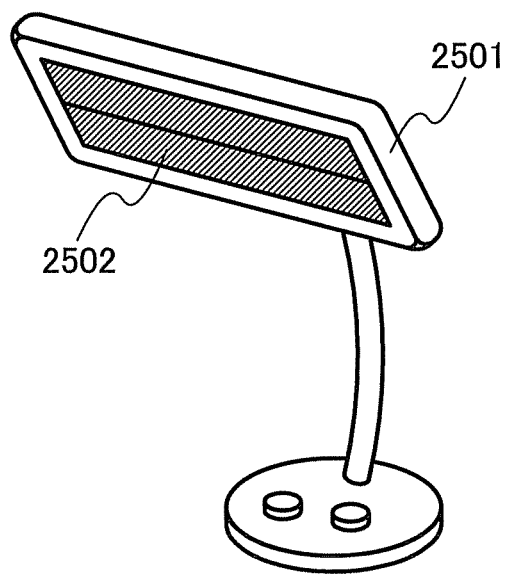
FIG. 8 illustrates a lighting device according to one embodiment of the present invention.

FIG. 8 illustrates an example in which the light-emitting device described in Embodiment 4 is used as a table lamp, which is a kind of lighting device. The table lamp illustrated in FIG. 8 includes a housing 2501 and a light source 2502, and the light-emitting device described in Embodiment 4 is used as the light source 2502.

Figure 9:
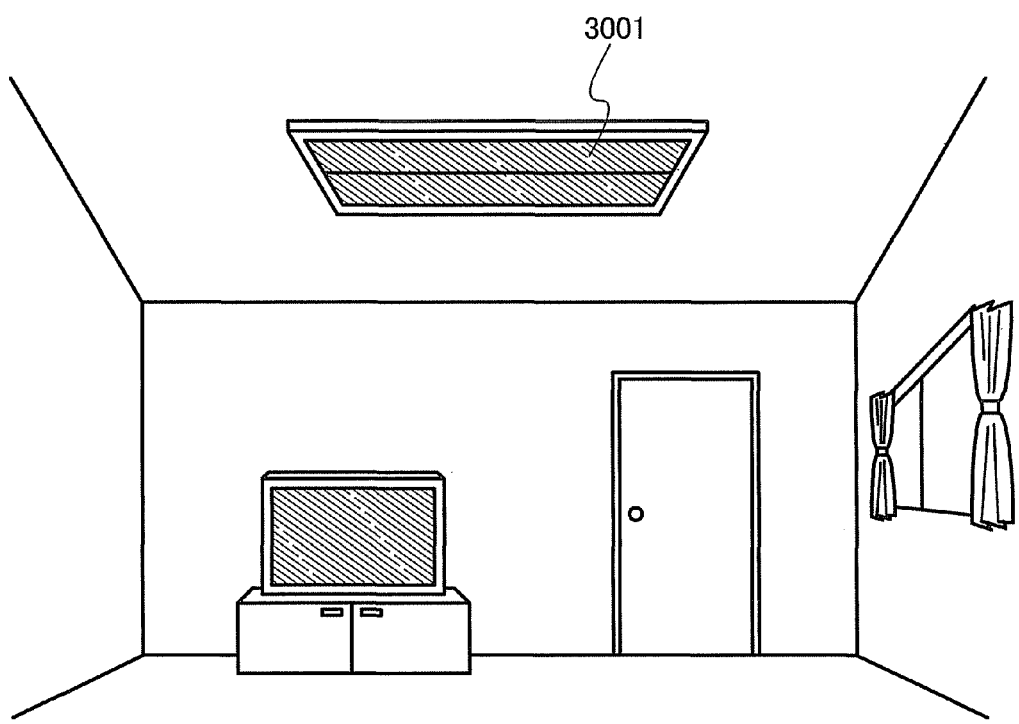
FIG. 9 illustrates a lighting device according to one embodiment of the present invention.

FIG. 9 illustrates an example in which the light-emitting device described in Embodiment 4 is used as an indoor lighting device 3001. Since the light-emitting device described in Embodiment 4 consumes less power, a lighting device that consumes less power can be obtained. Further, since the light-emitting device described in Embodiment 4 can have a large area, the light-emitting device can be used as a large-area lighting device. Furthermore, since the light-emitting device described in Embodiment 4 is thin, the light-emitting device described in Embodiment 4 can be used as a lighting device having a reduced thickness.

Figure 10:
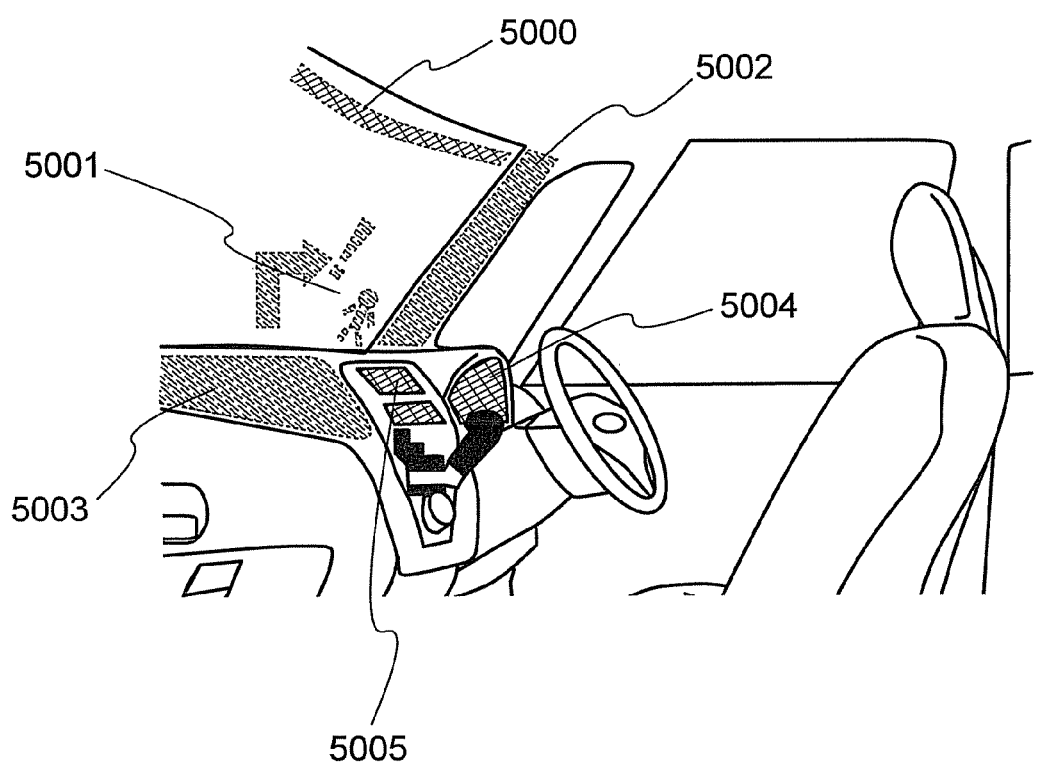
FIG. 10 illustrates in-vehicle display devices and lighting devices.

The light-emitting element described in Embodiment 4 can be used for a windshield or a dashboard on a car. FIG. 10 illustrates one embodiment in which the light-emitting device described in Embodiment 4 is used for a windshield or a dashboard on a car. Displays 5000 to 5005 each include the light-emitting device described in Embodiment 4.

The display 5000 and the display 5001 are light-emitting devices provided in the windshield on the car, which are described in Embodiment 4. The light-emitting devices described in Embodiment 4 can be so-called see-through display devices, through which the opposite side can be seen, because a first electrode and a second electrode are formed using light-transmitting materials. Such see-through display devices can be provided even in the windshield on the car, without hindering the vision. In addition, for example, when a transistor for driving the light-emitting element is provided, a transistor having a light-transmitting property, such as an organic transistor using an organic semiconductor material or a transistor using an oxide semiconductor, is preferably used.

The display 5002 is a display device provided in a pillar portion. The display 5002 can compensate for the view hindered by the pillar portion by showing an image taken by an imaging unit provided in the car body. Similarly, the display 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage, fuel meter, gearshift indicator, and air condition. The content or layout of the display can be changed freely by a user as appropriate. Further, such information can also be shown in the displays 5000 to 5003.

Note that the displays 5000 to 5005 can be used as lighting devices by light emission on the entire areas of the displays 5000 to 5005.

Since the light-emitting device described in Embodiment 4 includes the anthracene compound described in Embodiment 1, it can be driven with a low driving voltage or reduce power consumption. When a number of large screens are provided, load to a battery can be reduced, which provides comfortable driving.

Example 1

In this example is shown a synthetic example of N-(dibenzofuran-2-yl)-4-(10-phenylanthracen-9-yl)diphenylamine (abbreviation: FrAPA) represented by the structural formula (100) in Embodiment 1.

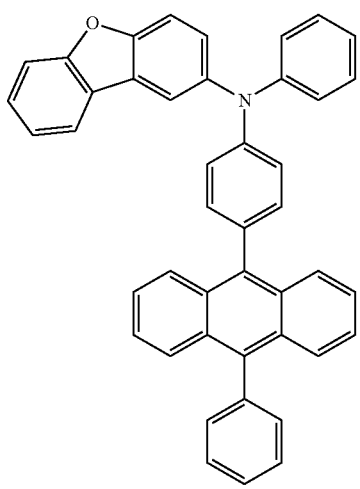

(100)

[Step 1: Method of Synthesizing 2-Iododibenzofuran]

In a 500-mL three-neck flask was put a suspension of 8.4 g (50 mmol) of dibenzofuran, 6.2 g (25 mmol) of iodine, 5.7 g (25 mmol) of orthoperiodic acid, 150 mL of glacial acetic acid, 30 mL of water, and 500 μL of sulfuric acid, and the suspension was heated and stirred at 60° C. for 4.5 hours to cause a reaction.

After the reaction, the reaction mixture was further stirred at room temperature for 16 hours. The generated precipitate was collected by filtration, and the resulting matter was dissolved in 150 mL of toluene. Then, the solution was washed with water three times. Magnesium sulfate was added to the toluene solution to adsorb moisture.

This solution was filtered, and the resulting filtrate was concentrated. Then, hexane was added thereto, followed by irradiation with ultrasonic waves. The generated solid was collected by filtration and dried, so that the objective substance was obtained as 11.3 g of white powder in 77% yield. A reaction scheme of this synthesis method is shown in (B-1) below.

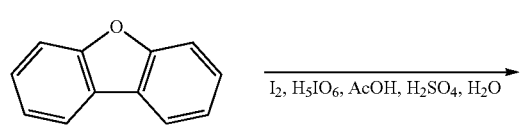

(B-1)

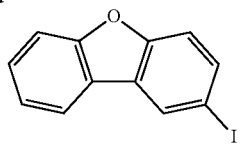

The compound obtained in Step 1 was subjected to a nuclear magnetic resonance (NMR) measurement. The measurement data are shown below.

$^1$H NMR (CDCl$_3$, 300 MHz): δ (ppm)=7.33-7.38 (m, 2H), 7.48 (dt, J=1.5 Hz, 8.4 Hz, 1H), 7.56 (d, J=8.1 Hz, 1H), 7.72 (dd, J=2.1 Hz, 8.4 Hz, 1H), 7.95 (d, J=7.8 Hz, 1H), 8.27 (d, J=1.5 Hz, 1H).

The measurement results confirmed that the objective substance, 2-iododibenzofuran, was obtained.

[Step 2: Method of Synthesizing N-(Dibenzofuran-2-yl)-phenylamine (Abbreviation: FrA)]

In a 100-mL three-neck flask were put 4.5 g (15 mmol) of 2-iododibenzofuran, 2.0 g (20 mmol) of aniline, 45 mg (0.1 mmol) of bis(dibenzylideneacetone)palladium(0), and 3.0 g (30 mmol) of sodium-tert-butoxide (abbreviation: tert-BuONa), and 30 mL of dehydrated xylene was added. Then, deaeration was performed for 3 minutes until no bubbles came out. To this suspension, 0.5 mL (0.3 mmol) of tri-tert-butylphosphine (10 wt % hexane solution) was added, and then the mixture was heated and stirred at 120° C. for 5 hours in a nitrogen atmosphere to cause a reaction.

About 200 mL of toluene was added to this reaction suspension, and the mixture was filtered through Florisil (produced by Wako Pure Chemical Industries, Ltd., Catalog No. 540-00135), alumina, and Celite (produced by Wako Pure Chemical Industries, Ltd., Catalog No. 531-16855). The resulting filtrate was washed with water, and magnesium sulfate was added thereto to adsorb moisture.

This suspension was further filtered through Florisil, alumina, and Celite, and the resulting filtrate was concentrated. Then, methanol was added thereto, followed by irradiation with ultrasonic waves. The generated solid was collected by filtration and dried, so that the objective substance was obtained as 1.6 g of white powder in 39% yield. A reaction scheme of this synthesis method is shown in (B-2) below.

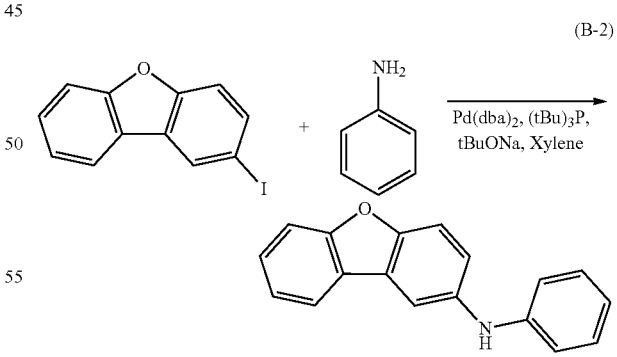

(B-2)

The Rf values of the objective substance, 2-iododibenzofuran, and aniline were respectively 0.28, 0.59, and 0.07, which were found by silica gel thin layer chromatography (TLC) (with a developing solvent of ethyl acetate and hexane in a ratio of 1:10).

The compound obtained in Step 2 was subjected to a nuclear magnetic resonance (NMR) measurement. The measurement data are shown below.

$^1$NMR (CDCl$_3$, 300 MHz): δ (ppm)=5.80 (s, 1H), 6.94-7.68 (m, 10H), 8.99 (d, J=7.8 Hz, 1H), 8.11 (s, 1H).

The measurement results confirmed that the objective substance, N-(dibenzofuran-2-yl)-phenylamine (abbreviation: FrA), was obtained.

[Step 3: Method of Synthesizing N-(dibenzofuran-2-yl)-4-(10-phenylanthracen-9-yl)diphenylamine (Abbreviation: FrAPA)]

In a 100-mL three-neck flask were put 1.1 g (4.3 mmol) of N-(dibenzofuran-2-yl)-phenylamine, 1.6 g (4.2 mmol) of 9-(4-bromophenyl)-10-phenylanthracene, 10 mg (20 μmol) of bis(dibenzylideneacetone)palladium(0), and 1.0 g (10 mmol) of sodium-tert-butoxide (abbreviation: tert-BuONa), and 20 mL of dehydrated xylene was added. Then, deaeration was performed for 3 minutes until no bubbles came out. To this suspension, 100 μL (50 μmol) of tri-tert-butylphosphine (10 wt % hexane solution) was added, and the mixture was heated and stirred at 110° C. for 4 hours in a nitrogen atmosphere to cause a reaction.

About 150 mL of toluene was added to this reaction suspension, and the mixture was filtered through Florisil, alumina, and Celite. The resulting filtrate was washed with water, and magnesium sulfate was added thereto to adsorb moisture.

This suspension was further filtered through Florisil, alumina, and Celite, and the resulting filtrate was concentrated. Then, acetone and methanol were added thereto, followed by irradiation with ultrasonic waves. The generated solid was collected by filtration and dried, so that the objective substance was obtained as 2.2 g of pale yellow powder in 90% yield. A reaction scheme of this synthesis method is shown in (B-3) below.

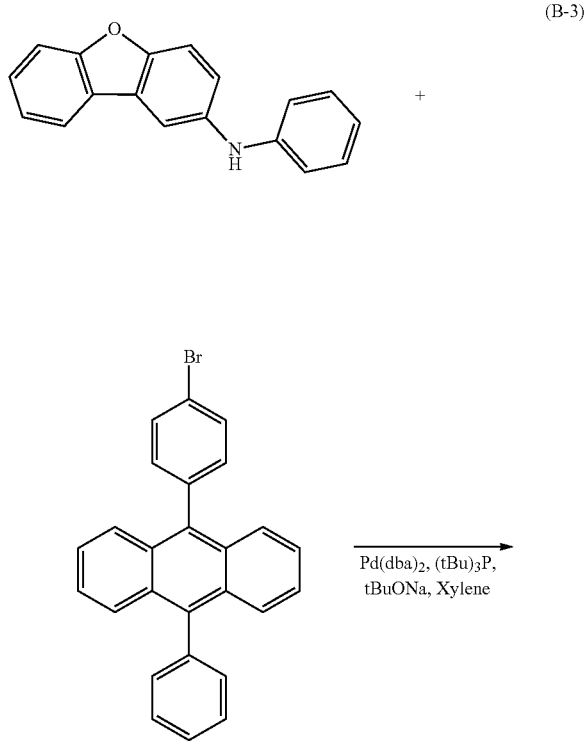

(B-3)

The Rf values of the objective substance, 9-(4-bromophenyl)-10-phenylanthracene, and N-(dibenzofuran-2-yl)-phenylamine were respectively 0.58, 0.72, and 0.37, which were found by silica gel thin layer chromatography (TLC) (with a developing solvent of ethyl acetate and hexane in a ratio of 1:10).

The compound obtained in Step 3 was subjected to a nuclear magnetic resonance (NMR) measurement. The measurement data are shown below.

$^1$H NMR (CDCl$_3$, 300 MHz): δ (ppm)=7.07 (t, J=7.2 Hz, 1H), 7.28-7.49 (m, 17H), 7.54-7.63 (m, 5H), 7.69 (d, J=8.1 Hz, 2H), 7.87-7.93 (m, 4H).

The measurement results confirmed that the objective substance, N-(dibenzofuran-2-yl)-4-(10-phenylanthracen-9-yl)diphenylamine (abbreviation: FrAPA), was obtained.

The molecular weight of the above compound was measured by a GC-MS detector (ITQ1100 ion trap GC-MS system, manufactured by Thermo Fisher Scientific K.K.). With this, a main peak at a molecular weight of 587.3 (the mode was EI+) was detected, and thus it is confirmed that the objective substance, N-(dibenzofuran-2-yl)-4-(10-phenylanthracen-9-yl)diphenylamine (abbreviation: FrAPA), was obtained.

Figure 11A:
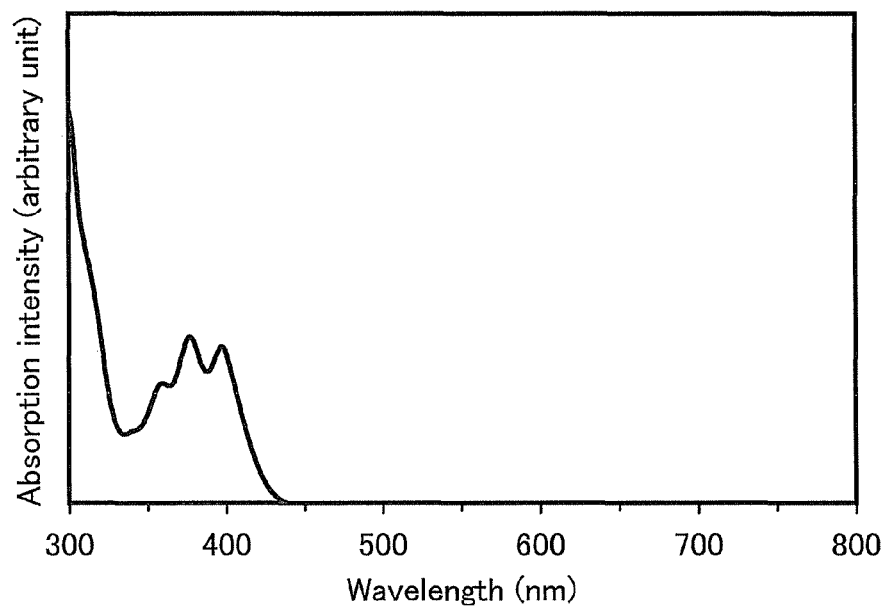
FIG. 11A shows an absorption spectrum of FrAPA in a toluene solution.
Figure 11B:
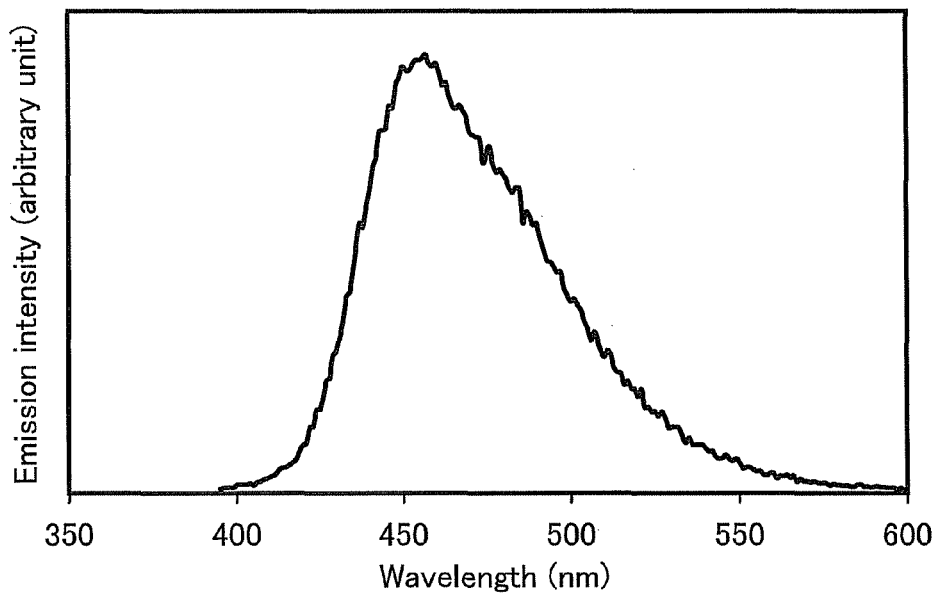
FIG. 11B shows an emission spectrum thereof.
Figure 12A:
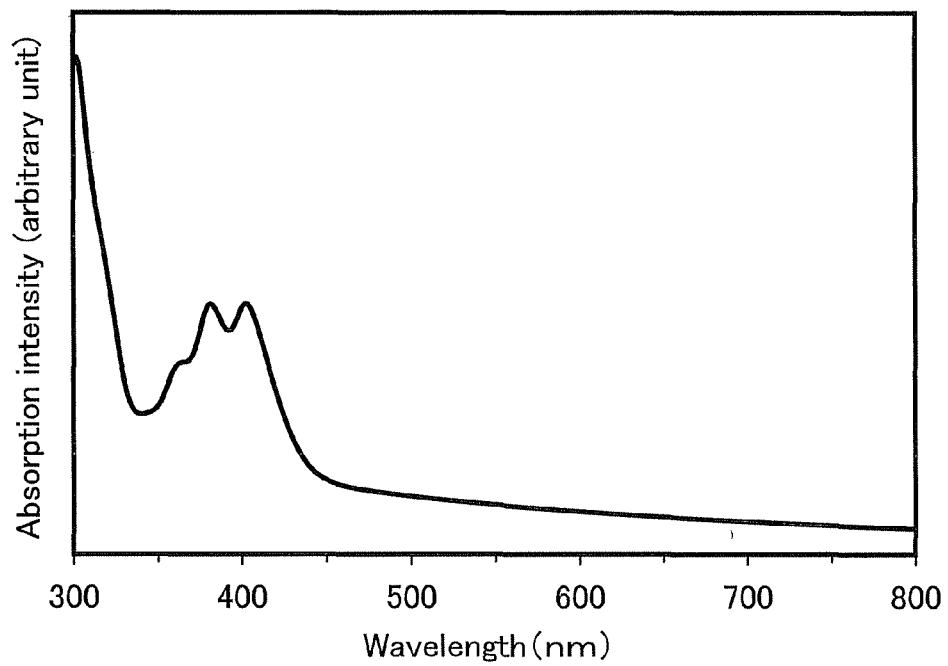
FIG. 12A shows an absorption spectrum of a thin film of FrAPA.
Figure 12B:
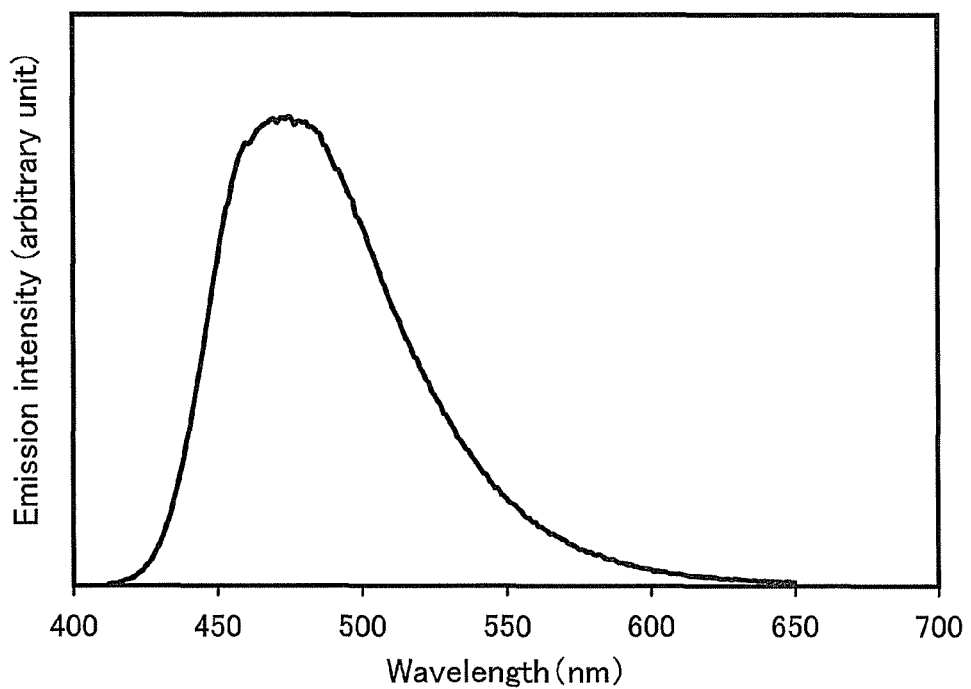
FIG. 12B shows an emission spectrum thereof.

FIG. 11A shows an absorption spectrum of FrAPA in a toluene solution, and FIG. 11B shows an emission spectrum thereof. In addition, FIG. 12A shows an absorption spectrum of a thin film of FrAPA, and FIG. 12B shows an emission spectrum thereof. The absorption spectra were measured by using a UV-visible spectrophotometer (V-550, produced by JASCO Corporation). The emission spectra were measured by using a fluorescence spectrophotometer (FS920, produced by Hamamatsu Photonics Corporation). For the measurements, samples of the toluene solution were prepared by being put in a quartz cell and samples of the thin film were prepared by being evaporated onto a quartz substrate. The absorption spectrum of FrAPA in a toluene solution was obtained by subtracting absorption spectra of the quartz cell and toluene, and the absorption spectrum of the thin film of FrAPA was obtained by subtracting an absorption spectrum of a quartz substrate. In FIGS. 11A and 11B and FIGS. 12A and 12B, the vertical axes represent absorption intensity (arbitrary unit) or emission intensity (arbitrary unit), and the horizontal axes represent wavelength (nm). In the case of the toluene solution, the absorption peaks were observed at around 374 nm and 395 nm, and the maximum emission wavelength was 457 nm (excitation wavelength: 375 nm). In the case of the thin film, the absorption peaks were observed at around 375 nm and 402 nm, and the maximum emission wavelength was 475 nm (excitation wavelength: 402 nm).

The absorption spectra show that FrAPA described in this example is a material having weak absorption of light in the visible region. In addition, the emission spectra show that FrAPA emits blue light.

Oxidation-reduction characteristics were explored by cyclic voltammetry (CV) measurement. Note that an electrochemical analyzer (ALS model 600A or 600C, produced by BAS Inc.) was used for the measurement.

The oxidation characteristics were measured in the following manner: the potential of a working electrode with respect to a reference electrode was scanned from −0.13 V to 0.80 V, and then from 0.80 V to −0.13 V. Even after the 100 cycles of this scanning, the oxidation peak took a similar value. This indicates that the compound of this example has characteristics effective against repetitive redox reactions between an oxidation state and a neutral state.

The reduction characteristics were measured in the following manner: the potential of the working electrode with respect to the reference electrode was scanned from −0.25 V to −2.50 V, and then from −2.50 V to −0.25 V. Even after the 100 cycles of this scanning, the reduction peak took a similar value. This indicates that the compound of this example has characteristics effective against repetitive redox reactions between a reduction state and a neutral state.

Example 2

In this example is shown a synthetic example of 4-(dibenzofuran-2-yl)-4'-(10-phenylanthracen-9-yl)triphenylamine (abbreviation: FrBAPA) represented by the structural formula (101) in Embodiment 1.

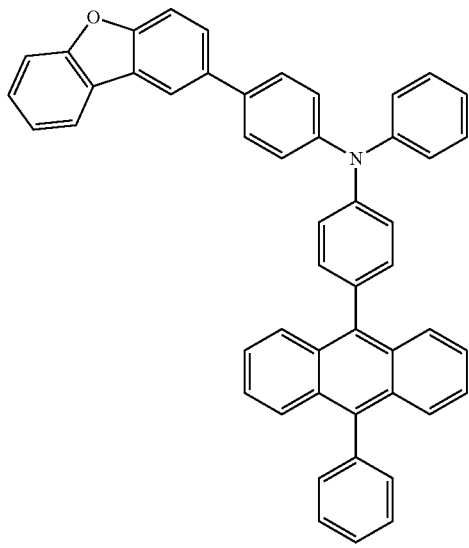

(101)

[Step 1: Method of Synthesizing Dibenzofuran-2-boronic Acid]

In a 500-mL three-neck flask was put 8.8 g (30 mmol) of 2-iododibenzofuran, and the atmosphere in the flask was replaced by nitrogen. Then, 200 mL of dehydrated tetrahydrofuran (abbreviation: THF) was added thereto and the mixture was cooled to −78° C. To this mixture was dripped 22 mL (36 mmol) of an n-butyllithium hexane solution (1.63 mol/L), and the mixture was stirred for 4 hours to cause a reaction.

To this reaction mixture was added 4.6 mL (45 mmol) of trimethyl borate, and the mixture was stirred at −78° C. for 2 hours and at room temperature for 20 hours. After the reaction, diluted hydrochloric acid was added to this reaction solution until the mixture was made acid, and then the mixture was stirred for 2 hours.

The stirred solution was subjected to extraction with ethyl acetate, and the obtained organic layer was washed with a saturated aqueous solution of sodium chloride. After the washing, magnesium sulfate was added to the organic layer to adsorb moisture. This suspension was filtered, and the resulting filtrate was concentrated to give an objective substance. A reaction scheme of this synthesis method is shown in (C-1) below.

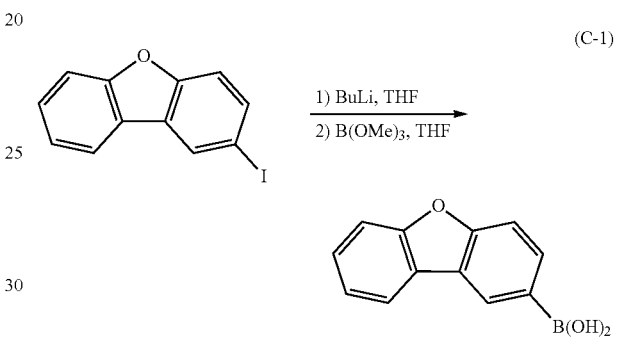

(C-1)

[Step 2: Method of Synthesizing 4-(Dibenzofuran-2-yl) diphenylamine (abbreviation: FrBA)]

In a 500-mL three-neck flask was deaerated a mixture of 7.3 g (30 mmol) of 4-bromodiphenylamine, 6.3 g (30 mmol) of dibenzofuran-2-boronic acid, 67 mg (0.3 mmol) of palladium(II) acetate, 180 mg (0.6 mmol) of tri(o-tolyl)phosphine, 40 mL of toluene, 20 mL of ethanol, and 20 mL of an aqueous solution of potassium carbonate (2 mol/L) while being stirred under reduced pressure, and then the mixture was heated and stirred in a nitrogen atmosphere at 80° C. for 20 hours to cause a reaction.

To this reaction suspension was added ethyl acetate, and the suspension was washed with water. Then, magnesium sulfate was added to the obtained organic layer to adsorb moisture. This suspension was filtered through Florisil, alumina, silica gel, and Celite. The resulting filtrate was concentrated, followed by purification by silica gel column chromatography (with a developing solvent of ethyl acetate and hexane in a ratio of 1:10). Recrystallization was performed on the obtained solution, so that the objective substance was obtained as 1.8 g of pale yellow powder in 18% yield. A reaction scheme of this synthesis is shown in (C-2) below.

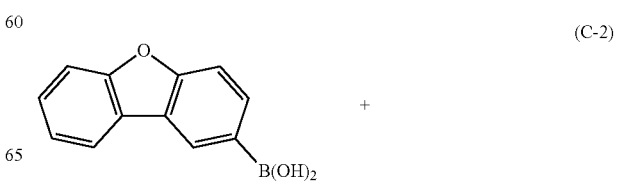

(C-2)

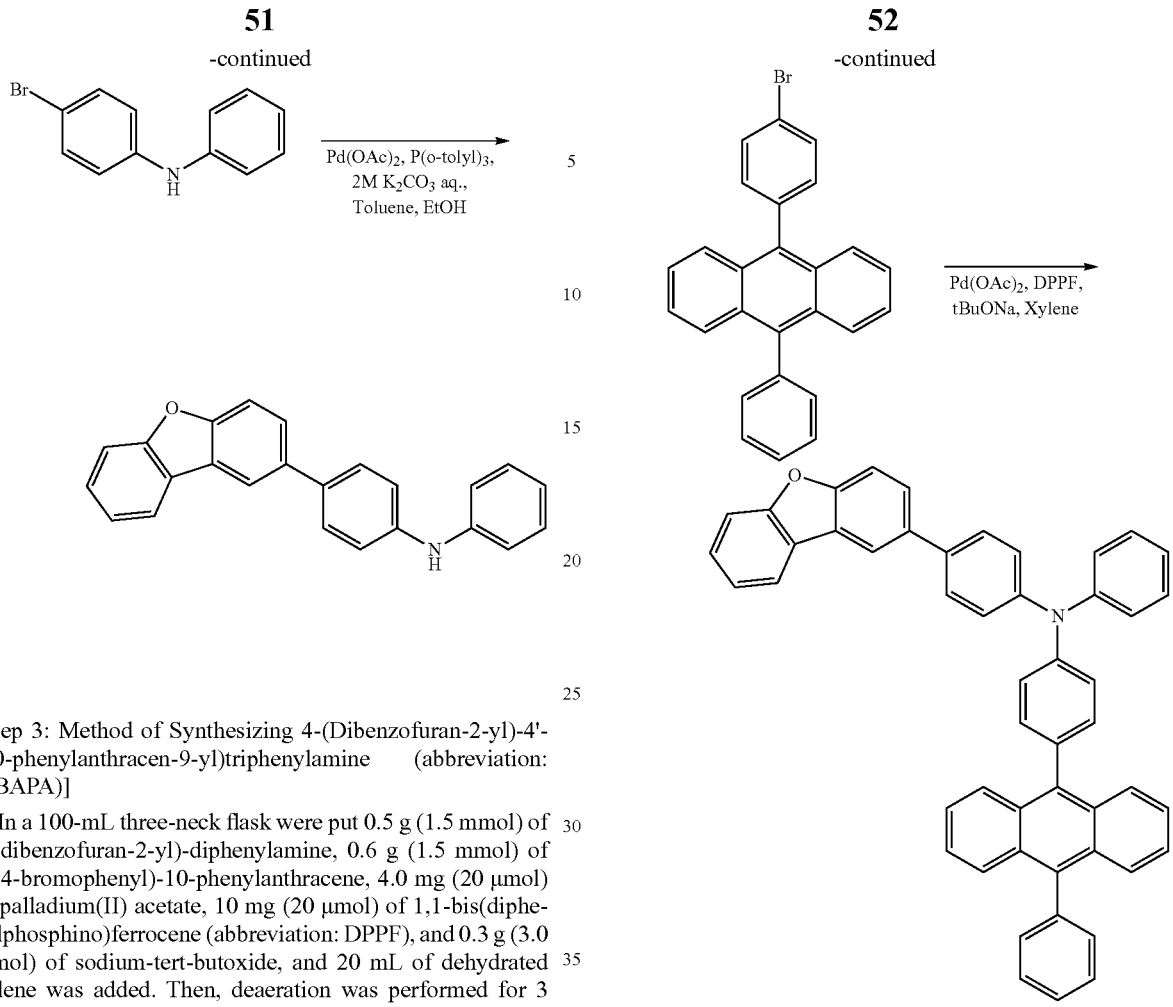

[Step 3: Method of Synthesizing 4-(Dibenzofuran-2-yl)-4'-(10-phenylanthracen-9-yl)triphenylamine (abbreviation: FrBAPA)]

In a 100-mL three-neck flask were put 0.5 g (1.5 mmol) of 4-(dibenzofuran-2-yl)-diphenylamine, 0.6 g (1.5 mmol) of 9-(4-bromophenyl)-10-phenylanthracene, 4.0 mg (20 μmol) of palladium(II) acetate, 10 mg (20 μmol) of 1,1-bis(diphenylphosphino)ferrocene (abbreviation: DPPF), and 0.3 g (3.0 mmol) of sodium-tert-butoxide, and 20 mL of dehydrated xylene was added. Then, deaeration was performed for 3 minutes until no bubbles came out. To this suspension, 100 μL (50 μmol) of tri-tert-butylphosphine (10 wt % hexane solution) was added, and then the mixture was heated and stirred at 110° C. for 4 hours in a nitrogen atmosphere to cause a reaction.

About 150 mL of toluene was added to this reaction suspension, and the mixture was filtered through Florisil, alumina, and Celite. The resulting filtrate was washed with water, and magnesium sulfate was added thereto to adsorb moisture. The resulting filtrate was concentrated, followed by purification by silica gel column chromatography (with a developing solvent of ethyl acetate and hexane in a ratio of 1:10). Then, hexane was added to the obtained solution, followed by irradiation with ultrasonic waves. The generated solid was collected by filtration and dried, so that the objective substance was obtained as 340 mg of pale yellow powder in 34% yield. A reaction scheme of this synthesis method is shown in (C-3) below.

(C-3)

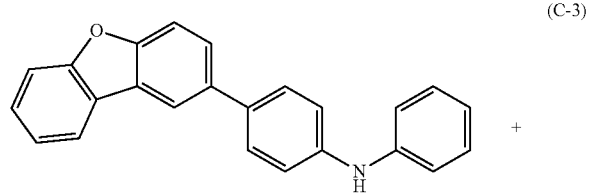
+

The Rf values of the objective substance, 9-(4-bromophenyl)-10-phenylanthracene, and 4-(dibenzofuran-2-yl)-diphenylamine were respectively 0.48, 0.67, and 0.30, which were found by silica gel thin layer chromatography (TLC) (with a developing solvent of ethyl acetate and hexane in a ratio of 1:10).

The compound obtained in Step 3 was subjected to a nuclear magnetic resonance (NMR) measurement. The measurement data are shown below.

$^1$H NMR (CDCl$_3$, 300 MHz): δ (ppm)=7.12 (t, J=6.6 Hz, 1H), 7.23-7.73 (m, 28H), 7.87 (d, J=7.87 Hz, 2H), 8.00 (d, J=6.9 Hz, 1H), 8.17 (d, J=1.5 Hz, 1H).

The molecular weight of the above compound was measured by a GC-MS detector (ITQ1100 ion trap GC-MS system, manufactured by Thermo Fisher Scientific K.K.). With this, a main peak at a molecular weight of 662.5 (the mode was EI+) was detected, and thus it is confirmed that the objective substance, 4-(dibenzofuran-2-yl)-4'-(10-phenylanthracen-9-yl)triphenylamine (abbreviation: FrBAPA), was obtained.

Figure 13A:
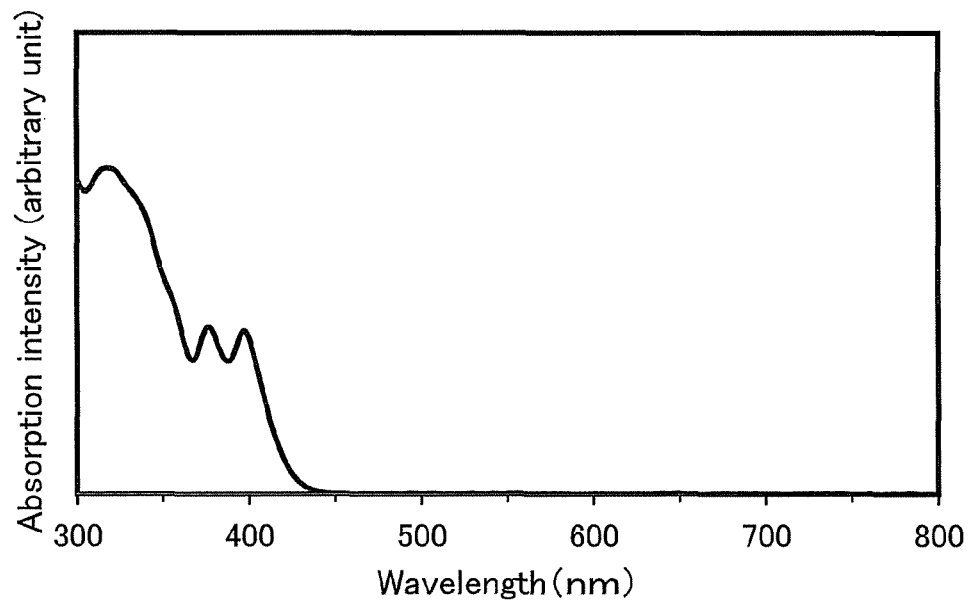
FIG. 13A shows an absorption spectrum of FrBAPA in a toluene solution.
Figure 13B:
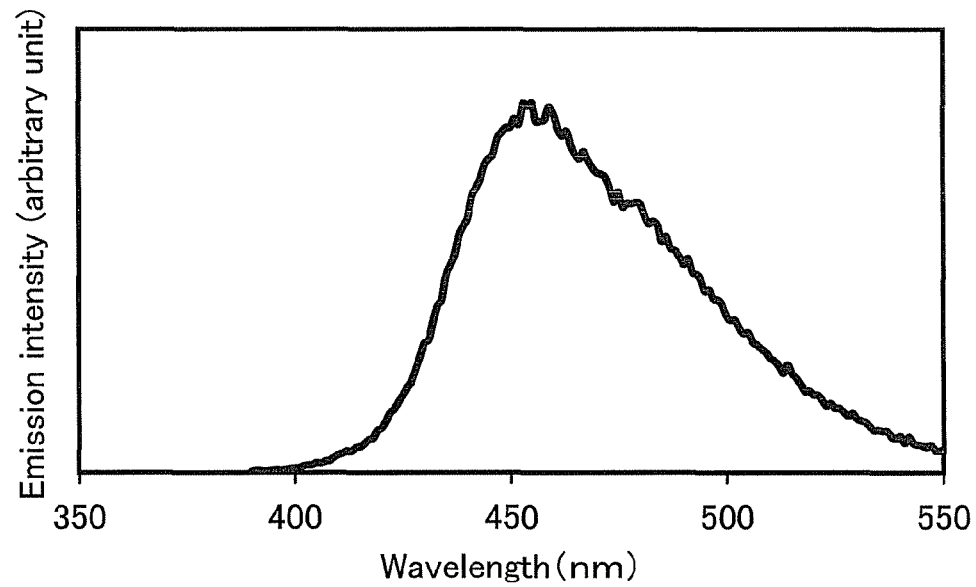
FIG. 13B shows an emission spectrum thereof.
Figure 14A:
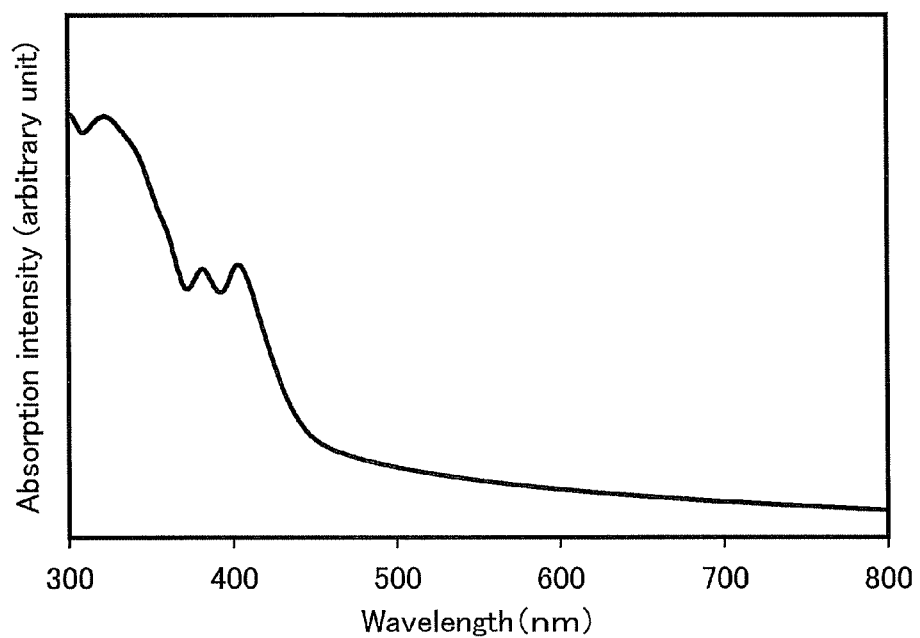
FIG. 14A shows an absorption spectrum of a thin film of FrBAPA.
Figure 14B:
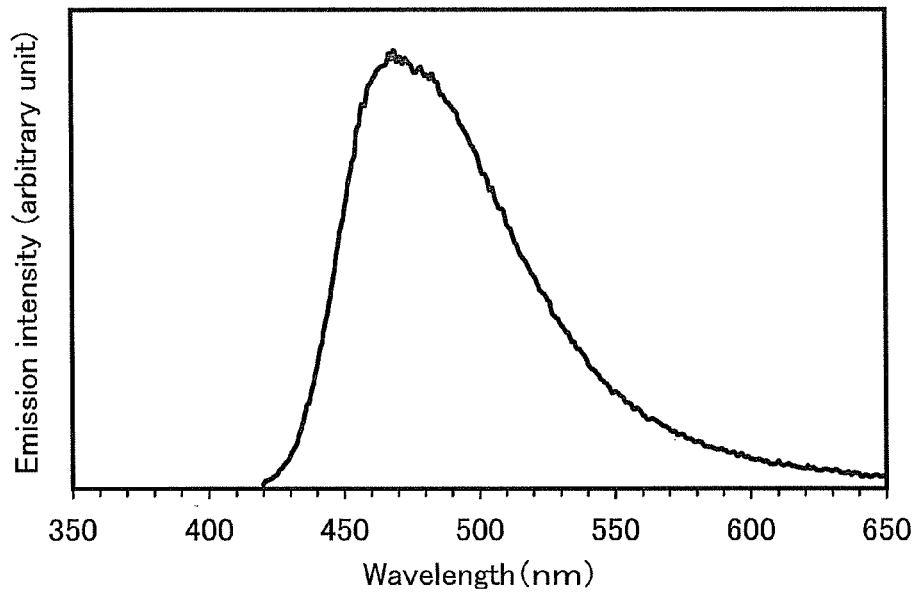
FIG. 14B shows an emission spectrum thereof.

FIG. 13A shows an absorption spectrum of FrBAPA in a toluene solution, and FIG. 13B shows an emission spectrum thereof. In addition, FIG. 14A shows an absorption spectrum of a thin film of FrBAPA, and FIG. 14B shows an emission spectrum thereof. The absorption spectra were measured by using a UV-visible spectrophotometer (V-550, produced by JASCO Corporation). The emission spectra were measured by using a fluorescence spectrophotometer (FS920, produced by Hamamatsu Photonics Corporation). For the measurements, samples of the toluene solution were prepared by being put in a quartz cell and samples of the thin film were prepared by being evaporated onto a quartz substrate. The absorption spectrum of FrBAPA in a toluene solution was obtained by subtracting absorption spectra of the quartz cell and toluene, and the absorption spectrum of the thin film of FrBAPA was obtained by subtracting an absorption spectrum of a quartz substrate. In FIGS. 13A and 13B and FIGS. 14A and 14B, the vertical axes represent absorption intensity (arbitrary unit) or emission intensity (arbitrary unit), and the horizontal axes represent wavelength (nm). In the case of the toluene solution, the absorption peaks were observed at around 319 nm, 375 nm, and 398 nm, and the maximum emission wavelength was 455 nm (excitation wavelength: 375 nm). In the case of the thin film, the absorption peaks were observed at around 322 nm, 381 nm, and 403 nm, and the maximum emission wavelength was 478 nm (excitation wavelength: 404 nm).

The absorption spectra show that FrBAPA described in this example is a material having weak absorption of light in the visible region. In addition, the emission spectra show that FrBAPA emits blue light.

Oxidation-reduction characteristics were explored by cyclic voltammetry (CV) measurement. Note that an electrochemical analyzer (ALS model 600A or 600C, produced by BAS Inc.) was used for the measurement.

The oxidation characteristics were measured in the following manner: the potential of a working electrode with respect to a reference electrode was scanned from 0.32 V to 1.00 V, and then from 1.00 V to 0.32 V. Even after the 100 cycles of this scanning, the oxidation peak took a similar value. This indicates that the compound of this example has characteristics effective against repetitive redox reactions between an oxidation state and a neutral state.

The reduction characteristics were measured in the following manner: the potential of the working electrode with respect to the reference electrode was scanned from −1.30 V to −2.50 V, and then from −2.50 V to −1.30 V. Even after the 100 cycles of this scanning, the reduction peak took a similar value. This indicates that the compound of this example has characteristics effective against repetitive redox reactions between a reduction state and a neutral state.

Example 3

In this example is shown a synthetic example of N-(dibenzothiophen-2-yl)-4-(10-phenylanthracen-9-yl)diphenylamine (abbreviation: ThAPA) represented by the structural formula (112) in Embodiment 1.

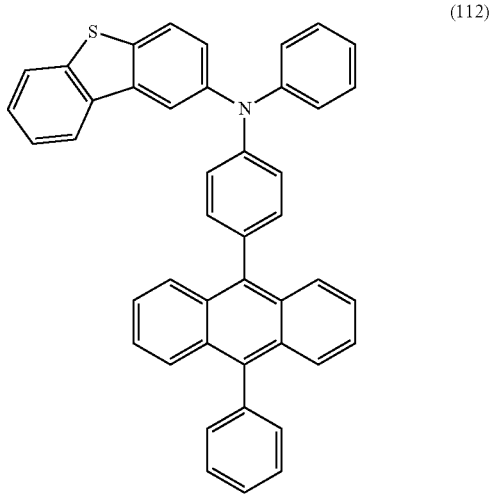 [SMILES: c1ccc(-c2c3ccccc3c(-c3ccc(N(c4ccccc4)c4ccc5sc6ccccc6c5c4)cc3)c3ccccc23)cc1]

(112)

[Step 1: Method of Synthesizing 2-Iododibenzothiophene]

In a 500-mL three-neck flask was put a suspension of 9.2 g (50 mmol) of dibenzothiophene, 6.2 g (25 mmol) of iodine, 5.7 g (25 mmol) of orthoperiodic acid, 150 mL of glacial acetic acid, 30 mL of water, and 500 μL of sulfuric acid, and the suspension was heated and stirred at 60° C. for 4.5 hours to cause a reaction.

After the reaction, the reaction mixture was further stirred at room temperature for 16 hours. The generated precipitate was collected by filtration, and the resulting matter was dissolved in 150 mL of toluene. Then, the solution was washed with water three times. Magnesium sulfate was added to the toluene solution to adsorb moisture.

This solution was filtered, and the resulting filtrate was concentrated. Then, hexane was added thereto, followed by irradiation with ultrasonic waves. The generated solid was collected by filtration and dried, so that the objective substance was obtained as 11.3 g of white powder in 77% yield. A reaction scheme of this synthesis method is shown in (D-1) below.

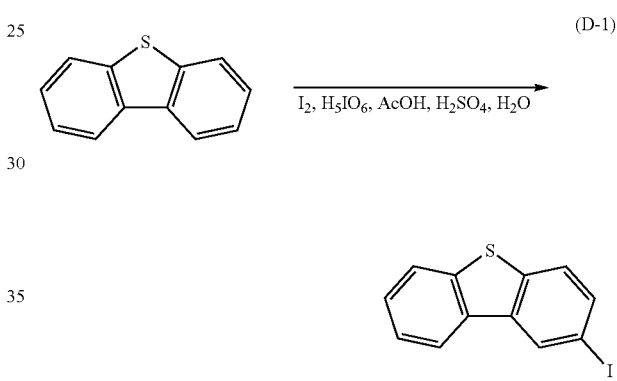

(D-1)

[Step 2: Method of Synthesizing N-(Dibenzothiophen-2-yl)-phenylamine]

In a 500-mL three-neck flask, 7.4 g (24 mmol) of 2-iododibenzothiophene, 25 g (25 mmol) of aniline, 280 mg (0.5 mmol) of bis(dibenzylideneacetone)palladium(0), and 8.0 g (80 mmol) of sodium-tert-butoxide (abbreviation: tert-BuONa) were put, and 30 mL of dehydrated xylene was added. Then, deaeration was performed for 3 minutes until no bubbles came out. To this suspension, 2.0 mL (1.0 mmol) of tri-tert-butylphosphine (10 wt % hexane solution) was added, and then the mixture was heated and stirred at 110° C. for 6.5 hours in a nitrogen atmosphere to cause a reaction.

About 200 mL of toluene was added to this reaction suspension, and the mixture was filtered through Florisil, alumina, and Celite. The resulting filtrate was washed with water, and magnesium sulfate was added thereto to adsorb moisture. This suspension was filtered and the resulting filtrate was concentrated, followed by purification by silica gel column chromatography (with a developing solvent of toluene and hexane in a ratio of 3:7). The obtained solution was concentrated, and then hexane was added thereto, followed by irradiation with ultrasonic waves. The generated solid was collected by filtration and dried, so that the objective substance was obtained as 2.9 g of pale yellow powder in 44% yield. A reaction scheme of this synthesis method is shown in (D-2) below.

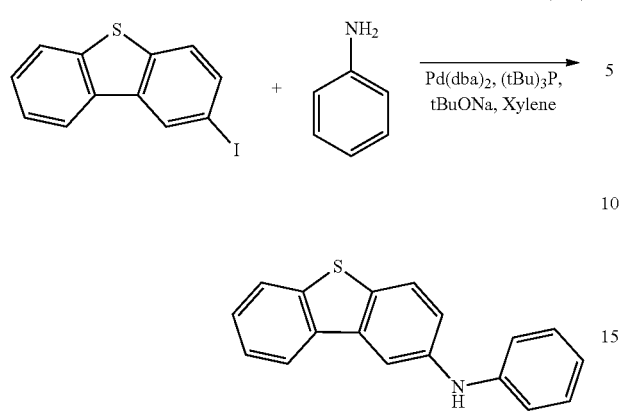

(D-2)

The Rf values of the objective substance and 2-iodobenzothiophene were respectively 0.26 and 0.61, which were found by silica gel thin layer chromatography (TLC) (with a developing solvent of ethyl acetate and hexane in a ratio of 1:10).

[Step 3: Method of Synthesizing N-(Dibenzothiophene-2-yl)-4-(10-phenylanthracen-9-yl)diphenylamine (abbreviation: ThAPA)]

In a 50-mL three-neck flask were put 0.8 g (3.0 mmol) of N-(dibenzothiophen-2-yl)-phenylamine, 1.2 g (3.0 mmol) of 9-(4-bromophenyl)-10-phenylanthracene, 5.0 mg (10 μmol) of bis(dibenzylideneacetone)palladium(0), and 0.8 g (8.0 mmol) of sodium-tert-butoxide (abbreviation: tert-BuONa), and 10 mL of dehydrated xylene was added. Then, deaeration was performed for 3 minutes until no bubbles came out. To this suspension, 100 μL (50 μmol) of tri-tert-butylphosphine (10 wt % hexane solution) was added, and the mixture was heated and stirred at 110° C. for 5 hours in a nitrogen atmosphere to cause a reaction.

About 300 mL of toluene was added to this reaction suspension, and the mixture was filtered through Florisil, alumina, and Celite. The resulting filtrate was washed with water, and magnesium sulfate was added thereto to adsorb moisture.

This suspension was further filtered through Florisil, alumina, and Celite. The resulting filtrate was concentrated, followed by purification by silica gel column chromatography (with a developing solvent of toluene and hexane in a ratio of 2:3). Then, the obtained solution was concentrated, and acetone and methanol were added thereto, followed by irradiation with ultrasonic waves. The generated solid was collected by filtration and dried, so that the objective substance was obtained as 1.0 g of pale yellow powder in 56% yield. A reaction scheme of this synthesis method is shown in (D-3) below.

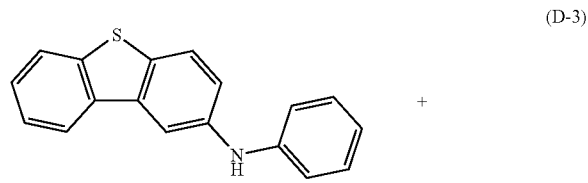

(D-3)

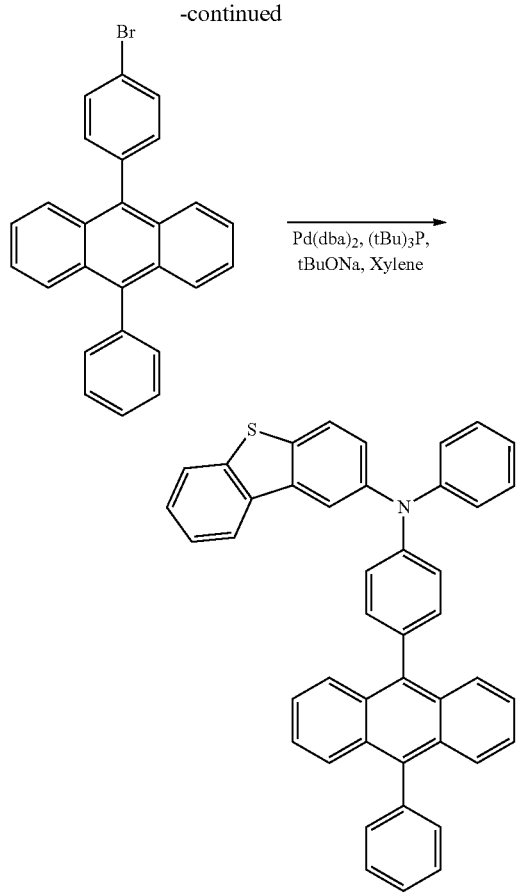

-continued

The Rf values of the objective substance, 9-(4-bromophenyl)-10-phenylanthracene, and N-(dibenzothiophen-2-yl)-phenylamine were respectively 0.41, 0.59, and 0.22, which were found by silica gel thin layer chromatography (TLC) (with a developing solvent of ethyl acetate and hexane in a ratio of 1:10).

The compound obtained in Step 3 was subjected to a nuclear magnetic resonance (NMR) measurement. The measurement data are shown below.

$^1$H NMR (CDCl$_3$, 300 MHz): δ (ppm)=7.09 (t, 1H), 7.32-7.60 (m, 21H), 7.70 (d, J=7.8 Hz, 2H), 7.82-7.89 (m, 4H), 8.07 (d, J=2.1 Hz, 1H).

The molecular weight of the above compound was measured by a GC-MS detector (ITQ1100 ion trap GC-MS system, manufactured by Thermo Fisher Scientific K.K.). With this, a main peak at a molecular weight of 603.3 (the mode was EI+) was detected, and thus it is confirmed that the objective substance, N-(dibenzothiophen-2-yl)-4-(10-phenylanthracen-9-yl)diphenylamine (abbreviation: ThAPA), was obtained.

Figure 15A:
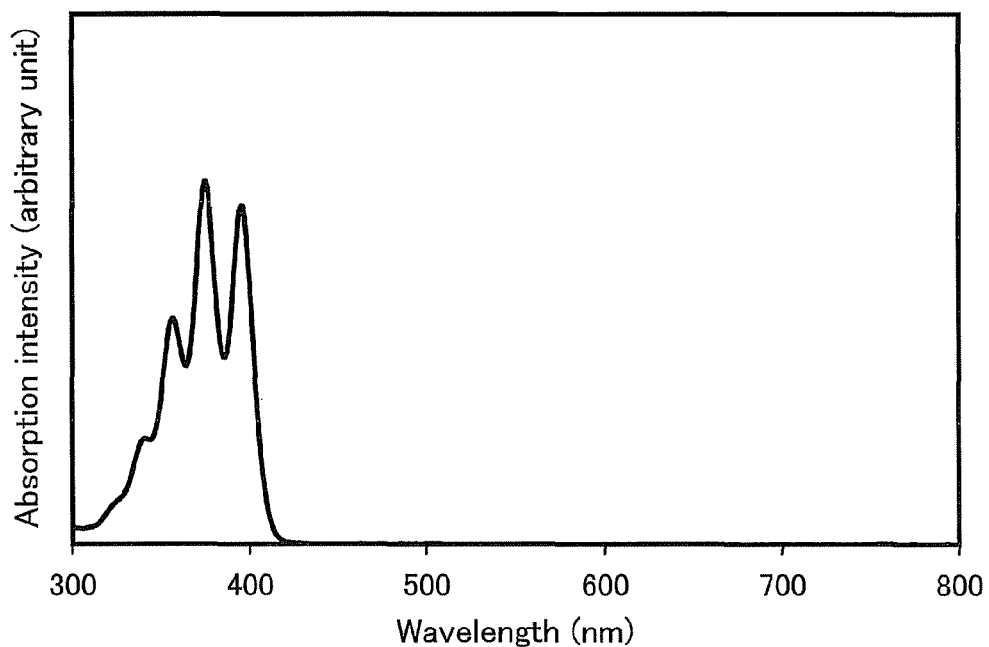
FIG. 15A shows an absorption spectrum of ThAPA in a toluene solution.
Figure 15B:
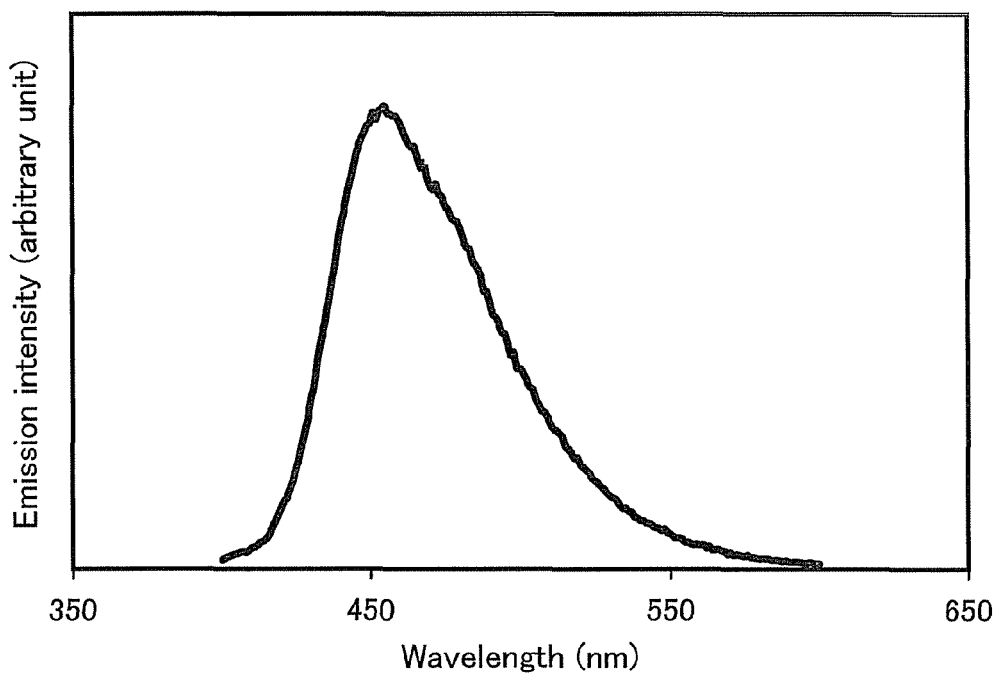
FIG. 15B shows an emission spectrum thereof.
Figure 16A:
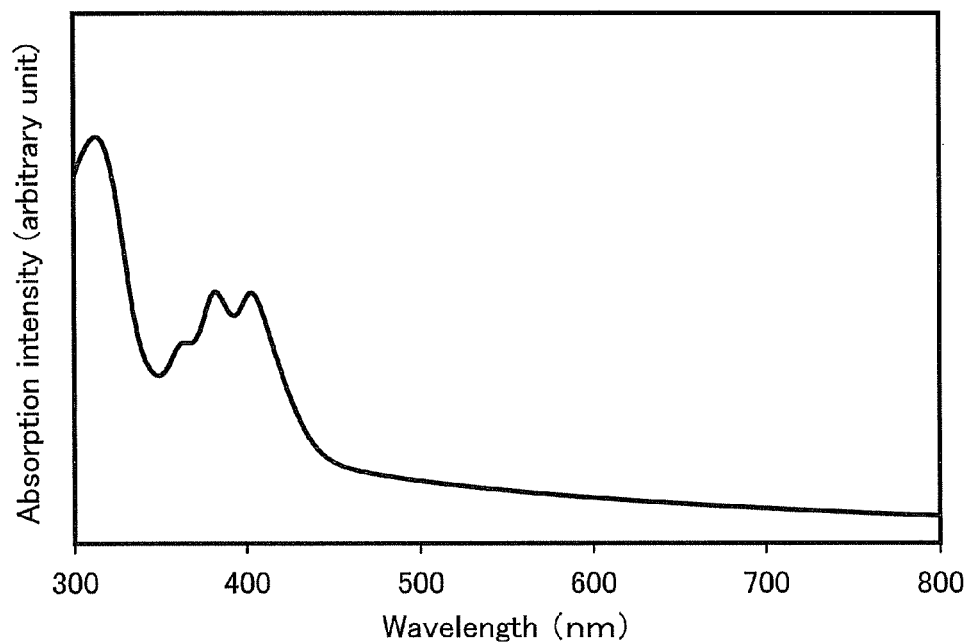
FIG. 16A shows an absorption spectrum of a thin film of ThAPA.
Figure 16B:
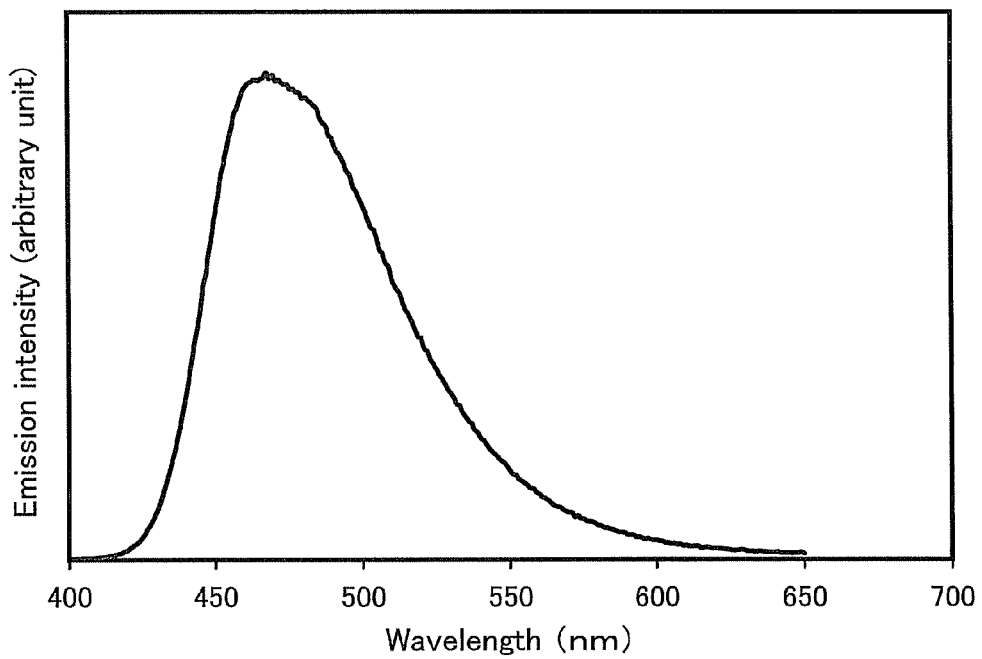
FIG. 16B shows an emission spectrum thereof.

FIG. 15A shows an absorption spectrum of ThAPA in a toluene solution, and FIG. 15B shows an emission spectrum thereof. In addition, FIG. 16A shows an absorption spectrum of a thin film of ThAPA, and FIG. 16B shows an emission spectrum thereof. The absorption spectra were measured by using a UV-visible spectrophotometer (V-550, produced by JASCO Corporation). The emission spectra were measured by using a fluorescence spectrophotometer (FS920, produced by Hamamatsu Photonics Corporation). For the measurements, samples of the toluene solution were prepared by being put in a quartz cell and samples of the thin film were prepared by being evaporated onto a quartz substrate. The absorption spectrum of ThAPA in a toluene solution was obtained by subtracting absorption spectra of the quartz cell and toluene, and the absorption spectrum of the thin film of ThAPA was obtained by subtracting an absorption spectrum of a quartz substrate. In FIGS. 15A and 15B and FIGS. 16A and 16B, the vertical axes represent absorption intensity (arbitrary unit) or emission intensity (arbitrary unit), and the horizontal axes represent wavelength (nm). In the case of the toluene solution, the absorption peak was observed at around 395 nm, and the maximum emission wavelength was 456 nm (excitation wavelength: 375 nm). In the case of the thin film, the absorption peaks were observed at around 313 nm, 382 nm, and 403 nm, and the maximum emission wavelength was 468 nm (excitation wavelength: 380 nm).

The absorption spectra show that ThAPA described in this example is a material having weak absorption of light in the visible region. In addition, the emission spectra show that ThAPA emits blue light.

Oxidation-reduction characteristics were explored by cyclic voltammetry (CV) measurement. Note that an electrochemical analyzer (ALS model 600A or 600C, produced by BAS Inc.) was used for the measurement.

The oxidation characteristics were measured in the following manner: the potential of a working electrode with respect to a reference electrode was scanned from −0.45 V to 0.70 V, and then from 0.70 V to −0.45 V. Even after the 100 cycles of this scanning, the oxidation peak took a similar value. This indicates that the compound of this example has characteristics effective against repetitive redox reactions between an oxidation state and a neutral state.

The reduction characteristics were measured in the following manner: the potential of the working electrode with respect to the reference electrode was scanned from −0.25 V to −2.50 V, and then from −2.50 V to −0.25 V. Even after the 100 cycles of this scanning, the reduction peak took a similar value. This indicates that the compound of this example has characteristics effective against repetitive redox reactions between a reduction state and a neutral state.

Example 4

In this example are shown results of measuring the highest occupied molecular orbital (HOMO) levels, the lowest unoccupied molecular orbital (LUMO) levels, and the band gaps of the anthracene compounds according to embodiments of the invention which were synthesized in Examples 1 to 3 in a thin film state.

Note that the measurement in this example was performed as described below. The value of the HOMO level was obtained by converting the value of the ionization potential obtained with a photoelectron spectrometer (AC-2, produced by Riken Keiki Co., Ltd.) into a negative value. The value of the LUMO level was obtained in such a manner that the absorption edge, which was obtained from Tauc plot with an assumption of direct transition, using data on the absorption spectrum of the thin film described in each Example, was regarded as an optical energy gap and was added to the value of the HOMO level.

Table 1 shows the HOMO levels, the LUMO levels, and the band gaps of FrAPA, FrBAPA, and ThAPA, which were obtained by the measurement.

TABLE 1

| Abbreviation | HOMO Level (eV) | LUMO Level (eV) | Band Gap (eV) |
|---|---|---|---|
| FrAPA | −5.58 | −2.71 | 2.87 |
| FrBAPA | −5.55 | −2.68 | 2.87 |
| ThAPA | −5.53 | −2.68 | 2.85 |

From Table 1, it is confirmed that FrAPA, FrBAPA, and ThAPA, which are the anthracene compounds according to embodiments of the present invention, have relatively deep HOMO levels, shallow LUMO levels, and wide band gaps.

Example 5

In this example are described a method of fabricating light-emitting elements in which the anthracene compounds according to embodiments of the present invention, which are synthesized in Examples 1 and 2, are used as light-emitting materials, and results of measuring the element characteristics.

A method of fabricating a light-emitting element 1 and a light-emitting element 2 is described below with reference to FIG. 17A. In addition, structural formulas of organic compounds used in this example are shown below.

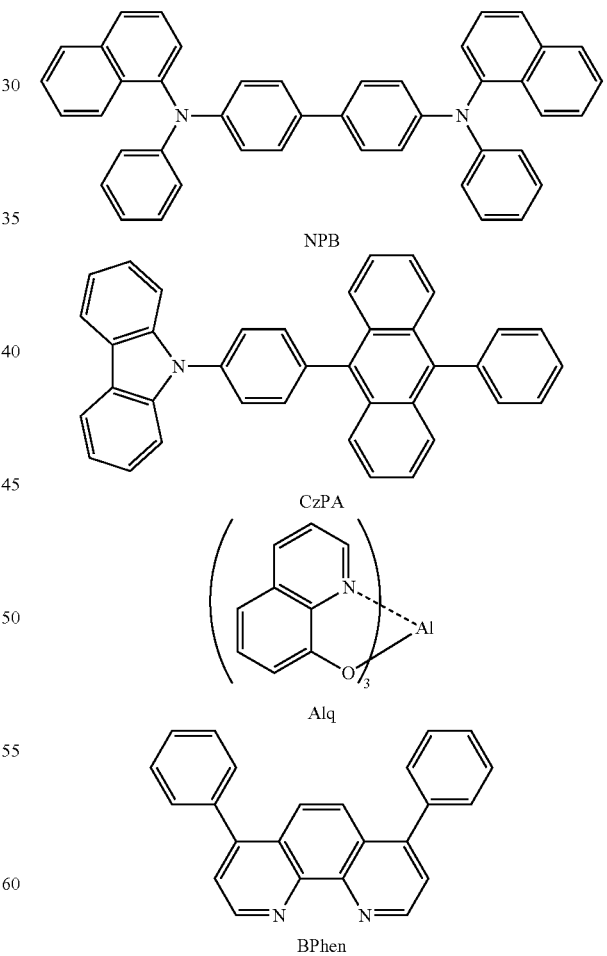

(Light-Emitting Element 1)

Figure 17A:
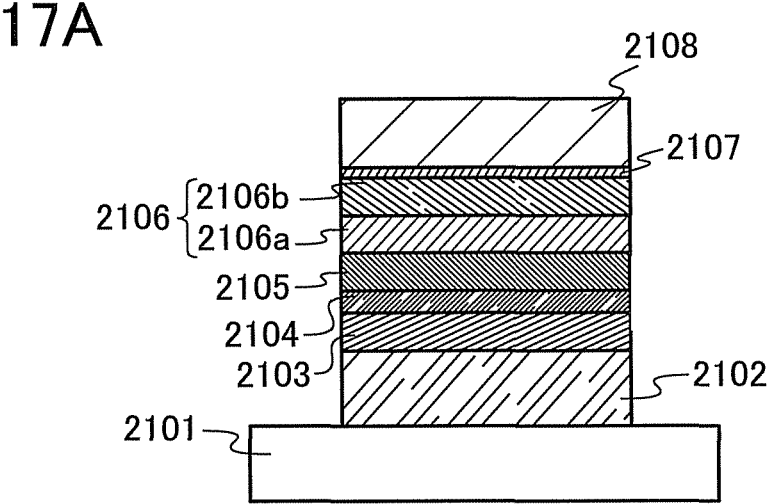
FIGS. 17A and 17B illustrate light-emitting elements of examples.

First, as illustrated in FIG. 17A, indium tin oxide containing silicon oxide (ITSO) was deposited by a sputtering method over a substrate 2101 which is a glass substrate, whereby a first electrode 2102 was formed. The thickness was 110 nm and the electrode area was 2 mm×2 mm. In this example, the first electrode 2102 was used as an anode.

Next, an EL layer having a stack of a plurality of layers was formed over the first electrode 2102. In the light-emitting element 1, the EL layer includes a hole-injection layer 2103, a hole-transport layer 2104, a light-emitting layer 2105, an electron-transport layer 2106, and an electron-injection layer 2107, which are to be stacked in this order.

The substrate 2101 provided with the first electrode 2102 was fixed to a substrate holder in a vacuum evaporation apparatus so that a surface of the substrate 2101 on which the first electrode 2102 was formed faced downward. The pressure was reduced to about $10^{-4}$ Pa. Then, on the first electrode 2102, 4,4'-bis[N-(1-naphthyl)-N-phenylamino]biphenyl (abbreviation: NPB) and molybdenum(VI) oxide were co-evaporated to form the hole-injection layer 2103. The thickness was 50 nm, and the evaporation rate was controlled such that the weight ratio of NPB to molybdenum oxide was 4:1 (=NPB:molybdenum oxide). Note that the co-evaporation method means an evaporation method in which evaporation is carried out from a plurality of evaporation sources at the same time in one treatment chamber.

Next, a hole-transport material was deposited to a thickness of 10 nm on the hole-injection layer 2103 by an evaporation method using resistance heating, whereby the hole-transport layer 2104 was formed. Note that NPB was used for the hole-transport layer 2104.

Next, the light-emitting layer 2105 was formed on the hole-transport layer 2104 by an evaporation method using resistance heating. The light-emitting layer 2105 was formed by co-evaporation of 9-[4-(N-carbazolyl)phenyl]-10-phenylanthracene (abbreviation: CzPA) and N-(dibenzofuran-2-yl)-4-(10-phenylanthracen-9-yl)diphenylamine (abbreviation: FrAPA) to a thickness of 30 nm. Here, the evaporation rate was controlled such that the weight ratio of CzPA to FrAPA was 1:0.1 (=CzPA:FrAPA).

Next, on the light-emitting layer 2105, tris(8-quinolinolato)aluminum (abbreviation: $Alq_3$) was deposited to a thickness of 10 nm to form a first electron-transport layer 2106a.

Then, on the first electron-transport layer 2106a, bathophenanthroline (abbreviation: BPhen) was deposited to a thickness of 20 nm to form a second electron-transport layer 2106b. Thus, the electron-transport layer 2106 formed of the first electron-transport layer 2106a and the second electron-transport layer 2106b was formed.

Further, on the second electron-transport layer 2106b, lithium fluoride (LiF) was evaporated to a thickness of 1 nm to form the electron-injection layer 2107.

Lastly, aluminum was evaporated to a thickness of 200 nm to form a second electrode 2108 functioning as a cathode. Thus, the light-emitting element 1 of this example was fabricated.

(Light-Emitting Element 2)

The light-emitting element 2 was fabricated in a manner similar to that of the light-emitting element 1 except for the light-emitting layer 2105. In the light-emitting element 2, the light-emitting layer 2105 was formed by co-evaporation of 9-[4-(N-carbazolyl)phenyl]-10-phenylanthracene (abbreviation: CzPA) and 4-(dibenzofuran-2-yl)-4'-(10-phenylanthracen-9-yl)triphenylamine (abbreviation: FrBAPA) to a thickness of 30 nm. Here, the evaporation rate was controlled such that the weight ratio of CzPA to FrBAPA was 1:0.1 (=CzPA:FrBAPA).

Thus, the light-emitting element 2 of this example was fabricated.

Element structures of the light-emitting elements 1 and 2 fabricated in this example are shown in Table 2. In Table 2, the mixture ratios are all represented in weight ratios.

TABLE 2

| | First Electrode 2102 | Hole-injection Layer 2103 | Hole-transort Layer 2104 | Light-emitting Layer 2105 | Electron-transport Layer 2106 | | Electron-injection Layer 2107 | Second Electrode 2108 |
|---|---|---|---|---|---|---|---|---|
| Light-emitting Element 1 | ITSO 110 nm | NPB:MoOx (=4:1) 50 nm | NPB 10 nm | CzPA:FrAPA (=1:0.1) 30 nm | 2106a $Alq_3$ 10 nm | 2106b BPhen 20 nm | LiF 1 nm | Al 200 nm |
| Light-emitting Element 2 | ITSO 110 nm | NPB:MoOx (=4:1) 50 nm | NPB 10 nm | CzPA: FrBAPA (=1:0.1) 30 nm | 2106a $Alq_3$ 10 nm | 2106b BPhen 20 nm | LiF 1 nm | Al 200 nm |

The mixture ratios are all represented in weight ratios.

Each of the thus obtained light-emitting elements 1 and 2 was sealed in a glove box under a nitrogen atmosphere so as not to be exposed to the air, and then operation characteristics of the light-emitting elements were measured. Note that the measurements were carried out at room temperature (in an atmosphere kept at 25° C.).

Table 3 shows the voltage (V), current (mA), current density (mA/cm$^2$), CIE chromaticity coordinates (x,y), current efficiency (cd/A), power efficiency (lm/W), and external quantum efficiency (%) of each of the light-emitting elements 1 and 2 at a luminance of about 1000 cd/m$^2$.

TABLE 3

| | Voltage (V) | Current (mA) | Current Density (mA/cm$^2$) | Chromaticity (x, y) | Current Efficiency (cd/A) | Power Efficiency (lm/W) | External Quantum Efficiency (%) |
|---|---|---|---|---|---|---|---|
| Light-emitting Element 1 | 4.4 | 0.87 | 22 | (0.16, 0.18) | 5.0 | 3.6 | 3.7 |
| Light-emitting Element 2 | 4.0 | 0.80 | 20 | (0.16, 0.18) | 4.7 | 3.7 | 3.4 |

Figure 18:
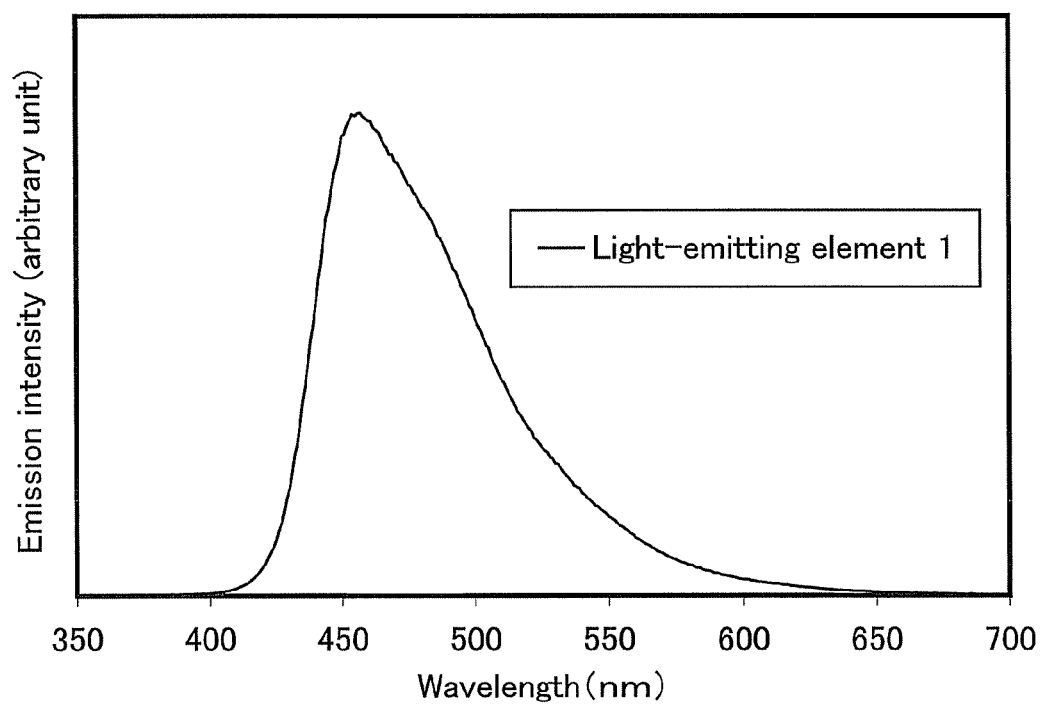
FIG. 18 shows an emission spectrum of a light-emitting element 1.
Figure 19:
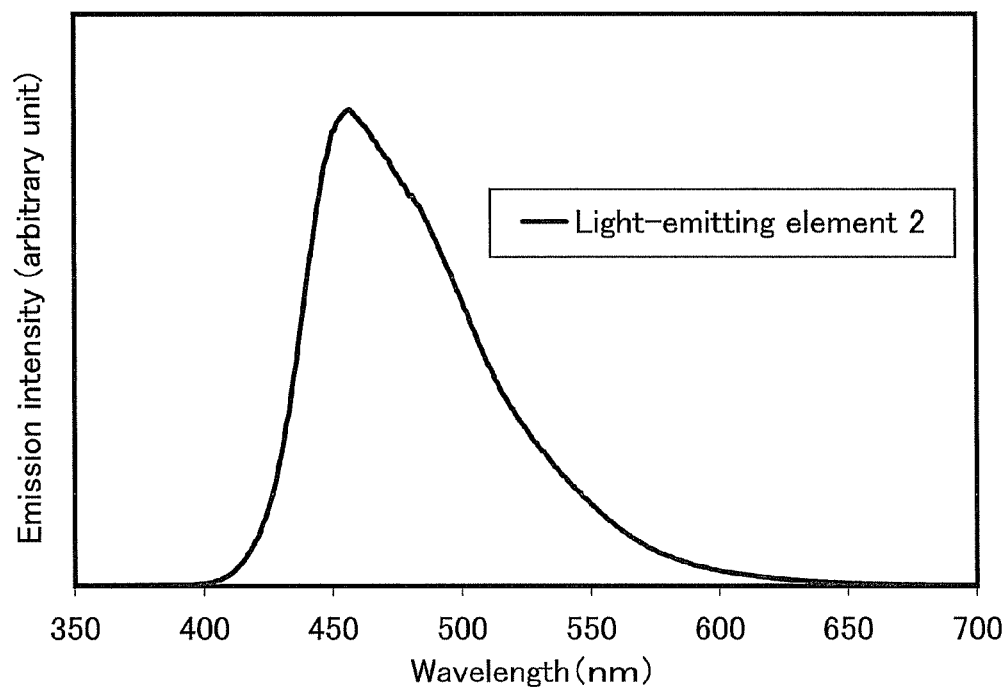
FIG. 19 shows an emission spectrum of a light-emitting element 2.

FIG. 18 shows an emission spectrum of the light-emitting element 1, and FIG. 19 shows an emission spectrum of the light-emitting element 2. In each of FIG. 18 and FIG. 19, the vertical axis represents emission intensity (arbitrary unit), and the horizontal axis represents wavelength (nm).

FIG. 18 and FIG. 19 show that the emission spectra of the light-emitting element 1 and the light-emitting element 2 both have peaks around 460 nm. Thus, as is shown by the CIE chromaticity coordinates in Table 3, it is found that blue light emission was observed from the light-emitting element 1 and the light-emitting element 2. The blue light originates from FrAPA in the light-emitting element 1 and the blue light originates from FrBAPA in the light-emitting element 2, respectively. In addition, it is also found that both light-emitting elements have high color purity.

Figure 21:
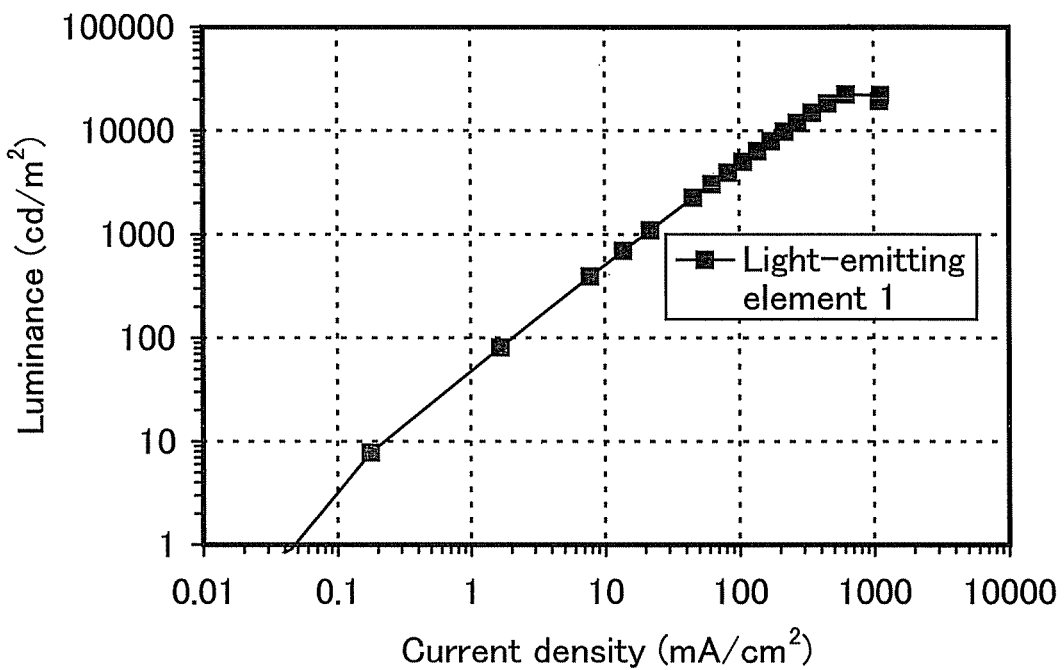
FIG. 21 shows characteristics of current density vs. luminance of the light-emitting element 1.
Figure 22:
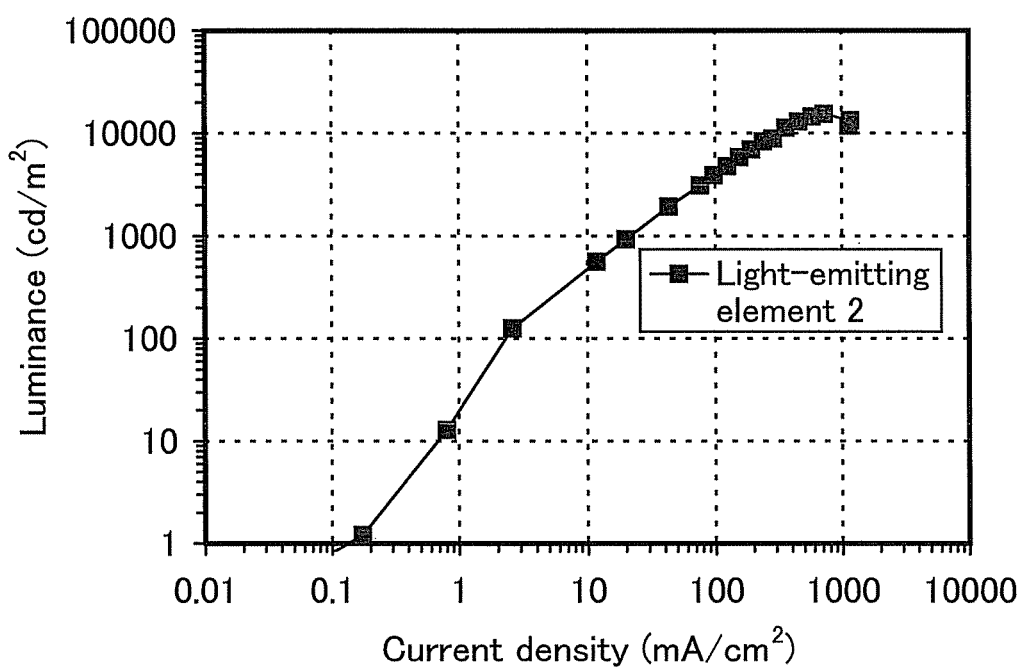
FIG. 22 shows characteristics of current density vs. luminance of the light-emitting element 2.
Figure 24:
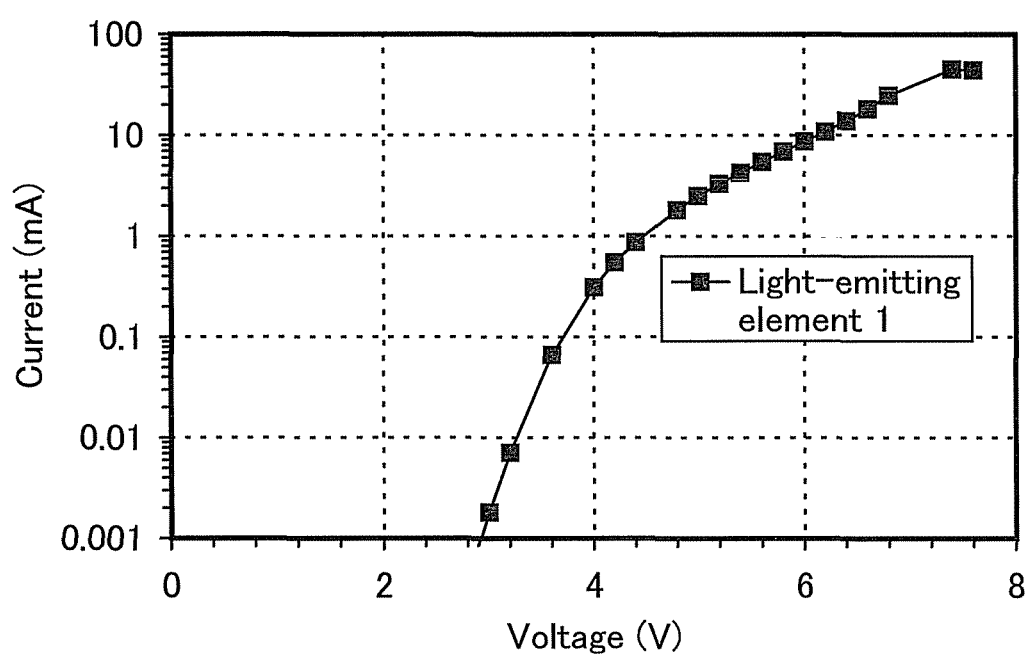
FIG. 24 shows characteristics of voltage vs. current of the light-emitting element 1.
Figure 25:
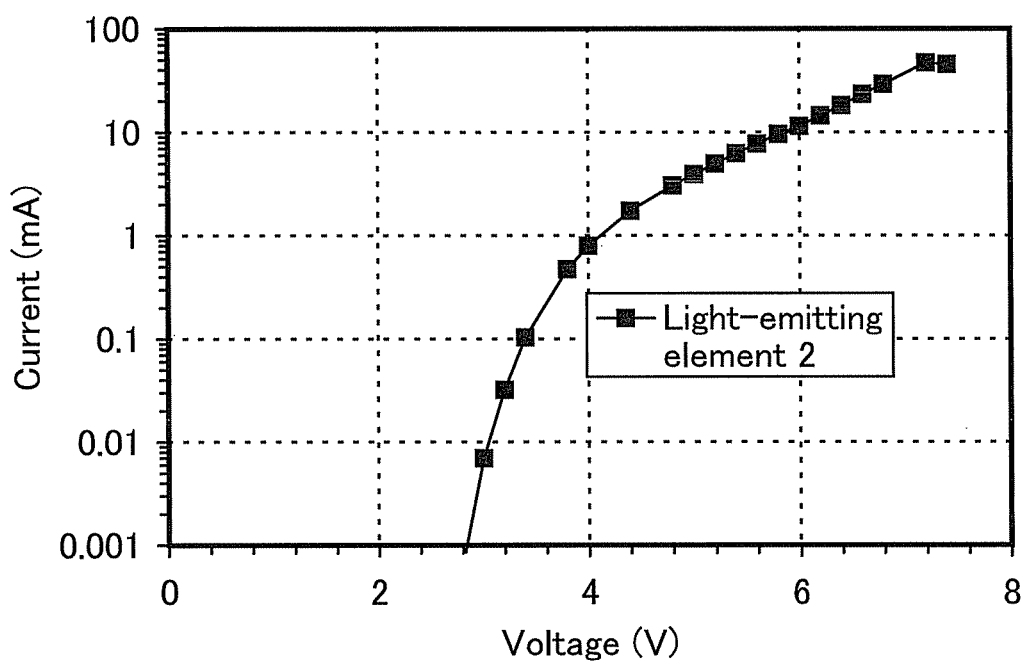
FIG. 25 shows characteristics of voltage vs. current of the light-emitting element 2.
Figure 27:
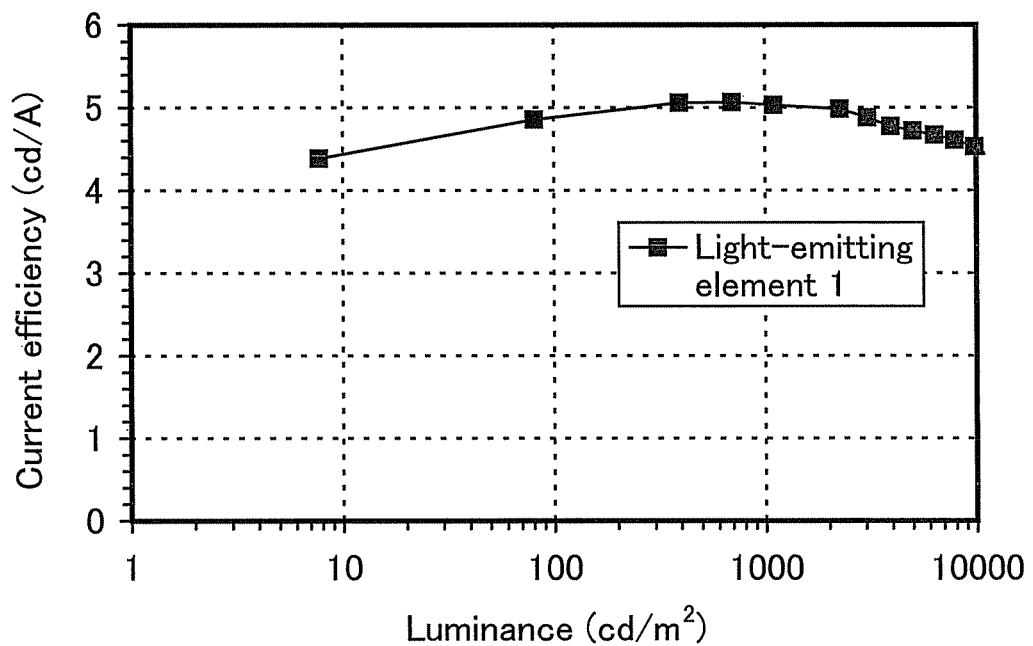
FIG. 27 shows characteristics of luminance vs. current efficiency of the light-emitting element 1.
Figure 28:
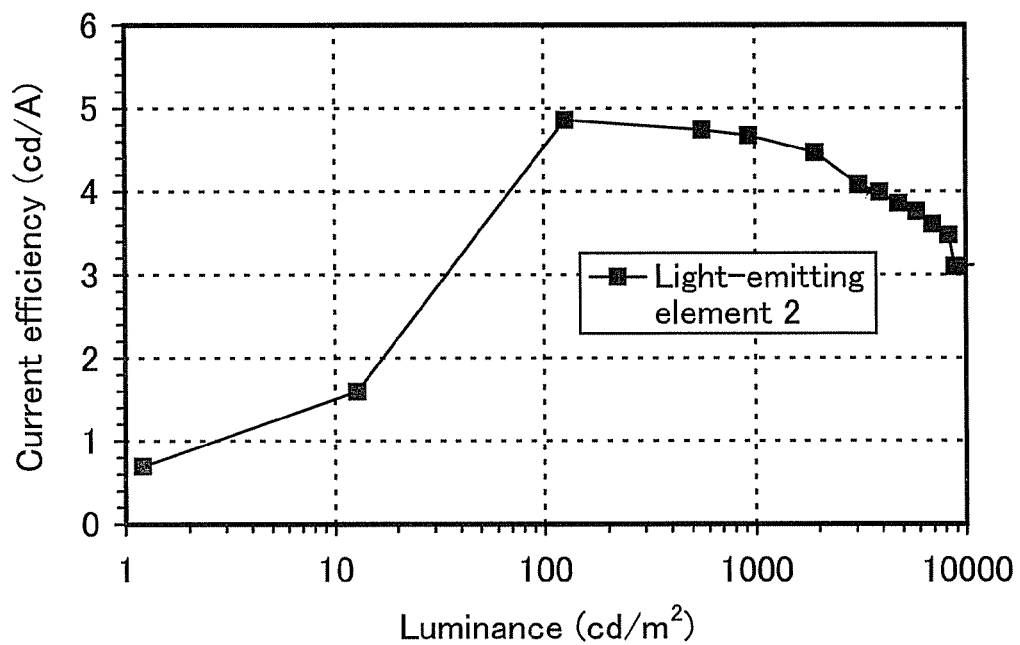
FIG. 28 shows characteristics of luminance vs. current efficiency of the light-emitting element 2.

FIG. 21 shows characteristics of current density vs. luminance of the light-emitting element 1, and FIG. 22 shows those of the light-emitting element 2. In both FIG. 21 and FIG. 22, the horizontal axis represents current density (mA/cm$^2$) and the vertical axis represents luminance (cd/m$^2$). In addition, FIG. 24 shows characteristics of voltage vs. current of the light-emitting element 1, and FIG. 25 shows those of the light-emitting element 2. In both FIG. 24 and FIG. 25, the horizontal axis represents voltage (V) and the vertical axis represents current (mA). Further, FIG. 27 shows characteristics of luminance vs. current efficiency of the light-emitting element 1, and FIG. 28 shows those of the light-emitting element 2. In both FIG. 27 and FIG. 28, the horizontal axis represents luminance (cd/m$^2$) and the vertical axis represents current efficiency (cd/A).

From FIG. 21, FIG. 22, FIG. 24, FIG. 25, FIG. 27, FIG. 28, and Table 3, it is found that the light-emitting elements 1 and 2 can be driven at low voltages and have high efficiency.

Figure 30:
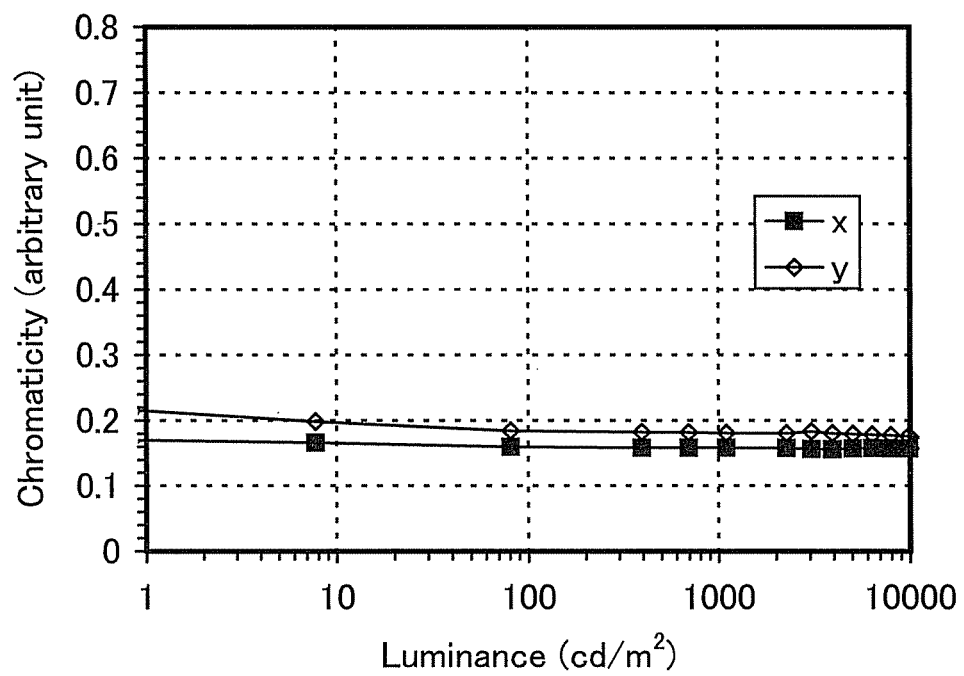
FIG. 30 shows characteristics of luminance vs. chromaticity of the light-emitting element 1.
Figure 31:
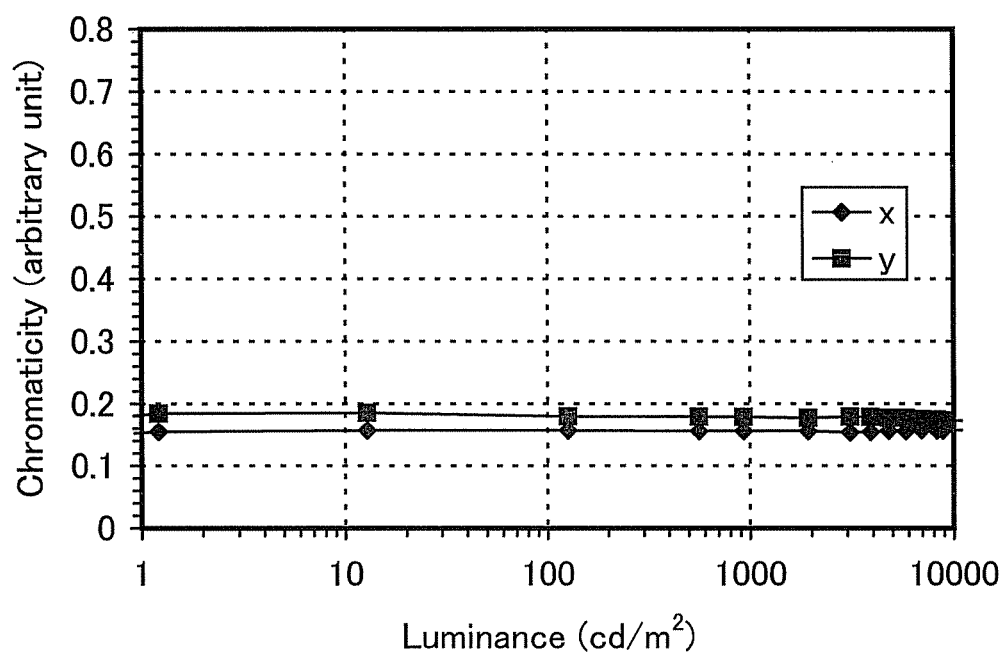
FIG. 31 shows characteristics of luminance vs. chromaticity of the light-emitting element 2.

In addition, FIG. 30 shows characteristics of luminance vs. chromaticity of the light-emitting element 1, and FIG. 31 shows those of the light-emitting element 2. In both FIG. 30 and FIG. 31, the horizontal axis represents luminance (cd/m$^2$) and the vertical axis represents chromaticity (arbitrary unit).

From FIG. 30 and FIG. 31, it is found that the chromaticity of the blue lights that originate from FrAPA and FrBAPA do not change even when the luminances of the light-emitting elements 1 and 2 are changed. Thus, the light-emitting elements 1 and 2 have favorable carrier balance, and color shift is barely likely to occur in dimming. Therefore, the light-emitting elements 1 and 2 can be used favorably for a full-color display and the like.

Figure 33:
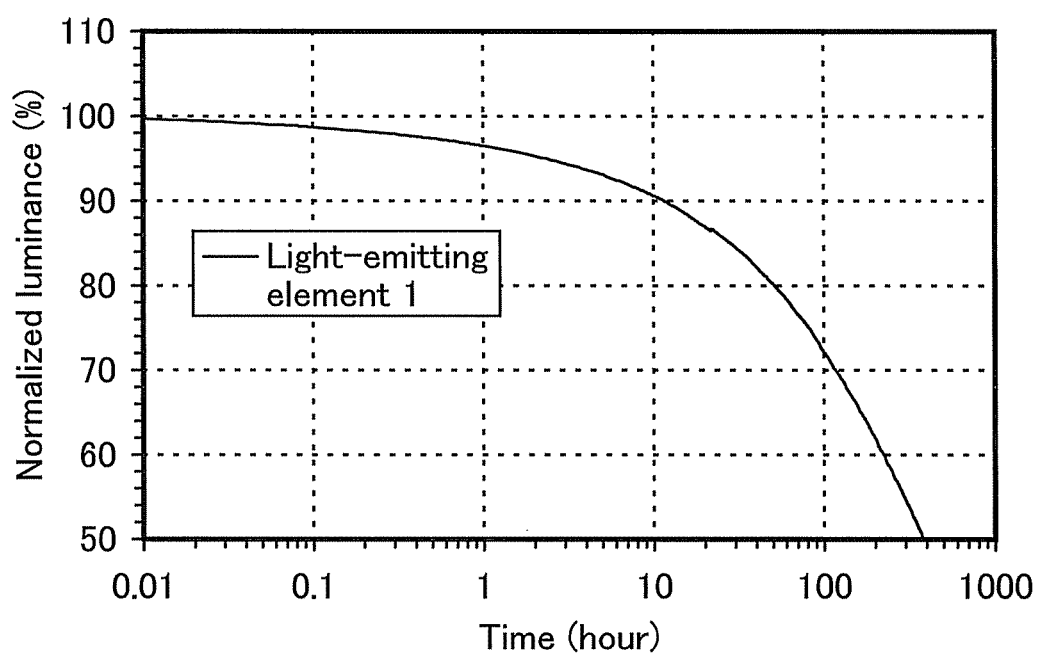
FIG. 33 shows results of a reliability test of the light-emitting element 1.

Further, a reliability test of the fabricated light-emitting element 1 was performed. In the reliability test, the initial luminance was set at 1000 cd/m$^2$, the element was driven at the constant current density, and the luminance was measured at regular intervals. Results of the reliability test are shown in FIG. 33. In FIG. 33, the horizontal axis represents current flow time (hour), and the vertical axis represents the proportion of luminance at each time in the initial luminance, i.e., normalized luminance (%).

From FIG. 33, it is found that the luminance of the light-emitting element 1 does not easily decrease with the passage of time, and the light-emitting element 1 has long lifetime. In addition, the light-emitting element 1 kept about 50% of the initial luminance after driving for 380 hours.

As described above, it is confirmed that the light-emitting elements 1 and 2 of this example can be favorable blue light-emitting elements, and in particular, the light-emitting element 1 can be a blue light-emitting element with high color purity.

Example 6

In this example are described a method of fabricating a light-emitting element in which the anthracene compound according to one embodiment of the present invention, which is synthesized in Example 3, is used as a light-emitting material, and results of measuring the element characteristics. Note that organic compounds used in this example are similar to those in Example 5; therefore, the description of the organic compounds is omitted.

Figure 17B:
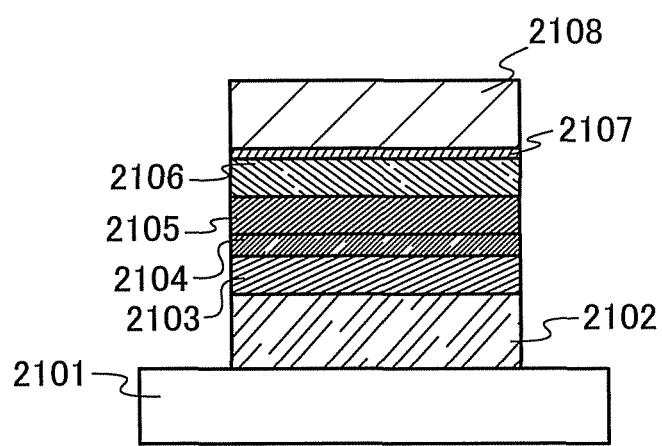

A method for fabricating a light-emitting element 3 is described below with reference to FIG. 17B.

(Light-Emitting Element 3)

The light-emitting element 3 was fabricated in the same manner as the light-emitting element 1 except for the light-emitting layer 2105, the electron-transport layer 2106, and the electron-injection layer 2107. In the light-emitting element 3, the light-emitting layer 2105 was formed by co-evaporation of 9-[4-(N-carbazolyl)phenyl]-10-phenylanthracene (abbreviation: CzPA) and N-(dibenzothiophen-2-yl)-4-(10-phenylanthracen-9-yl)diphenylamine (abbreviation: ThAPA) to a thickness of 30 nm, as illustrated in FIG. 17B. Here, the evaporation rate was controlled such that the weight ratio of CzPA to ThAPA was 1:0.04 (=CzPA:ThAPA).

Next, over the light-emitting layer 2105, an electron-transport material was deposited to a thickness of 10 nm to form the electron-transport layer 2106. Note that the electron-transport layer 2106 was Ruined using tris(8-quinolinolato) aluminum (abbreviation: Alq$_3$).

Further, over the second electron-transport layer 2106b, the electron-injection layer 2107 was formed by co-evaporation of tris(8-quinolinolato)aluminum (abbreviation: Alq$_3$) and lithium (Li) to a thickness of 20 nm. Here, the evaporation rate was controlled such that the weight ratio of Alq$_3$ and Li was 1:0.01 (=Alq$_3$:Li).

Thus, the light-emitting element 3 of this example was fabricated.

Table 4 shows an element structure of the light-emitting element 3 fabricated in this example. In Table 4, the mixture ratios are all represented in weight ratios.

TABLE 4

| | First Electrode 2102 | Hole-injection Layer 2103 | Hole-transport Layer 2104 | Light-emitting Layer 2105 | Electron-transport Layer 2106 | Electron-injection Layer 2107 | Second Electrode 2108 |
|---|---|---|---|---|---|---|---|
| Light-emitting Element 3 | ITSO 110 nm | NPB:MoOx (=4:1) 50 nm | NPB 10 nm | CzPA:ThAPA (=1:0.08) 30 nm | Alq$_3$ 10 nm | Alq$_3$:Li (=1:0.01) 20 nm | Al 200 nm |

The mixture ratios are all represented in weight ratios.

The thus obtained light-emitting element 3 was sealed in a glove box under a nitrogen atmosphere so as not to be exposed to the air, and then operation characteristics of the light-emitting element were measured. Note that the measurements were carried out at room temperature (in an atmosphere kept at 25° C.).

Table 5 shows the voltage (V), current (mA), current density (mA/cm$^2$), CIE chromaticity coordinates (x,y), current efficiency (cd/A), power efficiency (lm/W), and external quantum efficiency (%) of the light-emitting element 3 at a luminance of about 1000 cd/m$^2$.

TABLE 5

| | Voltage (V) | Current (mA) | Current Density (mA/cm$^2$) | Chromaticity (x, y) | Current Efficiency (cd/A) | Power Efficiency (lm/W) | External Quantum Efficiency (%) |
|---|---|---|---|---|---|---|---|
| Light-emitting Element 3 | 4.2 | 1.9 | 49 | (0.15, 0.16) | 1.9 | 1.4 | 1.6 |

Figure 20:
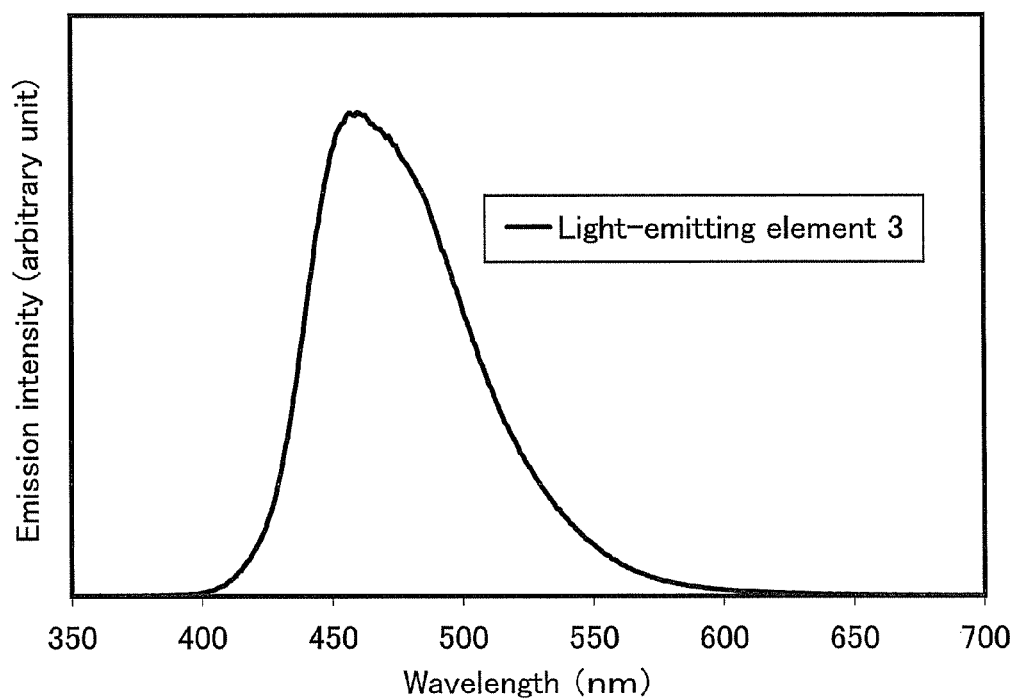
FIG. 20 shows an emission spectrum of a light-emitting element 3.

FIG. 20 shows an emission spectrum of the light-emitting element 3. In FIG. 20, the vertical axis represents emission intensity (arbitrary unit), and the horizontal axis represents wavelength (nm).

FIG. 20 shows that the emission spectrum of the light-emitting element 3 has a peak around 460 nm. Thus, as is shown by the CIE chromaticity coordinates in Table 5, it is found that blue light emission that originates from ThAPA was observed from the light-emitting element 3. In addition, it is also found that the light-emitting material has high color purity.

Figure 23:
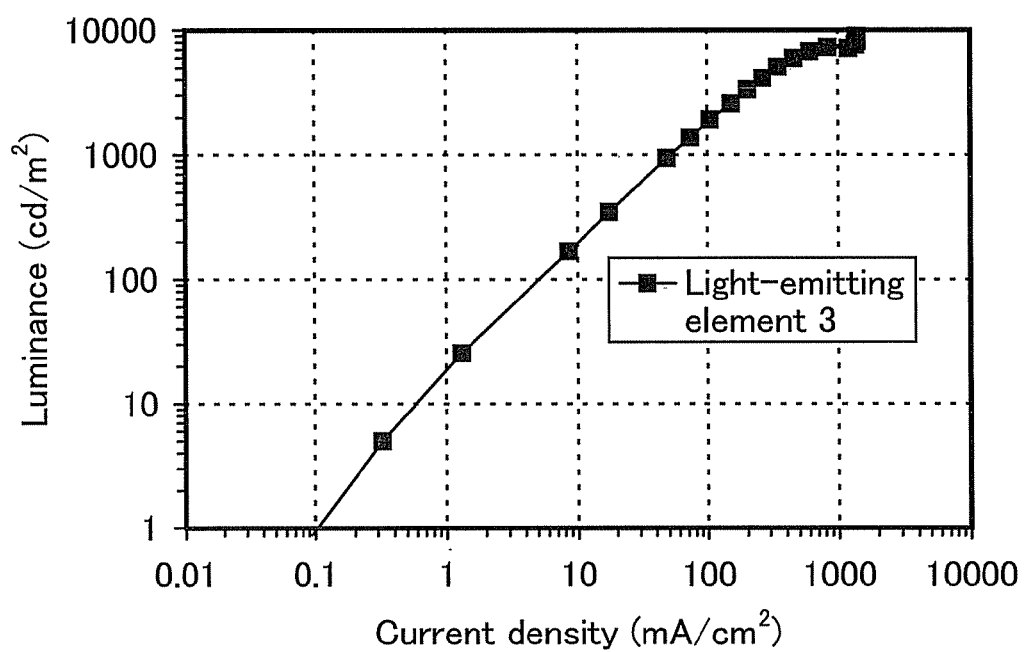
FIG. 23 shows characteristics of current density vs. luminance of the light-emitting element 3.
Figure 26:
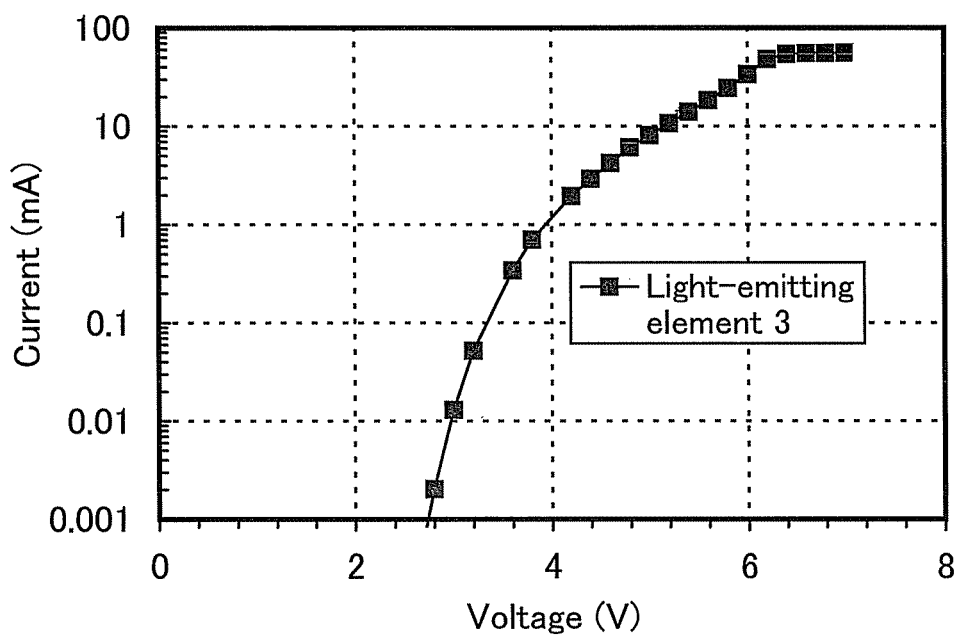
FIG. 26 shows characteristics of voltage vs. current of the light-emitting element 3.
Figure 29:
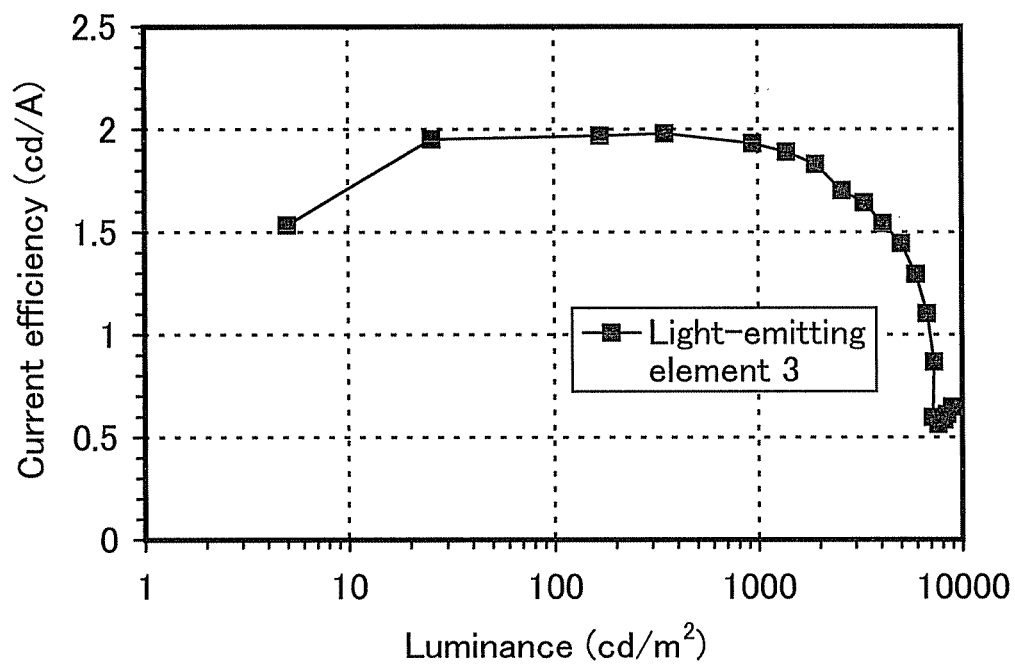
FIG. 29 shows characteristics of luminance vs. current efficiency of the light-emitting element 3.

FIG. 23 shows characteristics of current density vs. luminance of the light-emitting element 3. In FIG. 23, the horizontal axis represents current density (mA/cm$^2$) and the vertical axis represents luminance (cd/m$^2$). In addition, FIG. 26 shows characteristics of voltage vs. current of the light-emitting element 3. In FIG. 26, the horizontal axis represents voltage (V) and the vertical axis represents current (mA). Further, FIG. 29 shows characteristics of luminance vs. current efficiency of the light-emitting element 3. In FIG. 29, the horizontal axis represents luminance (cd/m$^2$) and the vertical axis represents current efficiency (cd/A).

From FIG. 23, FIG. 26, FIG. 29, and Table 5, it is found that the light-emitting element 3 can also be driven at a low voltage and has high efficiency.

Figure 32:
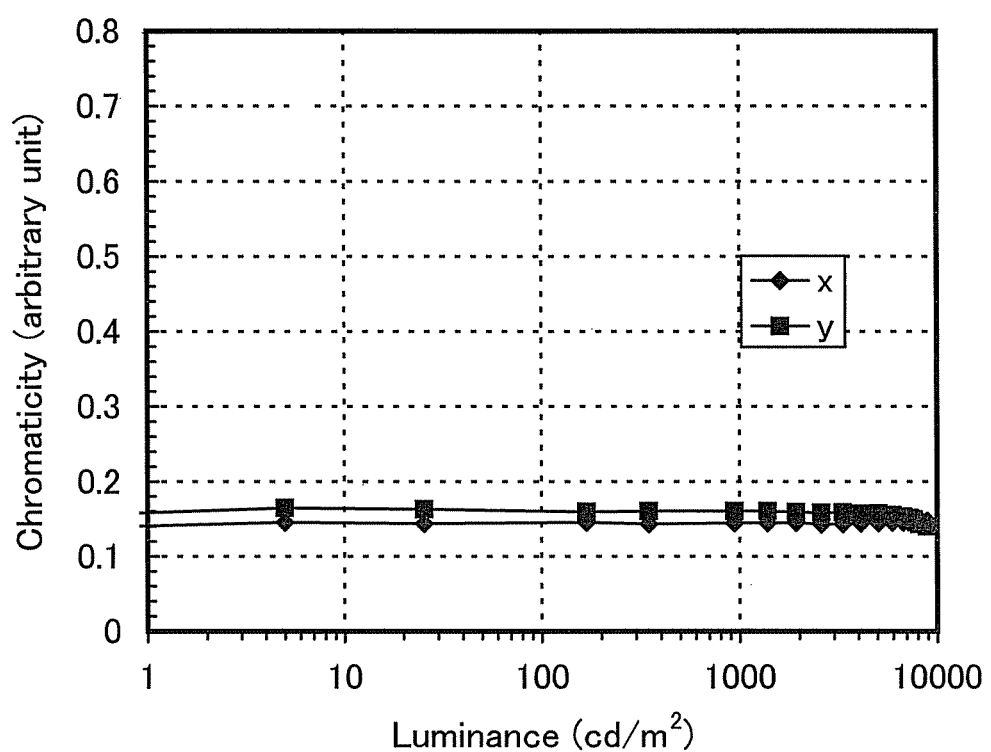
FIG. 32 shows characteristics of luminance vs. chromaticity of the light-emitting element 3.

In addition, FIG. 32 shows characteristics of luminance vs. chromaticity of the light-emitting element 3. In FIG. 32, the horizontal axis represents luminance (cd/m$^2$) and the vertical axis represents chromaticity (arbitrary unit).

From FIG. 32, it is found that the chromaticity of the blue light that originates from ThAPA does not change even when the luminance of the light-emitting element 3 is changed. Thus, the light-emitting element 3 has favorable carrier balance, and color shift is barely likely to occur in dimming. Therefore, the light-emitting element 3 can be used favorably for a full-color display and the like.

Figure 34:
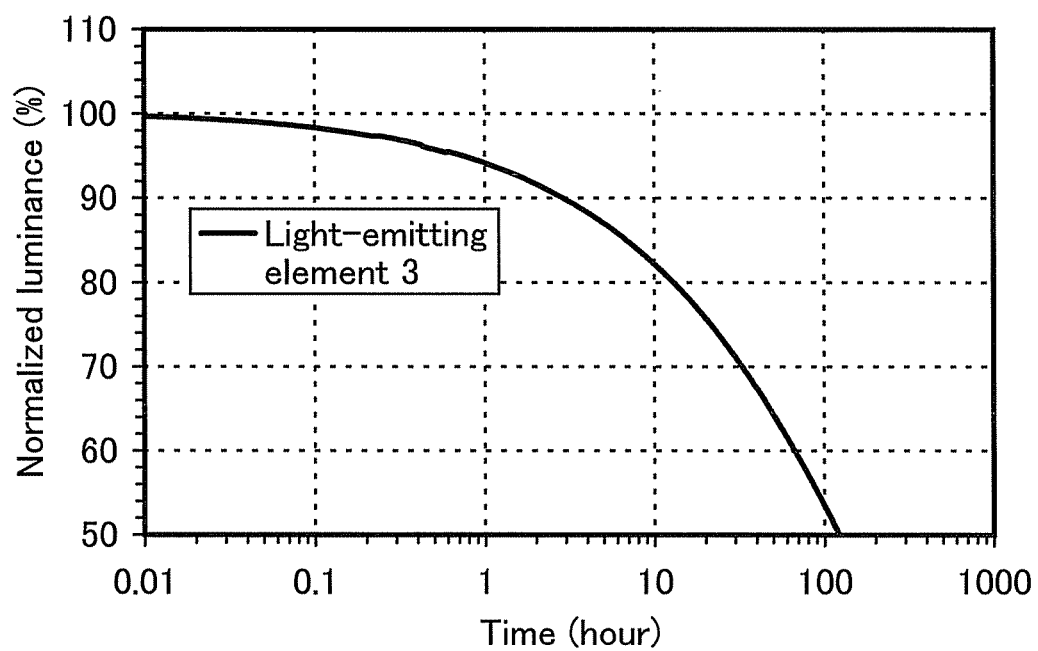
FIG. 34 shows results of a reliability test of the light-emitting element 3.

Further, a reliability test of the fabricated light-emitting element 3 was performed. In the reliability test, the initial luminance was set at 1000 cd/m$^2$, the element was driven at the constant current density, and the luminance was measured at regular intervals. Results of the reliability test are shown in FIG. 34. In FIG. 34, the horizontal axis represents current flow time (hour), and the vertical axis represents the proportion of luminance at each time in the initial luminance, i.e., normalized luminance (%).

From FIG. 34, it is found that the luminance of the light-emitting element 3 does not easily decrease with the passage of time, and the light-emitting element 3 has long lifetime. In addition, the light-emitting element 3 kept about 50% of the initial luminance after driving for 120 hours.

As described above, it is confirmed that the light-emitting element 3 of this example can be a favorable blue light-emitting element, and a blue light-emitting element with high color purity.

This application is based on Japanese Patent Application serial no. 2010-281941 filed with Japan Patent Office on Dec. 17, 2010, the entire contents of which are hereby incorporated by reference.

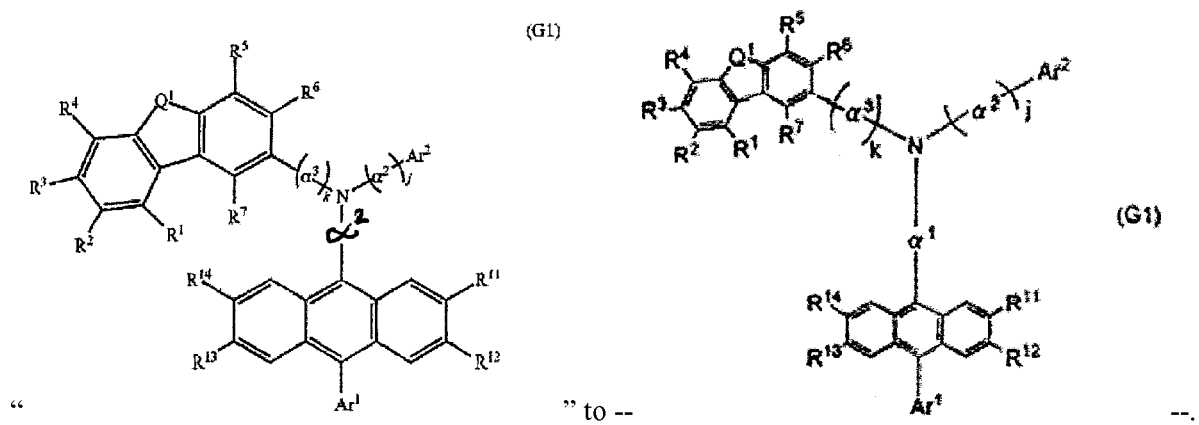

What is claimed is:

1. An anthracene compound represented by a general formula (G1),

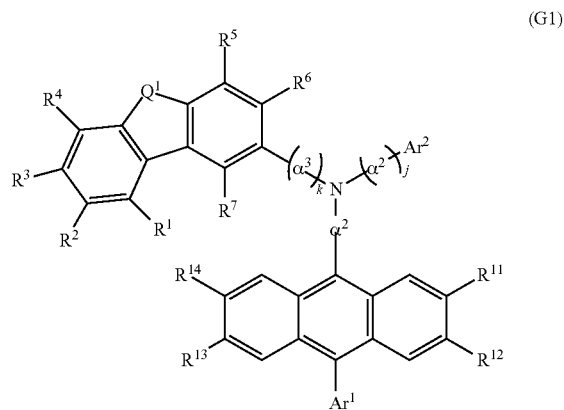

(G1)

wherein:

$Q^1$ represents an oxygen atom or a sulfur atom, $R^1$ to $R^7$ and $R^{11}$ to $R^{14}$ separately represent any one of a hydrogen atom, an alkyl group having 1 to 6 carbon atoms, a substituted or unsubstituted phenyl group, and a substituted or unsubstituted biphenyl group, $\alpha^1$ to $\alpha^3$ separately represent a substituted or unsubstituted phenylene group, $Ar^1$ represents a substituted or unsubstituted condensed aromatic hydrocarbon having 6 to 12 carbon atoms forming a ring, $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group, and j and k are separately 0 or 1.

2. The anthracene compound according to claim 1, wherein $\alpha^1$ to $\alpha^3$ separately represent any one of structures represented by structural formulas (α-1) to (α-3),

(α-1)

-continued

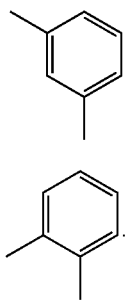

(α-2)

(α-3)

3. The anthracene compound according to claim 1, wherein the anthracene compound is represented by a general formula (G2),

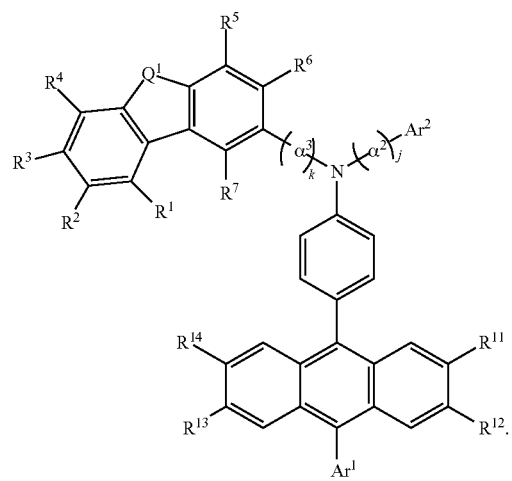

(G2)

4. The anthracene compound according to claim 1, wherein the anthracene compound is represented by a general formula (G3),

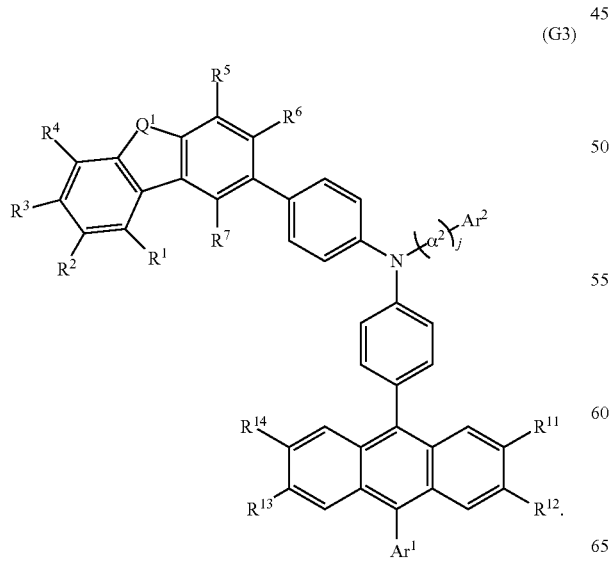

(G3)

5. The anthracene compound according to claim 1, wherein Ar$^1$ represents any one of structures represented by structural formulas (Ar1-1) to (Ar1-4),

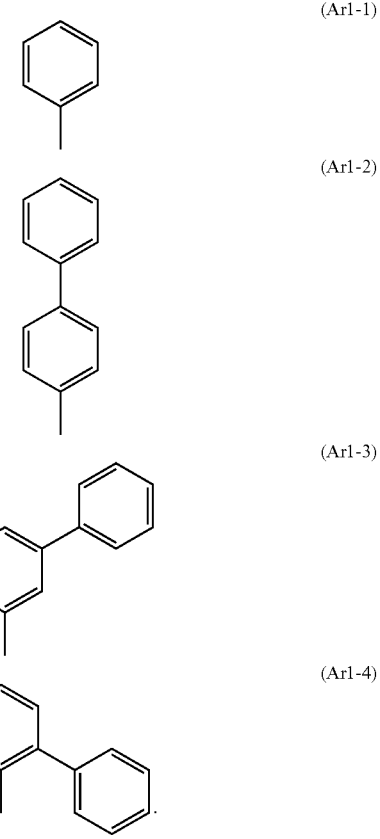

(Ar1-1)

(Ar1-2)

(Ar1-3)

(Ar1-4)

6. The anthracene compound according to claim 1, wherein Ar$^2$ represents a structure represented by a structural formula (Ar2-1) or a general formula (Ar2-2),

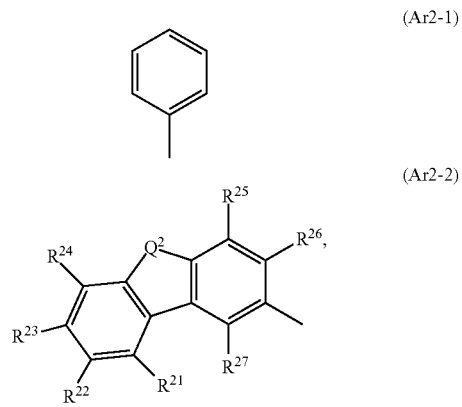

(Ar2-1)

(Ar2-2)

wherein Q$^2$ represents an oxygen atom or a sulfur atom, and wherein R$^{21}$ to R$^{27}$ separately represent any one of a hydrogen atom, an alkyl group having 1 to 6 carbon atoms, a substituted or unsubstituted phenyl group, and a substituted or unsubstituted biphenyl group.

7. The anthracene compound according to claim 1,
wherein $R^1$ to $R^7$ and $R^{11}$ to $R^{14}$ separately represent any one of structures represented by structural formulas (R-1) to (R-9),

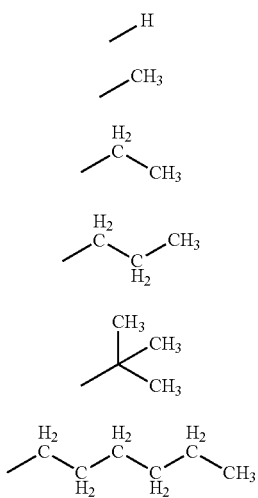

(R-1)
(R-2)
(R-3)
(R-4)
(R-5)
(R-6)

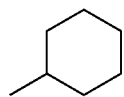

(R-7)

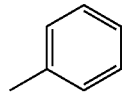

(R-8)

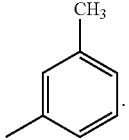

(R-9)

8. A light-emitting element comprising the anthracene compound according to claim 1.

9. A light-emitting device comprising the light-emitting element according to claim 8.

10. A lighting device comprising the light-emitting device according to claim 9.

11. An electronic device comprising the light-emitting device according to claim 9.

* * * * *

UNITED STATES PATENT AND TRADEMARK OFFICE
CERTIFICATE OF CORRECTION

Page 1 of 3

PATENT NO. : 8,580,980 B2
APPLICATION NO. : 13/328541
DATED : November 12, 2013
INVENTOR(S) : Harue Osaka and Nobuharu Ohsawa It is certified that error appears in the above-identified patent and that said Letters Patent is hereby corrected as shown below:

In the Specification:

Column 1, line 32; Change "fainted." to --formed.--.
Column 23, lines 15 to 49, synthesis scheme (A-4); Change

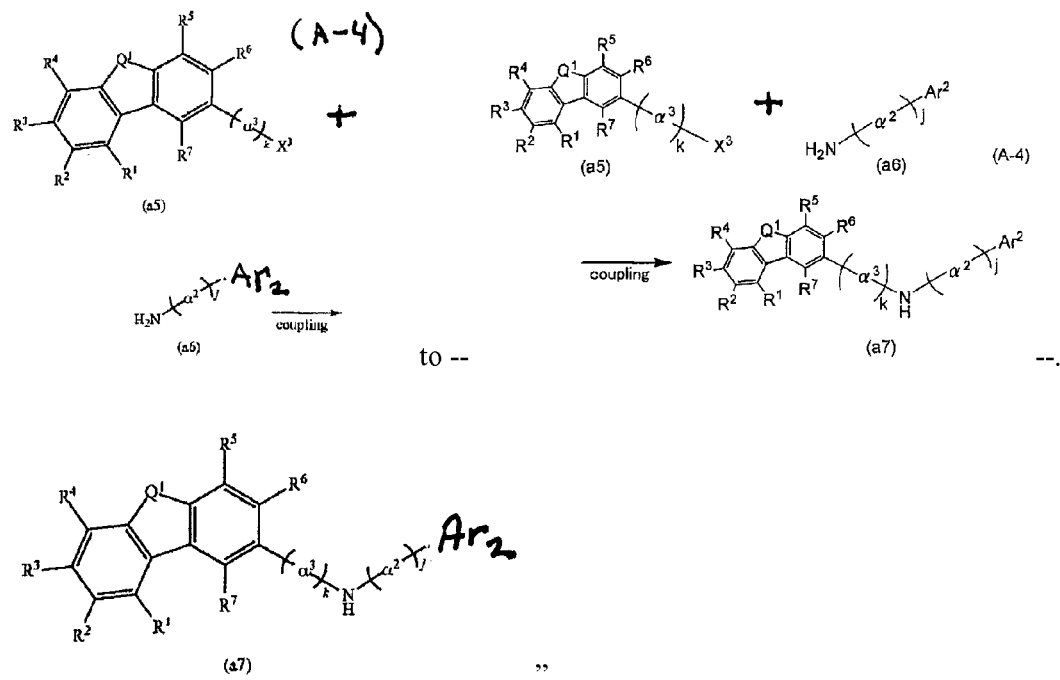

Signed and Sealed this
Sixth Day of May, 2014

Michelle K. Lee
*Deputy Director of the United States Patent and Trademark Office*

CERTIFICATE OF CORRECTION (continued)
U.S. Pat. No. 8,580,980 B2

Column 25, lines 1 to 40, synthesis scheme (A-5); Change

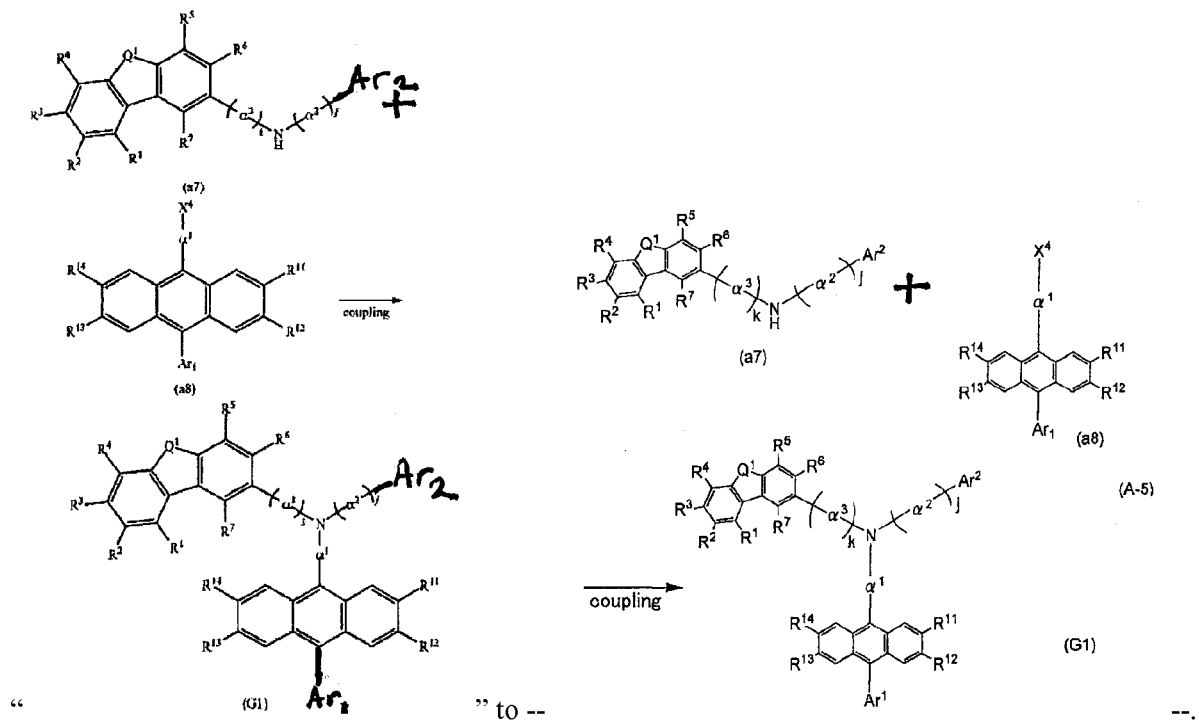

" to --  --.

Column 26, lines 10 to 38, synthesis scheme (A-6); Change

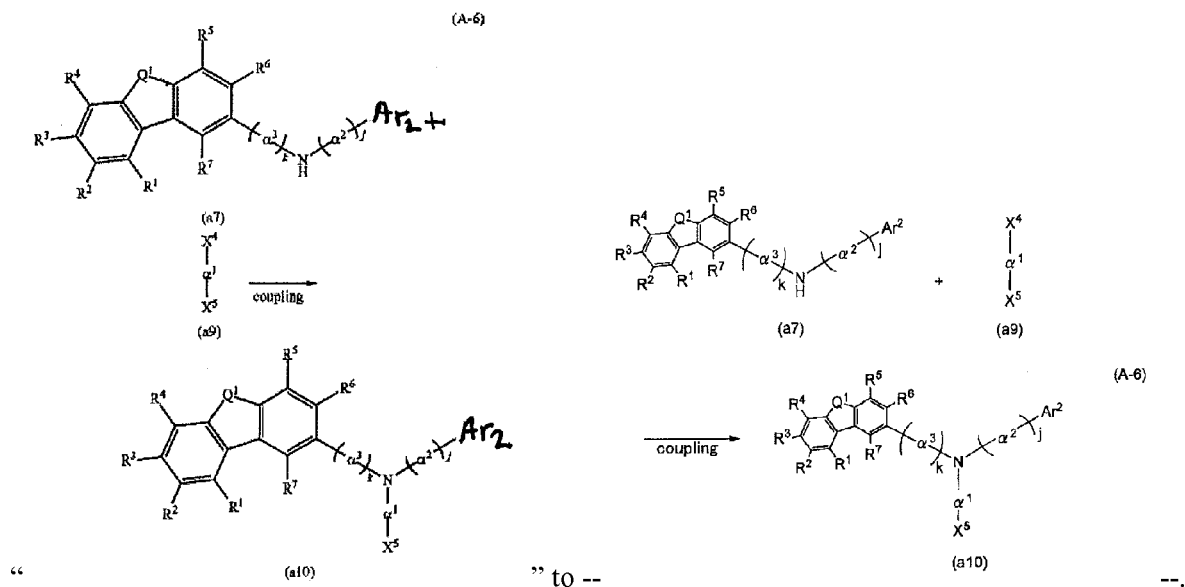

" to --  --.

CERTIFICATE OF CORRECTION (continued)
U.S. Pat. No. 8,580,980 B2

Column 27, lines 5 to 44, synthesis scheme (A-7); Change

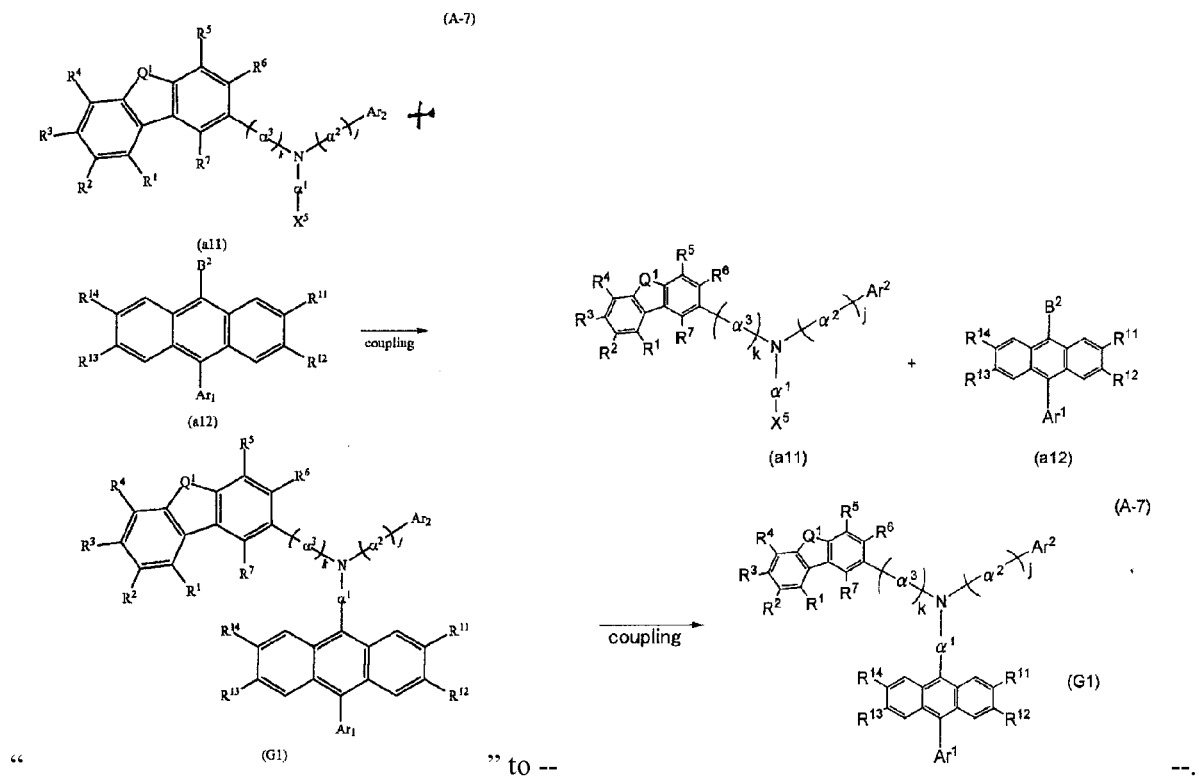

Column 28, line 31; Change "composite, material" to --composite material--.
Column 34, line 38; Change "foamed" to --formed--.
Column 40, line 55; Change "fowled" to --formed--.
Column 62, line 32; Change "Ruined" to --formed--.

In the Claims

Column 64, lines 15 to 34, claim 1, general formula (G1); Change